United States Patent
O'Mahony et al.

(10) Patent No.: US 9,394,291 B2
(45) Date of Patent: Jul. 19, 2016

(54) BENZOXAZINONE AMIDES AS MINERALOCORTICOID RECEPTOR MODULATORS

(71) Applicant: AstraZeneca AB, Södertälje (SE)

(72) Inventors: Gavin O'Mahony, Mölndal (SE); Michael Kossenjans, Mölndal (SE); Karl Edman, Mölndal (SE); Johan Kajanus, Mölndal (SE); Karl Anders Hogner, Mölndal (SE); Philip Cornwall, Macclesfield (GB); Andrew Turner, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 14/753,239

(22) Filed: Jun. 29, 2015

(65) Prior Publication Data

US 2015/0376170 A1    Dec. 31, 2015

Related U.S. Application Data

(60) Provisional application No. 62/018,790, filed on Jun. 30, 2014.

(51) Int. Cl.
| | | |
|---|---|---|
| C07D 413/10 | (2006.01) | |
| C07D 413/06 | (2006.01) | |
| C07D 265/36 | (2006.01) | |

(52) U.S. Cl.
CPC ............ *C07D 413/06* (2013.01); *C07D 265/36* (2013.01)

(58) Field of Classification Search
CPC ...................................................... C07D 413/10
USPC ....................................... 514/230.5; 544/105
See application file for complete search history.

(56) References Cited

U.S. PATENT DOCUMENTS

2010/0094000 A1   4/2010 Fukumoto et al.

FOREIGN PATENT DOCUMENTS

| | | |
|---|---|---|
| DE | 102007009494 A1 | 8/2008 |
| WO | WO 2006/015259 A3 | 2/2006 |
| WO | WO 2007/077961 A3 | 7/2007 |
| WO | WO 2007/089034 A1 | 8/2007 |
| WO | WO 2008/053300 A1 | 5/2008 |
| WO | WO 2008/118319 A3 | 10/2008 |
| WO | WO 2008/126831 A1 | 10/2008 |
| WO | WO 2009/017190 A1 | 2/2009 |
| WO | WO 2009/085584 A1 | 7/2009 |
| WO | WO 2010/098286 A1 | 9/2010 |
| WO | WO 2010/104721 A1 | 9/2010 |
| WO | WO 2010/116282 A8 | 10/2010 |
| WO | WO 2011/141846 A1 | 11/2011 |
| WO | WO 2012/008435 A1 | 1/2012 |
| WO | WO 2012/064631 A1 | 5/2012 |

OTHER PUBLICATIONS

Barfacker et al., 'Discovery of BAY 94/8862: A Nonsteroidal Antagonist of the Mineralocorticoid Receptor for the treatment of Cardiorenal Diseases'. Chem Med Chem (2012); vol. 7; No. 8; 1385-1403.

Casimiro-Garcia et al., 'Identification of (R)-6-(1-(4-Cyano-3-methylphenyl)-5-cyclopentyl-4,5-dihydro-1*H*-pyrazol-3-yl)-2-methoxynicotinic Acid, A Highly Potent and Selective Nonsteroidal Mineralocorticoid Receptor Antagonist'. J. Med Chem (2014; vol. 57, No. 10: 4273-4288.

Collin et al., 'Mineralocorticoid Receptor Modulators: A Patent Review (2007-2012)'. Expert Opinion Ther Patents (2014); vol. 24; No, 2: 177-183.

Hasui et al, 'Identification of Benzoxazin-3-one Derivatives as Novel, Potent, and Selective Nonsteroidal mineralocorticoid Receptor Antagonists'. J. Med Chem (2011); vol. 54; 8616-8631.

Kolkhof and Borden, 'Molecular Pharmacology of the Mineralocorticoid Receptor: Prospects for Novel Therapeutics'. Mol and Cell Endocrinology (2012); vol. 350: 310-317.

Meyers and Hu, 'Non-Steroidal Mineralocorticoid Receptor Antagonists', Expert Opinion Ther Patents (2007); vol. 17; No. 1; 17-23.

Nariai et al., 'SM-368229. A Novel Promising Mineralocorticoid Receptor Antagonist, Shows Antihypertensive efficacy with Minimal Effect on Serum Potassium Level in Rats'. J. Cardiovasc Pharmacol (2012); vol. 59; No. 5; 458-464.

Neel et al., '3,3-Bisaryloxindoles as Mineralocorticoid Receptor Antagonists'. Bioorg and Medicinal Chem Lett (2005); vol. 15; 2553-2557.

Orena et al.; 'PF-03862845, A Non-steroidal Mineralocorticoid Receptor Antagonist, Prevents Renal Injury with Reduced Risk of Hyperkalemia in an Animal Model of Nephropathy'. Frontiers in Pharmacol (2013); vol. 4; 1-11.

Piotrowski, 'Mineralocorticoid Receptor Antagonists for the Treatment of Hypertension and Diabetic Nephropathy'. J. Med Chem (2012); vol. 55; 7957-7966.

Yang et al., 'Discovery of Novel Oxazolidinedione Derivatives as Potent and Selective Mineralocorticoid Receptor Antagonists'. Bioorg and Medicinal Chem Lett (2013): vol. 23; 4388-4392.

*Primary Examiner* — Kahsay Habte

(57) ABSTRACT

Disclosed are certain derivatives of benzoxazinone amides of formula (I), or pharmaceutically acceptable salts thereof,

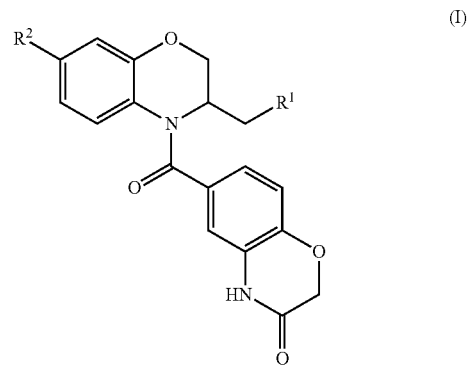

(I)

that act as mineralocorticoid (MR) receptor modulators that may reduce oxidative stress in endothelium and hence improve vascular function, to methods for their potential therapeutic use, to pharmaceutical compositions containing them and to processes for preparing such compounds.

5 Claims, 1 Drawing Sheet

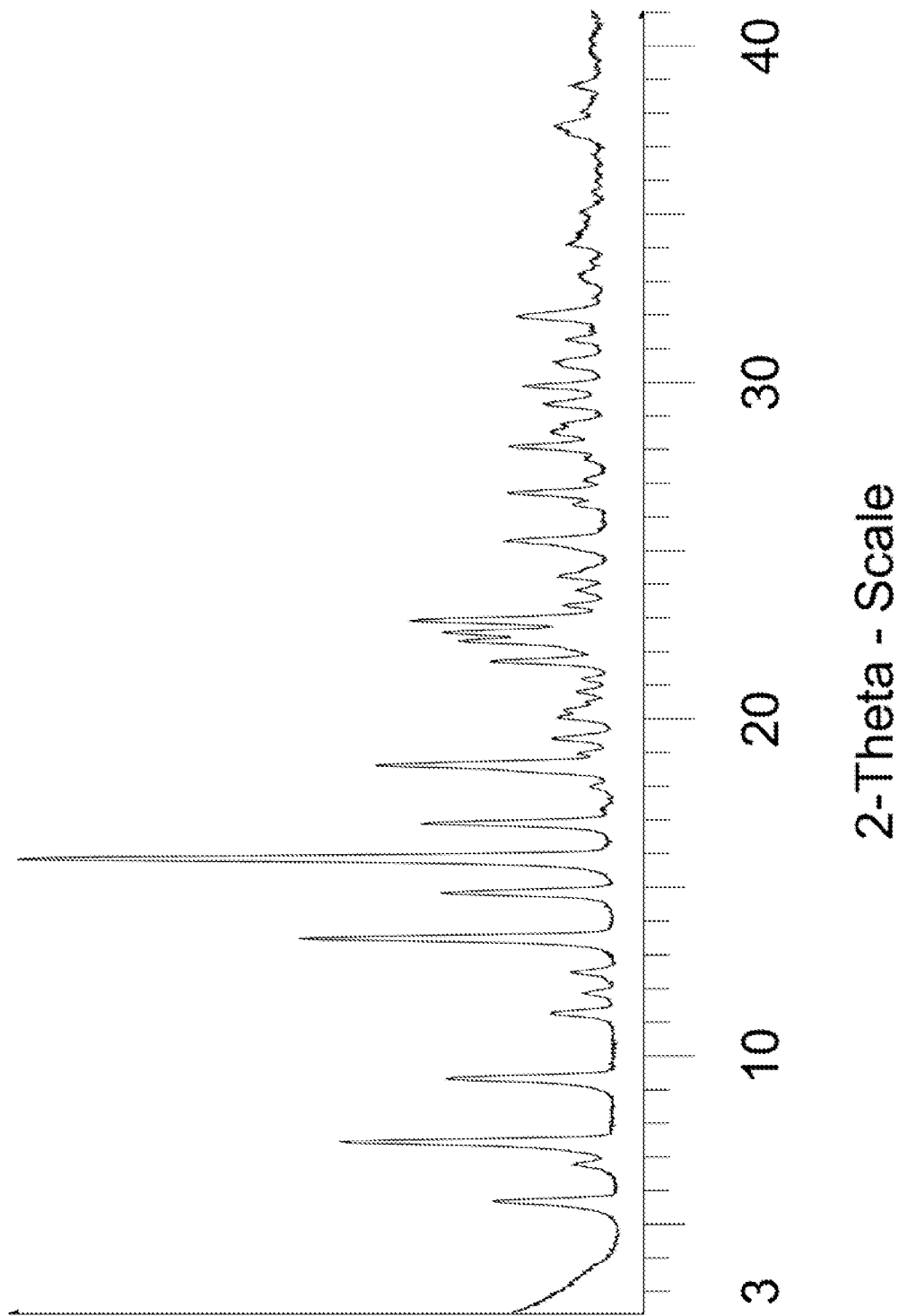

BENZOXAZINONE AMIDES AS MINERALOCORTICOID RECEPTOR MODULATORS

TECHNICAL FIELD

The technical field relates to certain derivatives of benzoxazinone amides (including pharmaceutically acceptable salts thereof) that act as mineralocorticoid (MR) receptor modulators that may reduce oxidative stress in endothelium and hence improve vascular function, to their utility in potentially treating and/or preventing clinical conditions including cardiovascular and metabolic diseases such as hypertension, heart failure, chronic kidney disease, diabetic nephropathy, diabetes, disorders of the ocular vasculature, to methods for their potential therapeutic use, to pharmaceutical compositions containing them and to processes for preparing such compounds.

BACKGROUND

Aldosterone, a physiological mineralocorticoid, regulates sodium transport in epithelial tissues, particularly the distal nephron and colon. The response to aldosterone is mediated by a nuclear receptor, the mineralocorticoid receptor (MR; NR3C2) and involves non-genomic as well as genomic effects. The pivotal role of the MR in the mineralocorticoid response is demonstrated in MR null mice; these mice exhibit profound mineralocorticoid-unresponsive salt-wasting, which is inevitably fatal in the early neonatal period. Compromised mineralocorticoid action is associated with salt balance disorders and hyperaldosteroidism is associated with endothelial dysfunction and impaired vascular reactivity in patients with hypertension or congestive heart failure. MR antagonism is coupled to reduced oxidative stress in endothelium and hence improved vascular function.

High levels of circulating aldosterone are associated with endothelial dysfunction in hypertensives and patients with congestive heart failure, effects that are principally mediated by the mineralocorticoid receptor. Prolonged hyperaldosteronism is also associated with kidney fibrosis and eventually failure (*Trends Endocrinol Metab.* 2008, 19(3), 88-90). Blockade of MR in heart failure studies led to substantial reductions in mortality and morbidity, despite dosing being limited by MR mediated hyperkalemia (*N. Engl. J. Med.* 1999, 341(10), 709-17). Limited clinical trials have demonstrated beneficial effects of MR antagonists also in treatment of kidney disease including diabetic nephropathy (*Kidney International* 2011, 79, 1051). However, the risk for hyperkalemia is currently limiting the use of MR antagonists and particularly excludes diabetic patients. Novel, potent and selective MR antagonists should increase this therapeutic window between endothelial improvements and hyperkalemia of epithelial origin.

Non-steroidal MR antagonists disclosed in *Bioorg. Med. Chem. Lett.* 2005, 15, 2553 describe optimisation of 3,3-bisaryloxindoles as MR antagonists for use to treat congestive heart failure.

WO 2006/015259 relates to benzoxazinones as potent modulators of steroid hormone receptors including MR to treat a variety of disorders affecting the heart, kidney and the vasculature.

*Opin. Ther. Pat.* 2007, 17, 17 review the field of MR antagonists. The review also includes the two key steroidal MR antagonists eplerenone and spironolactone.

*Expert Opin. Ther. Patents* 2014, 24(2), 177 reviews the field of MR modulator in a patent review covering applications filed 2007-2012.

WO 2007/077961 relates to fused heterocyclic compounds as MR antagonists for treatment of hypertension, cardiac failure and the like.

DE 10 2007 009 494 disclose 4-aryl-1,4-dihydro-1,6-naphthyridin-3-carboxamides as MR antagonists for treatment of hypertension, heart failure, kidney disease and other conditions.

WO 2007/089034 disclose bicyclic compounds, such as N-(2,2-dimethyl-3-oxo-4-phenyl-3,4-dihydro-2H-1,4-benzoxazin-7-yl)methanesulfonamide, as binders to MR.

WO 2008/118319 relates to diphenylmethyl imidazoles with MR binding affinity for treatment of a range of conditions including cardiovascular and kidney disease.

WO 2008/53300 discloses MR antagonists for treatment of a range of conditions including cardiovascular and renal disorders.

WO 2008/126831 relates to atropisomers of N-(p-methylsulfonylphenyl)-5-(2-trifluoromethylphenyl)pyrrole-3-carboxamides as MR antagonists.

WO 2009/085584 relates to 6H-dibenzo[b,e]oxepine analogs as MR antagonists for treatment of physiological disorders like congestive heart failure, hypertension and diabetic nephropathy.

WO 2009/017190 disclose benzoxazine and chromene derivatives as MR antagonists useful as diuretics and for the prevention and/or treatment of hypertension, heart failure, myocardial infarction, angina pectoris, cardiac hypertrophy, myocardial fibrosis, vascular fibrosis, baroreceptor disorder, body fluid excess, arrhythmia, primary or secondary aldosteronism, Addison's disease, Cushing syndrome, or Bartter syndrome.

US 20100094000 relates to pyrazole derivatives as MR antagonists for use as hypertension, cardiac failure and the like.

WO 2010/098286 disclose (+)-1,4-dimethyl-N-[4-(methylsulfonyl)phenyl]-5-[2-(trifluoromethyl)phenyl]-1H-pyrrole-3-carboxam as an agent to treat diabetic nephropathy.

WO 2010/104721 relates to the specific use of 5-((E)-(3-fluorodibenzo[b,e]oxepin-11(6H)-ylidene)methyl)-1-((7R,8aR)-hexahydro-1H-pyrrolo[2,1-c][1,4]oxazin-7-yl)-1H-benzo[d]imidazol-2(3H)-one as a MR antagonists for prevention of diseases including congestive heart failure, diabetic nephropathy and chronic kidney disease.

WO 2010/116282 relates to dihydropyrazoles as MR antagonists for treatment of hypertension.

WO 2011/141848 relates to morpholine derivatives as MR antagonists and their use for treatment of a variety of conditions including diabetic nephropathy and endothelial dysfunction.

WO 2012/064631 discloses pyridyl ureas as antagonists of MR for treatment of e.g. heart failure.

WO 2012/008435 discloses diarylamide derivatives that inhibit MR for treatment of a range of diseases including kidney disease.

*J. Med. Chem.* 2011, 54, 8616 describes structure activity of benzoxazine-3-one derivatives as MR antagonists.

*J. Cardiovasc. Pharmacol.* 2012, 59(5), 458 describes SM-368229 as a MR antagonist with antihypertensive efficacy in rat with minimal effects on serum potassium levels.

*ChemMedChem* 2012, 7(8), 1385 reports the optimization of dihydropyridine to dihydronapthyridine analogs and identification of BAY 94-8862.

Mol. Cell. Endocrinol. 2012, 350, 310 reviews the pharmacology of MR antagonists and describe properties of BR-4628 and PF-3882845.

J. Med. Chem. 2012, 55, 7957 is a review in the field of non-steroidal MR antagonists.

Bioorg. Med. Chem. Lett. 2013, 23, 4388 reports on the exploration of oxazolidinone derivatives as potent MR antagonists.

Bioorg. Med. Chem. Lett. 2013, 23, 6239 reports on the exploration of arylsulfonamides as potent nonsteroidal MR antagonists.

Frontiers in pharmacology 2013, 4, 115 describe the effects of PF-03882845 in animal models of diabetic nephropathy and claim a reduced risk of hyperkalemia.

J. Med. Chem. 2014, 57(10), 4273 describe the efforts to improve nuclear hormone receptor selectivity of PF-03882845.

Despite the foregoing, there still exists a need for alternative/further improved agents for treatment of cardiovascular, inflammatory, metabolic and renal conditions, including heart failure, hypertension, chronic kidney disease, diabetic nephropathy, endothelial dysfunction, diabetes, disorders of the ocular vasculature, having, for example, the advantage that they may be more efficacious, be less toxic, be more selective, be more potent, produce fewer side effects, be more easily absorbed, and/or have a better pharmacokinetic profile (e.g. higher oral bioavailability and/or lower clearance), than compounds previously described.

SUMMARY

The object herein is to provide compounds that act as mineralocorticoid (MR) receptor modulators, their use as potential medicaments, pharmaceutical compositions containing them and synthetic routes to their production.

According to a first aspect, there is provided a compound of formula (I)

(I)

wherein
$R^1$ is selected from $CONH_2$ or $CONHCH_3$, and
$R^2$ is selected from H, F, Cl or Br,
or a pharmaceutically acceptable salt thereof.

The compounds of formula (I) are mineralocorticoid (MR) receptor modulators. Thus, the compounds of formula (I) may be used as a medicament, in particular for disorders, diseases or conditions responsive to modulation of MR, and more specifically cardiovascular, inflammatory, metabolic and renal conditions, including heart failure, hypertension, chronic kidney disease, diabetic nephropathy, endothelial dysfunction, diabetes, disorders of the ocular vasculature, in which modulation of MR plays a role.

In another aspect there is provided a pharmaceutical formulation comprising a therapeutically effective amount of a compound of formula (I), or a pharmaceutically acceptable salt of a compound of formula (I), and a pharmaceutically acceptable diluent, excipient and/or inert carrier.

In a further embodiment there is provided a pharmaceutical formulation comprising a compound of formula (I), or a pharmaceutically acceptable salt of a compound of formula (I), for use in the treatment of a condition where modulation of the mineralcorticoid receptor would be beneficial.

According to another aspect there is provided a compound of formula (I) or a pharmaceutically acceptable salt of a compound of formula (I) for use in therapy, especially in the prevention or treatment of chronic kidney disease in a mammal, particularly a human.

According to another aspect there is provided a compound of formula (I) or a pharmaceutically acceptable salt of a compound of formula (I) for use in therapy, especially in the prevention or treatment of cardiovascular and metabolic diseases in a mammal, particularly a human.

In a further embodiment there is provided a compound of formula (I) or a pharmaceutically acceptable salt of a compound of formula (I) for use in therapy, especially in the prevention or treatment of diabetic nephropathy in a mammal, particularly a human.

In a further embodiment there is provided a compound of formula (I) or a pharmaceutically acceptable salt of a compound of formula (I) for use in therapy, especially in the prevention or treatment of metabolic diseases, such as diabetes, in a mammal, particularly a human.

In still a further embodiment there is provided a compound of formula (I) or a pharmaceutically acceptable salt of a compound of formula (I) for use in therapy, especially in the prevention or treatment of heart failure in a mammal, particularly a human.

In still a further embodiment there is provided a compound of formula (I) or a pharmaceutically acceptable salt of a compound of formula (I) for use in therapy, especially in the prevention or treatment of hypertension in a mammal, particularly a human.

In still a further embodiment there is provided a compound of formula (I) or a pharmaceutically acceptable salt of a compound of formula (I) for use in therapy, especially in the prevention or treatment of endothelial dysfunction in a mammal, particularly a human.

In still a further embodiment there is provided a compound of formula (I) or a pharmaceutically acceptable salt of a compound of formula (I) for use in therapy, especially in the prevention or treatment of inflammatory diseases in a mammal, particularly a human.

According to another aspect there is provided a process for the preparation of compounds of formula (I) or pharmaceutically acceptable salts of compounds of formula (I), and the intermediates used in the preparation thereof.

The compounds of formula (I) herein exemplified, when tested in an MR binding assay, for example Test A described below, compete for aldosterone binding at concentrations below 50 µM, preferably with an $IC_{50}$ less than 50 µM. The compounds of formula (I) also display a promising pharmacological profiles by separating desired and undesired effects in vivo.

These and other embodiments are described in greater detail herein below, where further aspects will be apparent to one skilled in the art from reading this specification.

BRIEF DESCRIPTION OF THE DRAWINGS

FIG. 1 shows the X-ray powder diffraction pattern for Example 4a prepared according to Example 4a, Method B:

2-{(3S)-7-Fluoro-4-[(3-oxo-3,4-dihydro-2H-1,4-benzox-azin-6-yl)carbonyl]-3,4-dihydro-2H-1,4-benzoxazin-3-yl}-N-methylacetamide.

DETAILED DESCRIPTION

In this specification, the term "modulator" is used to describe a compound that exhibit varying receptor agonism and/or antagonism, either full agonism and/or antagonism, or partial agonism and/or antagonism.

For the avoidance of doubt it is to be understood that where in this specification a group is qualified by "defined above" the said group encompasses the first occurring and broadest definition as well as each and all of the other definitions for that group.

In one aspect, there are provided compounds of formula (I), or pharmaceutically acceptable salts thereof, wherein $R^1$ and $R^2$ are as defined in formula (I).

In one embodiment $R^1$ is $CONH_2$, and
$R^2$ is selected from H, F, Cl or Br.
In a further embodiment $R^1$ is $CONH_2$, and
$R^2$ is H.
In still a further embodiment $R^1$ is $CONH_2$, and
$R^2$ is F.
In still a further embodiment $R^1$ is $CONHCH_3$, and
$R^2$ is selected from H, F, Cl or Br.
In still a further embodiment $R^1$ is $CONHCH_3$, and
$R^2$ is H.
In still a further embodiment $R^1$ is $CONHCH_3$, and
$R^2$ is F.

In one embodiment, the compounds of formula (I) are single enantiomers with the configuration (S).

In another embodiment, the compounds of formula (I) are single enantiomers with the configuration (R).

In yet another embodiment, the compounds of formula (I) are racemates or racemic mixtures.

One or more of the above embodiments may be combined to provide further specific embodiments.

In one embodiment the compound of formula (I) is selected from:

2-{4-[(3-oxo-3,4-dihydro-2H-1,4-benzoxazin-6-yl)carbonyl]-3,4-dihydro-2H-1,4-benzoxazin-3-yl}acetamide,
N-methyl-2-{4-[(3-oxo-3,4-dihydro-2H-1,4-benzoxazin-6-yl)carbonyl]-3,4-dihydro-2H-1,4-benzoxazin-3-yl}acetamide,
N-methyl-2-{(3S)-4-[(3-oxo-3,4-dihydro-2H-1,4-benzoxazin-6-yl)carbonyl]-3,4-dihydro-2H-1,4-benzoxazin-3-yl}acetamide,
N-methyl-2-{(3R)-4-[(3-oxo-3,4-dihydro-2H-1,4-benzoxazin-6-yl)carbonyl]-3,4-dihydro-2H-1,4-benzoxazin-3-yl}acetamide,
2-{7-fluoro-4-[(3-oxo-3,4-dihydro-2H-1,4-benzoxazin-6-yl)carbonyl]-3,4-dihydro-2H-1,4-benzoxazin-3-yl}acetamide,
2-{(3S)-7-fluoro-4-[(3-oxo-3,4-dihydro-2H-1,4-benzoxazin-6-yl)carbonyl]-3,4-dihydro-2H-1,4-benzoxazin-3-yl}acetamide,
2-{(3R)-7-fluoro-4-[(3-oxo-3,4-dihydro-2H-1,4-benzoxazin-6-yl)carbonyl]-3,4-dihydro-2H-1,4-benzoxazin-3-yl}acetamide,
2-{7-fluoro-4-[(3-oxo-3,4-dihydro-2H-1,4-benzoxazin-6-yl)carbonyl]-3,4-dihydro-2H-1,4-benzoxazin-3-yl}-N-methylacetamide,
2-{(3S)-7-fluoro-4-[(3-oxo-3,4-dihydro-2H-1,4-benzoxazin-6-yl)carbonyl]-3,4-dihydro-2H-1,4-benzoxazin-3-yl}-N-methylacetamide,
2-{(3R)-7-fluoro-4-[(3-oxo-3,4-dihydro-2H-1,4-benzoxazin-6-yl)carbonyl]-3,4-dihydro-2H-1,4-benzoxazin-3-yl}-N-methylacetamide,
2-{7-chloro-4-[(3-oxo-3,4-dihydro-2H-1,4-benzoxazin-6-yl)carbonyl]-3,4-dihydro-2H-1,4-benzoxazin-3-yl}acetamide,
2-{(3S)-7-chloro-4-[(3-oxo-3,4-dihydro-2H-1,4-benzoxazin-6-yl)carbonyl]-3,4-dihydro-2H-1,4-benzoxazin-3-yl}acetamide,
2-{(3R)-7-chloro-4-[(3-oxo-3,4-dihydro-2H-1,4-benzoxazin-6-yl)carbonyl]-3,4-dihydro-2H-1,4-benzoxazin-3-yl}acetamide,
2-{7-chloro-4-[(3-oxo-3,4-dihydro-2H-1,4-benzoxazin-6-yl)carbonyl]-3,4-dihydro-2H-1,4-benzoxazin-3-yl}-N-methylacetamide,
2-{(3S)-7-chloro-4-[(3-oxo-3,4-dihydro-2H-1,4-benzoxazin-6-yl)carbonyl]-3,4-dihydro-2H-1,4-benzoxazin-3-yl}-N-methylacetamide,
2-{(3R)-7-chloro-4-[(3-oxo-3,4-dihydro-2H-1,4-benzoxazin-6-yl)carbonyl]-3,4-dihydro-2H-1,4-benzoxazin-3-yl}-N-methylacetamide,
2-{7-bromo-4-[(3-oxo-3,4-dihydro-2H-1,4-benzoxazin-6-yl)carbonyl]-3,4-dihydro-2H-1,4-benzoxazin-3-yl}acetamide,
2-{(3S)-7-bromo-4-[(3-oxo-3,4-dihydro-2H-1,4-benzoxazin-6-yl)carbonyl]-3,4-dihydro-2H-1,4-benzoxazin-3-yl}acetamide,
2-{(3R)-7-bromo-4-[(3-oxo-3,4-dihydro-2H-1,4-benzoxazin-6-yl)carbonyl]-3,4-dihydro-2H-1,4-benzoxazin-3-yl}acetamide,
2-{7-bromo-4-[(3-oxo-3,4-dihydro-2H-1,4-benzoxazin-6-yl)carbonyl]-3,4-dihydro-2H-1,4-benzoxazin-3-yl}-N-methylacetamide,
2-{(3S)-7-bromo-4-[(3-oxo-3,4-dihydro-2H-1,4-benzoxazin-6-yl)carbonyl]-3,4-dihydro-2H-1,4-benzoxazin-3-yl}-N-methylacetamide,
2-{(3R)-7-bromo-4-[(3-oxo-3,4-dihydro-2H-1,4-benzoxazin-6-yl)carbonyl]-3,4-dihydro-2H-1,4-benzoxazin-3-yl}-N-methylacetamide, and
pharmaceutically acceptable salts thereof.

It shall be noted that any one of these specific compounds may be disclaimed from any of the herein mentioned embodiments.

Another embodiment is a product obtainable by any of the processes or examples disclosed herein.

Pharmacological Properties

The compounds of formula (I) or pharmaceutically acceptable salts thereof are believed to be useful in the prevention or treatment of cardiovascular, inflammatory, metabolic and renal conditions, including but not limited to heart failure, hypertension, chronic kidney disease, diabetic nephropathy, endothelial dysfunction, diabetes, disorders of the ocular vasculature, in a mammal, particularly a human.

For the avoidance of doubt, as used herein, the term "treatment" includes therapeutic and/or prophylactic treatment.

When a compound or salt described herein is administered as therapy for treating a disorder, a "therapeutically effective amount" is an amount sufficient to reduce or completely alleviate symptoms or other detrimental effects of the disorder, cure the disorder, reverse, completely stop, or slow the progress of the disorder or reduce the risk of the disorder getting worse.

The compounds described herein are thus indicated both in the therapeutic and/or prophylactic treatment of these conditions.

The compounds described herein have the advantage that they may be more efficacious, be less toxic, be more selective, be more potent, produce fewer side effects, be more easily absorbed, and/or have a better pharmacokinetic profile (e.g. higher oral bioavailability and/or lower clearance), than compounds known in the prior art.

Combination Therapy

The compounds of formula (I), or a pharmaceutically acceptable salt thereof, may also be administered in conjunction with other compounds used for the treatment of the above conditions.

In another embodiment, provided is a combination therapy wherein a compound of formula (I), or a pharmaceutically acceptable salt thereof, and a second active ingredient are administered concurrently, sequentially or in admixture, for the treatment of one or more of the conditions listed above. Such a combination may be used in combination with one or more further active ingredients.

Compounds described herein may be of use in treating cardiovascular, metabolic and renal disease in combination with agents that are
- cardiac therapies,
- anti-hypertensives,
- diuretics,
- peripheral vasodilators,
- lipid modifying agents,
- anti-diabetic,
- anti-inflammatory,
- or anti-coagulant.

Examples of the above include, but are not restricted to, digitalis glycosides, anti-arrhythmics, calcium channel antagonists, ACE inhibitors, angiotensin receptor blockers, endothelin receptor blockers, β-blockers, thiazide diuretics, loop diuretics, cholesterol synthesis inhibitors such as statins (e.g. Rosuvastatin), cholesterol absorption inhibitors, cholesterylester transfer protein (CETP) inhibitors, anti-diabetic drugs such as insulin and analogues, GLP-1 analogues, sulphonamides, dipeptidyl peptidase 4 inhibitors, thiazolidinediones, SGLT-2 inhibitors, and anti-inflammatory drugs such as NSAID's and CCR2 antagonists, anti-coagulants such as heparins, thrombin inhibitors and inhibitors of factor Xa, platelet aggregation inhibitors and P2X7 antagonists.

When used in a combination therapy, it is contemplated that the compounds of formula (I) or pharmaceutically acceptable salts thereof and the other active ingredients may be administered in a single composition, completely separate compositions, or a combination thereof. It also is contemplated that the active ingredients may be administered concurrently, simultaneously, sequentially, or separately. The particular composition(s) and dosing frequency(ies) of the combination therapy will depend on a variety of factors, including, for example, the route of administration, the condition being treated, the species of the patient, any potential interactions between the active ingredients when combined into a single composition, any interactions between the active ingredients when they are administered to the animal patient, and various other factors known to physicians (in the context of human patients), veterinarians (in the context of non-human patients), and others skilled in the art.

Pharmaceutical Compositions

There is provided a method of treatment of a condition where modulation of MR is required, which method comprises administration of a therapeutically effective amount of a compound of formula (I) to a person suffering from, or susceptible to, such a condition.

The compounds of formula (I) will normally be administered via the oral, topical, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt thereof, in a pharmaceutically acceptable dosage form. Depending upon the disorder and patient to be treated and the route of administration, the compositions may be administered at varying doses. Conventional procedures for the selection and preparation of suitable pharmaceutical formulations are described in, for example, *Pharmaceuticals—The Science of Dosage Form Designs*, M. E. Aulton, Churchill Livingstone, 2nd Ed. 2002.

Suitable daily doses of the compounds of formula (I) in therapeutical treatment of humans are about 0.0001-100 mg/kg body weight, preferably 0.01-10 mg/kg body weight.

Oral formulations are preferred, particularly tablets or capsules which may be formulated by methods known to those skilled in the art to provide doses of the active compound in the range of 0.007 mg to 700 mg for example 1 mg, 3 mg, 5 mg, 10 mg, 25 mg, 50 mg, 100 mg and 250 mg.

The optimum dosage and frequency of administration will depend on the particular condition being treated and its severity; the species of the patient; the age, sex, size and weight, diet, and general physical condition of the particular patient; brain/body weight ratio; other medication the patient may be taking; the route of administration; the formulation; and various other factors known to physicians and others skilled in the art.

According to a further aspect there is thus provided a pharmaceutical formulation comprising a compound of formula (I), or pharmaceutically acceptable derivatives thereof, in admixture with a pharmaceutically acceptable adjuvant, diluent and/or carrier.

The compounds of formula (I) may be present in the pharmaceutical formulation in a concentration from 0.1 to 99.5%, such as from 0.5 to 95%, by weight of the total formulation.

Preparation of the Compounds

The compounds of formula (I) and their salts may be prepared according to the any one more of procedures of the following schemes and examples or any process known to be applicable to the preparation of chemically related compounds. Those skilled in the art will readily understand that known variations of the conditions and processes of the following preparative procedures may be used to prepare these compounds. Compounds of formula (I) may be may be prepared by the following processes.

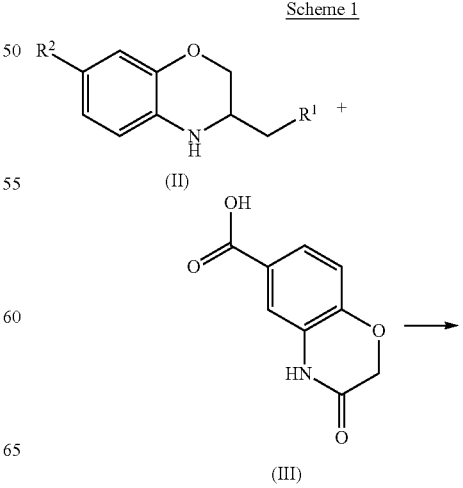

Scheme 1

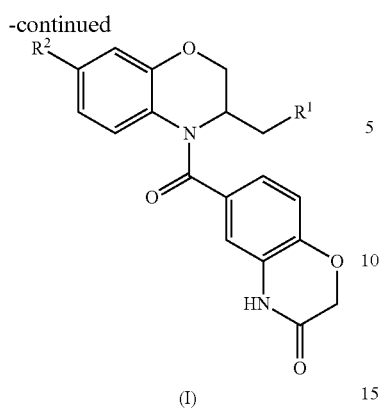

(I)

A compound of formula (I) wherein $R^1$ and $R^2$ are as defined above may be prepared by an amide coupling according to Scheme 1. One skilled in the art understands that there exists a multitude of suitable methods for this type of reaction. The reaction may e.g. be promoted by T3P or $PCl_3$. It may be performed in the presence of a base, e.g. TEA or DIPEA and is performed at elevated temperatures in an organic solvent, such as EtOAc, BuOAc, toluene or DMA. Protecting groups may be used for sensitive functional groups such as TBDPS for hydroxyl groups or MPM for sulfonamides.

One skilled in the art understands that there exists a multitude of suitable methods for transformation of $R^1$ and $R^2$ of formula (I). Some of these methods are given below.

A compound of formula (Ib) may be prepared by hydrolysis of an ester of formula (Ia) wherein $R^1$ is defined as for formula (I) and $R^3$ is an alkyl group. The reaction may be performed using a base such as LiOH or NaOH in a solvent like THF, MeOH and $H_2O$ or a mixture of such solvents at ambient or elevated temperature.

Carboxylic acids of formula (Ib), may be transformed into amides of formula (Ic), where $R^4$ is H or $C_{1-4}$ alkyl, by reacting them with the appropriate amine or amine salts using a suitable coupling reagent. One skilled in the art understands that there exists a multitude of suitable methods for this type of conversions using coupling agents. The reaction may be promoted by for example PyBOP, T3P, TBTU, acid halide forming or anhydride formation reagents. The reaction may be performed in the presence of a suitable base, e.g. TEA or NMM, and may conveniently be performed at ambient temperature in an organic solvent, such as EtOAc, THF, DMF or DCM or mixtures of such solvents. Alternatively an amide of formula (Ic) may be prepared from an ester of formula (Ia) by a reaction with the appropriate amine in a solvent such as MeOH, EtOH or mixtures of such solvents.

A compound of formula (II) could be made by the processes described below.

Scheme 2

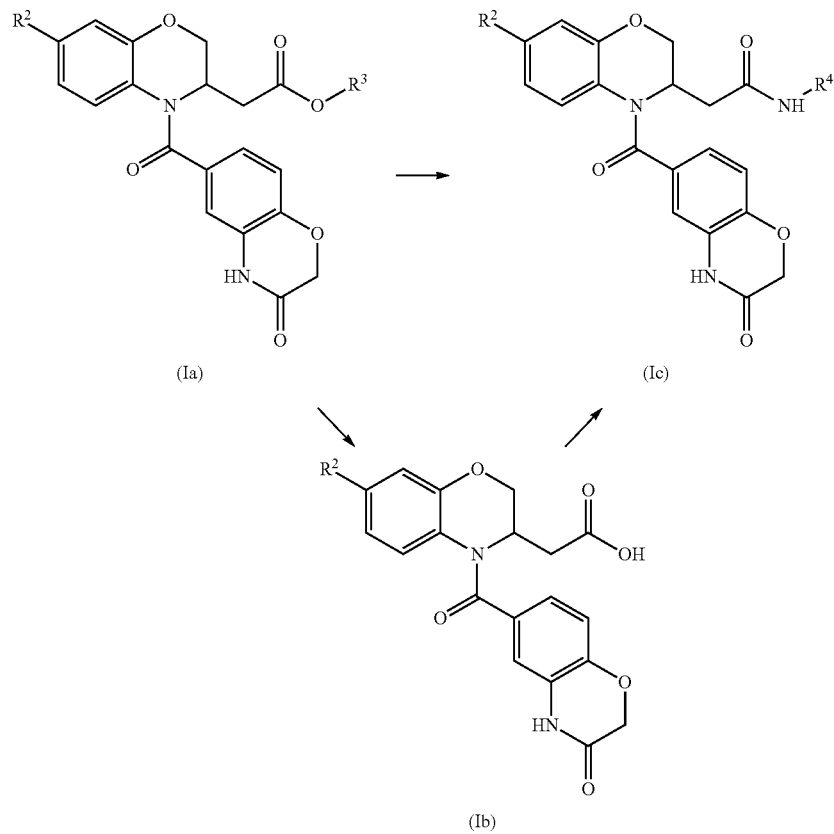

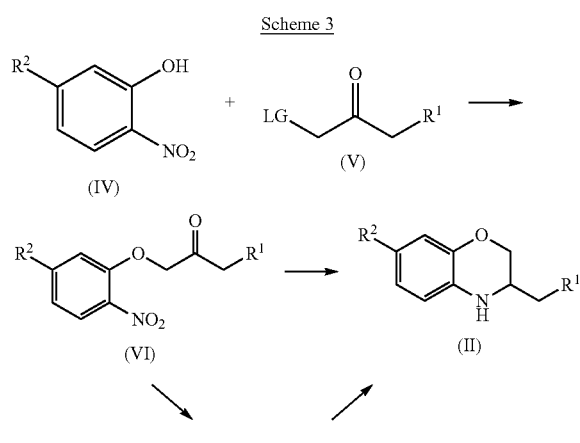

Scheme 3

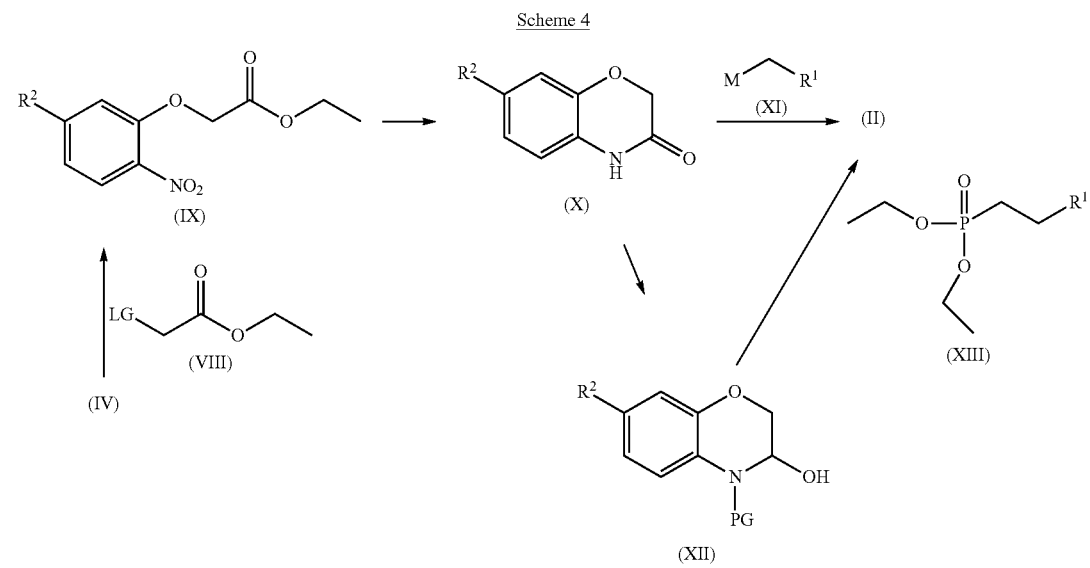

Scheme 4

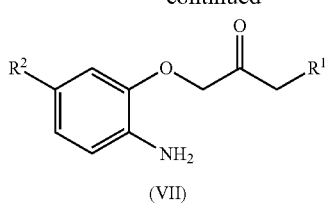

A compound of formula (II) may be prepared by reduction and cyclisation of a compound of formula (VI) wherein $R^1$ and $R^2$ are as defined in formula (I). One skilled in the art understands that there exists a multitude of suitable methods for this type of reaction. The reduction of a nitro group may for example be done by hydrogenation at 1-10 bar using a catalyst such as palladium on carbon in a solvent such as THF, MeOH or EtOH or mixtures of such solvents. An acid such as AcOH may be used.

The cyclisation of a compound of formula (VII) may be promoted by for example reductive amination using a reducing agent such as $NaBH(OAc)_3$. This may be done in a solvent such as 1,2-dichloroethane and AcOH at ambient temperature.

One skilled in the art understands that there exists a multitude of suitable methods for preparation of a compound of formula (VI). It may for example be prepared by alkylation of a compound of formula (IV) with a compound of formula (V) where LG is a suitable leaving group such as Br or Cl. The alkylation may be done using a range of bases for example $K_2CO_3$ in a solvent such as DMF or NMP at ambient or elevated temperature.

As shown in Scheme 4, a compound of formula (II) may be formed by reacting a compound of formula (X), wherein $R^1$ and $R^2$ are defined as in formula (I), with a organometallic compound of formula (XI), wherein $R^1$ is as defined in formula (I), followed by reduction of the intermediate hemiaminal.

The organometallic compound may be a Grignard reagent and the reaction may be done in a solvent such as THF at low to elevated temperature. The intermediate hemiaminal may be reduced using a suitable reducing agent such as $NaBH_4$.

Alternatively, a compound of formula (II) could be made a by a Horner-Wadsworth-Emmons type of reaction as shown in Scheme 4, using an hemiaminal of formula (XII), wherein PG is a suitable protecting group such as Boc, and a compound of formula (XIII) wherein, $R^2$ is as defined in formula (I) and $R^1$ is selected from, $CON(PG)_2$, $CON(PG)C_{1-4}$ alkyl, or $C(O)_2C_{1-4}$ alkyl, wherein PG is a suitable protecting group such as MPM. A base such as LiHMDS may be used, and the reaction may be done in a solvent such as THF at low to ambient temperature. The protecting group or groups are removed using a suitable method, to get a compound of formula (II).

A compound of formula (XII) could be made by protecting and reducing a compound of formula (X). A suitable protecting group such as Boc may be attached using methods known in the literature. The following reduction may be performed by a reducing agent such as $LiEt_3BH$ in a solvent such as THF at low temperature.

A compound of formula (X) may be formed by reduction and cyclisation of a compound of formula (IX). One skilled in the art understands that there exists a multitude of suitable methods for this type of reaction. The reduction may be performed for example with a reducing agent such as iron in a solvent such as AcOH at elevated temperature.

A person skilled in the art understands that there exists a multitude of suitable methods for preparation of a compound of formula (IX). It may for example be prepared as shown in Scheme 4 by alkylation of a compound of formula (IV) with a compound of formula (VIII) wherein LG is a suitable leaving group such as Br or Cl. The alkylation may be done using a base such as $K_2CO_3$ in a solvent such as DMF or NMP at ambient or elevated temperature.

As shown in Scheme 5, a compound of formula (IIb) may be prepared by reduction and cyclisation of a compound of formula (XV) wherein $R^1$ and $R^2$ are as defined in formula (I) and $R^3$ as in formula (Ia).

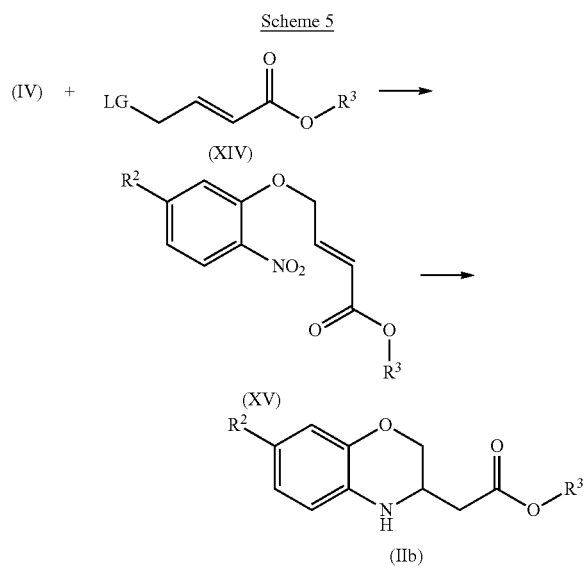

One skilled in the art understands that there exists a multitude of suitable methods for this type of reaction. The reduction may be performed for example with a reducing agent such as iron in a solvent such as AcOH at elevated temperature.

One skilled in the art understands that there exists a multitude of suitable methods for preparation of a compound of formula (XV). It can for example be prepared by alkylation of a compound of formula (IV) with a compound of formula (XIV) wherein $R^3$ is defined as in formula (Ia) and LG is a suitable leaving group such as Br or Cl. The alkylation may be done using an organic or inorganic base such as i-$PrEt_2N$, TEA, DBU or $K_2CO_3$ in a solvent such as THF, DMF or NMP at ambient or elevated temperature.

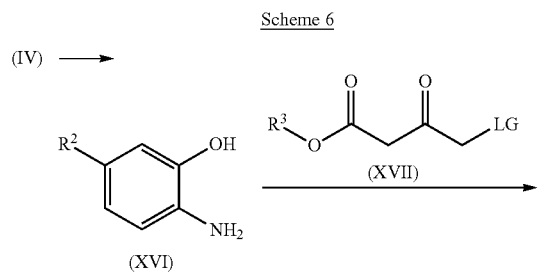

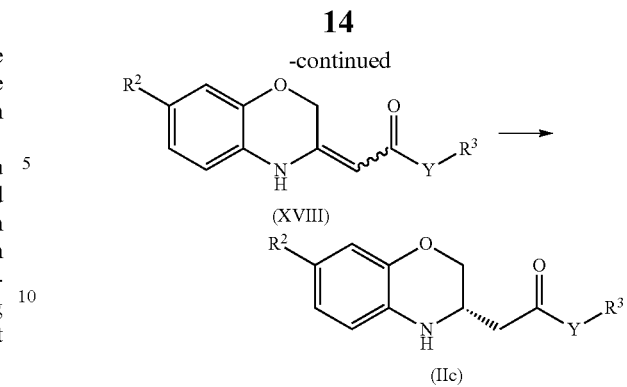

A compound of formula (IIc) may be formed by asymmetric reduction of a compound of formula (XVIII) wherein $R^1$ and $R^2$ are as defined in formula (I) and $R^3$ is defined as in formula (Ia) and Y=NH or O. The reduction may be achieved by hydrogenation at 5-50 bar at elevated temperature using ruthenium, rhodium or iridium chiral catalysts such as, but not limited to, [(R)-Binap RuCl(p-cym)]Cl, (S,S)[Ph-BPE Rh COD]$BF_4$, [Ir(COD)Cl]$_2$/(R)-Taniaphos (Ph), [Ir(COD)Cl]$_2$/(R)-PPhos, [Ir(COD)Cl]$_2$/(R)-XylPPhos, Rh(COD)$_2$ $BF_4$/(1R,1'R,2S,2'S) Duanphos in the presence of additives (Lewis or Bronsted acids, or organic bases, or iodine) as exemplified by the chiral catalyst (S,S)[Ph-BPE Rh COD] $BF_4$ and $Zn(OTf)_2$ in a solvent such as EtOH.

A compound of formula (XVIII) may be prepared by alkylation and cyclisation of a compound of formula (XVI) with a compound of formula (XVII), wherein LG is a leaving group such as chloro. This may be done using a base such as $K_2CO_3$ in a solvent such as NMP at elevated temperature or a base such as DIPEA, DBU or TEA in a solvent such as THF or EtOH at elevated temperature.

A compound of formula (XVI) may be prepared by reduction of a compound of formula (IV). One skilled in the art understands that there exists a multitude of suitable methods for this type of reaction for example by using $Na_2S_2O_4$ and a base such as $K_2CO_3$ in water.

The protection and deprotection of functional groups is described in *Protective Groups in Organic Synthesis*, 4th Ed, T. W. Greene and P. G. M. Wuts, Wiley-Interscience (2006) and *Protecting Groups*, 3rd Ed, P. J. Kocienski, Georg Thieme Verlag (2005).

A further embodiment encompasses pharmaceutically acceptable salts of the compounds of formula (I).

A salt of a compound of formula (I) may be advantageous due to one or more of its chemical or physical properties, such as stability in differing temperatures and humidities, or a desirable solubility in $H_2O$, oil, or other solvent. In some instances, a salt may be used to aid in the isolation or purification of the compound. In some embodiments (particularly where the salt is intended for administration to an animal, e.g. a human, or is a reagent for use in making a compound or salt intended for administration to an animal), the salt is pharmaceutically acceptable.

The term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

Where the compound is sufficiently acidic, pharmaceutically acceptable salts include, but are not limited to, an alkali metal salt, e.g. Na or K, an alkali earth metal salt, e.g. Ca or Mg, or an organic amine salt. Where the compound is sufficiently basic, pharmaceutically acceptable salts include, but are not limited to, inorganic or organic acid addition salts.

There may be more than one cation or anion depending on the number of charged functions and the valency of the cations or anions.

For reviews on suitable salts, see Berge et al., *J. Pharm. Sci.*, 1977, 66, 1-19 or *Handbook of Pharmaceutical Salts: Properties, selection and use*, P. H. Stahl, P. G. Vermuth, IUPAC, Wiley-VCH, 2002.

Where an acid or base co-former is a solid at rt and there is no or only partial proton transfer between the compound of formula (I) and such an acid or base co-former, a co-crystal of the co-former and compound of formula (I) may result rather than a salt. All such co-crystal forms of the compound of formula (I) are encompassed herein.

It is also to be understood that certain compounds of formula (I) may exist in solvated form, e.g. hydrates, including solvates of a pharmaceutically acceptable salt of a compound of formula (I).

In a further embodiment, certain compounds of formula (I) may exist as racemates and racemic mixtures, single enantiomers, individual diastereomers and diastereomeric mixtures. Certain compounds of formula (I) may also contain linkages (e.g. carbon-carbon bonds, carbon-nitrogen bonds such as amide bonds) wherein bond rotation is restricted about that particular linkage, e.g. restriction resulting from the presence of a ring bond or double bond. Stereoisomers may be separated using conventional techniques, e.g. chromatography or fractional crystallization, or the stereoisomers may be made by stereoselective synthesis.

In a further embodiment, the compounds of formula (I) encompass any isotopically-labelled (or "radio-labelled") derivatives of a compound of formula (I). Such a derivative is a derivative of a compound of formula (I) wherein one or more atoms are replaced by an atom having an atomic mass or mass number different from the atomic mass or mass number typically found in nature. Examples of radionuclides that may be incorporated include $^2$H (also written as "D" for deuterium).

In a further embodiment, the compounds of formula (I) may be administered in the form of a prodrug which is broken down in the human or animal body to give a compound of the formula (I). Examples of prodrugs include in vivo hydrolysable esters of a compound of the formula (I).

An in vivo hydrolysable (or cleavable) ester of a compound of the formula (I) that contains a carboxy or a hydroxy group is, for example, a pharmaceutically acceptable ester which is hydrolyzed in the human or animal body to produce the parent acid or alcohol. For examples of ester prodrugs derivatives, see: *Curr. Drug. Metab.* 2003, 4, 461.

Various other forms of prodrugs are known in the art. For examples of prodrug derivatives, see: *Nature Reviews Drug Discovery* 2008, 7, 255 and references cited therein.

EXAMPLES

The following examples are non-limiting examples. The Intermediates and Examples named below were named using ACD/Labs 2012. In the examples, HRMS spectral data were obtained using TOF-MS on a XEVO, LCTp system, from Waters, Agilent q-TOF 6530 or Bruker micrOTOF-Q.

Mass spectra were recorded on LC-MS system consisting of a waters zq, w3100 or sqd electrospray, using LC-agilent 1100, acquity hss or acquity beh LC systems.

$^1$H NMR measurements were performed on Jeol EX270 Eclipse, Bruker 400, 500 and 600 spectrometers, operating at $^1$H frequencies of 270, 400, 500 and 600 MHz respectively, at ambient temperature unless otherwise stated. Chemical shifts are given in ppm with the solvent as internal standard. Flash chromatography separations were performed using Biotage silica gel KP-Sil Snap Cartridge or Merck silica gel 60 (0.063-0.200 mm). Flash-chromatography was performed using either standard glass- or plastic-columns or on a Biotage SP1 or SP4 system.

Reactions performed in a microwave reactor were performed in a Biotage Initiator. Reactions performed in a H-Cube® were performed in a H-Cube® continous-flow hydrogenation reactor from ThalesNano, using a packed catalyst cartridge (CatCart®). Phase Separators used in the experimental are ISOLUTE Phase Separator Columns available from Biotage.

HPLC separations were performed on either on Gilson HPLC systems with gradient Trilution LC v.1.4 Software and UV/VIS detector 155, using either XBridge C18 column (10 μm 250×19 ID mm or 10 μm 250×50 ID mm) and a gradient of ACN in H$_2$O/ACN/NH$_3$ 95/5/0.2 buffer or Kromasil C8 column (10 μm 250×20 ID mm or 10 μm 250×50 ID mm) and a gradient of ACN in H$_2$O/ACN/FA 95/5/0.2 buffer. The flow for the smaller columns were 19 mL/min and for the bigger columns 100 mL/min. Alternatively Waters Fraction Lynx Purification System with MS triggered fraction collection was used, using Sunfire Prep C18 column (5 μm OBD, 19×150 mm) and a gradient of ACN in 0.1 mM FA (pH=3) or a Xbridge C18 column (5 μm OBD, 19×150 mm), and a gradient of ACN in 0.2% NH$_3$ (pH=10). Mass Spectra were recorded on either Waters ZQ single quadropole or Waters 3100 single quadropole both equipped with a pneumatically assisted electrospray interface. Alternatively Waters 100 SFC MS Directed Purification System with MS triggered fraction collection was used, using either Phenomenex Luna Hilic column (5 μm 250×30 ID mm) or Waters Viridis 2-EP column (5 μm 250×30 ID mm), either isocratic or using a gradient of MeOH/DEA 100/0.5 in CO$_2$, 120 bar at 40° C. Mass spectra were recorded on either Waters ZQ single quadropole or Waters 3100 single quadropole both equipped with a pneumatically assisted electrospray interface.

The X-ray diffraction analysis was performed according to standard methods, which may be found in, e.g., A. I. Kitaigorodsky (1973), *Molecular Crystals and Molecules*, Academic Press, New York; C. W. Bunn (1948), *Chemical Crystallography*, Clarendon Press, London; or H. P. Klug and L. E. Alexander (1974), *X-ray Diffraction Procedures*, John Wiley & Sons, Inc., New York. X-ray powder diffraction data was measured with Corundum as an internal reference. The X-ray powder diffraction (referred herein as XRPD) pattern was determined by mounting a sample on a zero background holder, single silicon crystal, and spreading out the sample into a thin layer. The powder X-ray diffraction was recorded with a Theta-Theta PANalytical X'Pert PRO (wavelength of X-rays 1.5418 Å nickel-filtered Cu radiation, Voltage 45 kV, filament emission 40 mA). Automatic variable divergence and anitscatter slits were used and the samples were rotated during measurement. Samples were scanned from 2-50° 2Theta using a 0.013° step width and a 44.37 s count time, together with a PIXCEL detector (active length 3.35° 2Theta). The X-ray powder diffraction (XRPD) pattern was obtained in Bragg-Brentano geometry. It is known that an X-ray powder diffraction pattern may be obtained which has one or more measurement errors depending on measurement conditions, such as equipment or machine used (Jenkins, R & Snyder, R. L. *Introduction to X-Ray Powder Diffractometry*

John Wiley & Sons 1996; Bunn, C. W. (1948), *Chemical Crystallography*, Clarendon Press, London; Klug, H. P. & Alexander, L. E. (1974), X-Ray Diffraction Procedures). Persons skilled in the art of X-ray powder diffraction will realize that the relative intensity of peaks can be affected by, for example, grains above 30 microns in size and non-unitary aspect ratios that may affect analysis of samples. Furthermore, it should be understood that intensities might fluctuate depending on experimental conditions and sample preparation (e.g. preferred orientation). The following definitions have been used for the relative intensity (%): 25-100%, vs (very strong); 10-25%, s (strong); 3-10%, m (medium); 1-3%, w (weak). The skilled person will also realize that the position of reflections can be affected by the precise height at which the sample sits in the diffractometer and the zero calibration of the diffractometer. The surface planarity of the sample may also have a small effect. Hence the diffraction pattern data presented are not to be taken as absolute values. Generally, a measurement error of a diffraction angle in an X-ray powder diffractogram may be approximately plus or minus 0.2° 2-theta, and such a degree of a measurement error should be taken into account when considering the X-ray powder diffraction data. Optical rotation was determined using a Perkin Elmer 341. The specific optical rotation is reported as $[\alpha]_D^{20}$ (solvent, c=1) wherein c=1 means 10 mg/mL and $[\alpha]_D^{20}$ means the optical rotation was determined at 20° C. using the Na line.

Several methods for determination of absolute configuration of chiral centres in small organic compounds are commonly used, including single crystal X-ray diffraction, NMR combined with chiral derivatisation, structural proof based on synthetic transformations, optical rotation and ECD. A more recent method is VCD that can be applied to most pharmaceuticals with reasonable size and flexibility. It relies on comparison of an experimental and a computed spectrum where the latter is an average of individual spectra of all low-energy conformers of the molecule according to the Boltzmann distribution. The method can be very fast since the spectra are acquired in solution. In cases where a single crystal is difficult and time consuming to obtain, it is particularly valuable. Many examples have been published, also applied to druglike compounds (*Appl. Spectrosc.* 2011, 65, 699, *Org. Biomol. Chem.*, 2012, 10, 4208, *Bioorg. Med. Chem. Lett.* 2013, 14, 4019, *J. Med. Chem.* 2014, 57, 477).

ABBREVIATIONS

The following abbreviations are used
ACN acetonitrile
AcOH acetic acid
aq. aq.
Boc tert-butyloxycarbonyl
br broad
BuOAc butyl acetate
BuLi butyl lithium
C Celsius
Calcd Calculated
CV column volume
d doublet
dd double of doublets
dba 1,5-diphenylpenta-1,4-dien-3-one
DBU 2,3,4,6,7,8,9,10-octahydropyrimido[1,2-a]azepine
DCM dichloromethane
DIBAL-H diisobutylaluminum hydride
DIPEA N,N-diisopropylethylamine
DIPHOS bis(diphenylphosphino)ethane
DMA N,N-dimethylacetamide
DMAP 4-(dimethylamino)pyridine
DMF N,N-dimethylformamide
DMHA HCl N,O-dimethylhydroxylamine hydrochloride
ECD electronic circular dichroism
ee enantiomeric excess
$Et_2O$ diethyl ether
DMSO dimethylsulphoxide
EtOAc ethyl acetate
EtOH ethanol
FA formic acid
$Fe(acac)_3$ tris((Z)-4-oxopent-2-en-2-yloxy)iron
g gram
h hour(s)
HPLC high-performance liquid chromatography
HRMS high resolution mass spectrometry
Hz Hertz
J coupling constant
LC liquid chromatography
LBD ligand binding domain
LiHMDS lithium bis(trimethylsilyl)amide
m multiplet
MCPBA 3-chlorobenzoperoxoic acid
MeOH methanol
MEA methyl amine
mg milligram
MHz megahertz
min minutes
mL milliliter
mmol millimole
MS mass spectra
MPM 4-methoxybenzyl
MTBE methyl tert-butyl ether
NMM N-methylmorpholine
NMP N-methylpyrrolidone
NMR nuclear magnetic resonance
OAc acetate
PE petroleum ether
$Pd_2(dba)_3$ tris(dibenzylideneacetone)dipalladium(0)
PyBOP (1H-benzo[d][1,2,3]triazol-1-yloxy)tripyrrolidin-1-ylphosphonium hexafluorophosphate(V)
q quartet
rt room temperature
s singlet
sat. saturated
T3P 1-propanephosphonic acid cyclic anhydride
t triplet
TBAF tetra-n-butyl ammonium fluoride
TBDPS t-butyldiphenylsilyl
TBPTA t-butylphenyl phosphinothioic acid
TBTU O-(Benzotriazol-1-yl)-N,N,N',N'-tetramethyluronium tetrafluoroborate
t-BuOH tert butyl alcohol
TFA trifluoroacetic acid
Tf trifluoromethanesulfonate
THF tetrahydrofuran
UV ultraviolet
VCD vibrational circular dichroism
Xant Phos 9,9-dimethyl-4,5-bis(diphenylphosphino)xanthene

PREPARATION OF INTERMEDIATES

Intermediate 1

Methyl (2E)-4-(2-nitrophenoxyl)but-2-enoate

Methyl-(2E)-4-bromobut-2-enoate (28.2 g, 0.158 mol) was added dropwise to 2-nitrophenol (20 g, 0.144 mol) and $K_2CO_3$ (29.8 g, 21.6 mol) in N,N-dimethylformamide (240 mL) at rt. The resulting mixture was stirred at rt for 2 h. The mixture was diluted with EtOAc (2.0 L) and washed with water (1.0 L), sat. aq. $Na_2CO_3$ (1.0 L) and brine (1.0 L). The organic phase was separated, dried over anhydrous $Na_2SO_4$, filtered and evaporated in vacuo to afford desired product (27.4 g, 80%) as a solid.

$^1$H NMR (300 MHz, DMSO-$d_6$) δ 3.69 (3H, s), 5.00 (2H, dd), 6.16 (1H, td), 7.04 (1H, td), 7.16 (1H, t), 7.36 (1H, d), 7.67 (1H, ddd), 7.93 (1H, dd).

MS m/z 238 (M+H)$^+$.

Intermediate 2

Methyl 3,4-dihydro-2H-1,4-benzoxazin-3-ylacetate

Iron dust (28.7 g, 0.51 mol) was added to Intermediate 1 (20.3 g, 0.086 mol) in acetic acid (304 mL) and water (30.4 mL) at rt. The resulting suspension solution was stirred at 80° C. for 2.5 h. The solvents were removed by evaporation in vacuo and 500 mL of EtOAc was added. The solids were filtered off and washed with EtOAc. The resulting solution was washed with water (500 mL). The aqueous phase was back extracted with EtOAc (2×500 mL). The combined organic layer was washed with sat. aq. $NaHCO_3$ (500 mL) and brine (500 mL). The combined organic layer was dried over anhydrous $Na_2SO_4$, filtered and concentrated by rotary evaporation under vacuum to afford the title compound (17.0 g, 96%) as yellow oil.

$^1$H NMR (400 MHz, DMSO-$d_6$) δ 2.47-2.59 (2H, m), 3.65 (3H, s), 3.69-3.74 (1H, m), 3.87 (1H, dd), 4.12 (1H, dd), 5.80 (1H, s), 6.49 (1H, ddd), 6.62 (1H, dd), 6.67-6.70 (2H, m).

MS m/z 208 (M+H)$^+$.

Intermediate 3

Methyl {4-[(3-oxo-3,4-dihydro-2H-1,4-benzoxazin-6-yl)carbonyl]-3,4-dihydro-2H-1,4-benzoxazin-3-yl}acetate T3P (50% solution in EtOAc, 61.5 g, 96.6 mmol) was added to 3-oxo-3,4-dihydro-2H-1,4-benzoxazine-6-carboxylic acid (10.3 g, 53.1 mmol), methyl 3,4-dihydro-2H-1,4-benzoxazin-3-ylacetate (Intermediate 2, 10.0 g, 48.3 mmol) and TEA (26.8 mL, 193.2 mmol) in EtOAc (125 mL) at rt. The resulting mixture was stirred at 75° C. for 16 h. The resulting solution was diluted with 350 mL of EtOAc and washed with sat. aq. $NaHCO_3$ solution (160 mL), 0.5 M HCl solution (160 mL) and brine (160 mL). The organic phase was dried over anhydrous $Na_2SO_4$, filtered and evaporated to afford crude product. The crude product was purified by re-crystallization from MeOH to afford the title compound (10.1 g, 55%) as a white solid.

MS m/z 383 (M+H)$^+$.

Intermediate 4

Ethyl {4-[(3-oxo-3,4-dihydro-2H-1,4-benzoxazin-6-yl)carbonyl]-3,4-dihydro-2H-1,4-benzoxazin-3-yl}acetate T3P (50% solution in EtOAc, 132.4 g, 0.208 mol) was added to 3-oxo-3,4-dihydro-2H-1,4-benzoxazine-6-carboxylic acid (22.1 g, 0.114 mol), ethyl-2-(3,4-dihydro-2H-1,4-benzoxazin-3-yl)acetate (23.0 g, 0.104 mol) and TEA (57.9 mL, 0.416 mol) in EtOAc (139 mL) at rt. The resulting mixture was stirred at 75° C. for 16 h. The resulting solution was diluted with 800 mL of EtOAc and washed with aq. sat. $NaHCO_3$ solution (300 mL), 0.5 M HCl solution (300 mL) and brine (300 mL). The organic phase was dried over anhydrous $Na_2SO_4$, filtered and evaporated to afford crude product. The crude product was purified by re-crystallization from MeOH to afford the title compound (14.5 g, 35%) as a white solid.

$^1$H NMR (300 MHz, DMSO-$d_6$) δ 1.17 (3H, t), 2.54 (2H, d), 4.01-4.12 (2H, m), 4.35 (2H, d), 4.65 (2H, s), 4.87 (1H, t), 6.71 (1H, dt), 6.92 (2H, d), 7.01 (2H, dt), 7.09 (1H, d), 10.81 (1H, brs).

MS m/z 397 (M+H)$^+$.

Intermediate 5

{4-[3-Oxo-3,4-dihydro-2H-1,4-benzoxazin-6-yl(carbonyl]-3,4-dihydro-2H-1,4-benzoxazin-3-yl}acetic acid NaOH (2 M, 0.39 mL, 0.78 mmol) was added to a slurry of ethyl {4-[(3-oxo-3,4-dihydro-2H-1,4-benzoxazin-6-yl)carbonyl]-3,4-dihydro-2H-1,4-benzoxazin-3-yl}acetate (Intermediate 4, 154 mg, 0.39 mmol) in a mixture of THF (2 mL)/water (2 mL)/EtOH (4 mL) giving a clear solution. The reaction mixture was stirred at rt overnight and then 1 M HCl (10 mL) was added and the mixture was extracted with EtOAc (3×10 mL). The combined organic layers were dried by passage through a phase separator and concentrated to dryness in vacuo giving the title compound (146 mg, 102%) as a white solid containing 3% EtOAc by weight.

$^1$H NMR (500 MHz, DMSO-$d_6$) δ 2.41-2.48 (m, 2H), 4.23-4.4 (m, 2H), 4.64 (s, 2H), 4.73-4.84 (m, 1H), 6.72 (t, 1H), 6.89-6.96 (m, 3H), 6.96-7.07 (m, 2H), 7.08 (d, 1H), 10.85 (s, 1H), 12.45 (br s, 1H).

HRMS m/z calculated for [$C_{19}H_{16}N_2O_6$+H$^+$]: 369.1086. found 369.1083.

Intermediate 6 tert-Butyl 7-fluoro-3-oxo-2,3-dihydro-4H-1,4-benzoxazine-4-carboxylate

7-Fluoro-2H-1,4-benzoxazin-3(4H)-one (7.0 g, 41.9 mmol) and di-tert-butyl dicarbonate (10.6 mL, 46.1 mmol) was dissolved in THF (130 mL). DMAP (0.512 g, 4.19 mmol) was added. The mixture was stirred at rt over night. EtOAc (200 mL) was added and the mixture was washed with HCl (0.5 M, 50 mL), sat. aq. $NaHCO_3$ (100 mL) and brine. The mixture was dried through a phase separator and evaporated to give the title compound (11.6 g, 104%) as a crude oil.

$^1$H NMR (500 MHz, CDCl$_3$) δ 1.62 (s, 9H), 4.57 (s, 2H), 6.73-6.82 (m, 2H), 7.19-7.26 (m, 1H).

Intermediate 7 tert-Butyl 7-fluoro-3-hydroxy-2,3-dihydro-4H-1,4-benzoxazine-4-carboxylate tert-Butyl 7-fluoro-3-oxo-2,3-dihydro-4H-1,4-benzoxazine-4-carboxylate (Intermediate 6, 2.22 g, 8.31 mmol) was dissolved in THF (20 mL) and cooled to −78° C. DIBAL-H (1 M in toluene, 10.8 mL, 10.8 mmol) was added at a rate to maintain the reaction temperature at below −70° C., and the reaction was thereafter stirred at −78° C. for 50 min. The cooling was removed and the reaction was quenched with $NH_4Cl$ (aq. sat. 10 mL). The mixture was allowed to reach rt. The reaction mixture was diluted with DCM and Rochelle's salt (30% aq., 100 mL) and extracted with DCM (2×100 mL). The organics were combined, washed with brine, dried over magnesium sulphate, filtered through a phase separator and concentrated to give the title compound (2.23 g, 100%) as a white solid.

$^1$H NMR (500 MHz, CDCl$_3$) δ 1.58 (s, 10H), 4.09 (dd, 1H), 4.29 (dd, 1H), 5.87-5.99 (m, 1H), 6.62-6.75 (m, 2H), 7.91 (s, 1H).

Intermediate 8 tert-Butyl 3-(2-ethoxy-2-oxoethyl)-7-fluoro-2,3-dihydro-4H-1,4-benzoxazine-4-carboxylate Step 1. At −78° C., lithium triethylhydroborate (1 M in THF, 52.1 mL, 52.1 mmol) was added dropwise to a cooled (dry ice/acetone) solution of tert-butyl 7-fluoro-3-oxo-2,3-dihydro-4H-1,4-benzoxazine-4-carboxylate (Intermediate 6, 11.6 g, 43.4 mmol) in THF (180 mL). The reaction mixture was stirred at −78° C. for 1.5 h. Saturated aq. Na$_2$CO$_3$ (55 mL) was added and the mixture was warmed to ca −20° C. H$_2$O$_2$ (30% in water, 55 mL) was added dropwise while maintaining low temp. The reaction mixture was stirred at −10° C. for 30 min. The mixture was filtered through celite, washing the plug with THF. Concentrated on rotary evaporator to ~150 mL. EtOAc (200 mL) was added. The mixture was washed with brine, dried through a phase separator and evaporated in vacuo. The crude hemiaminal (Intermediate 7) was obtained as a yellow solid and used without purification.

Step 2. At 0° C., LiHMDS (1 M in THF, 87 mL, 87 mmol) was added slowly (temp <5° C.) to ethyl 2-(diethoxyphosphoryl)acetate (17.4 mL, 87 mmol) in THF (60 mL). The reaction mixture was stirred for 15 min. The crude hemiaminal (Intermediate 7) from above was dissolved in THF (90 mL) and added dropwise to the cooled solution. The reaction mixture was stirred at 0° C. for 1 h. The ice bath was removed and the reaction was stirred at rt for 5 h. Additional LiHMDS (1 M in THF, 21.7 mL, 21.7 mmol) was added and the reaction was stirred at rt over night. Additional Horner-Wadsworth-Emmons-reagent was prepared by mixing ethyl 2-(diethoxyphosphoryl)acetate (4.34 mL, 21.7 mmol) and LiHMDS (1 M in THF, 21.7 mL, 21.7 mmol) in THF (20 mL) while cooling on ice. Stirred on ice for 30 min. The solution was carefully added to the reaction mixture and stirring continued at rt for 4 h. EtOAc (300 mL) was added, washed with sat. aq. Na$_2$CO$_3$ (250 mL), sat. aq. NaHCO$_3$ (100 mL), HCl (0.5 M, 100 mL) and brine. The organic layer was separated and dried over Na$_2$SO$_4$ and evaporated after filtration. The residue was purified by automated flash chromatography on a Biotage® KP-SIL 340 g column. A gradient from 5% to 25% of EtOAc in heptane over 5 CV was used as mobile phase. The title compound (6.69 g, yield 45.4%) was collected using wavelength 250/285 nm for detection.

$^1$H NMR (500 MHz, CDCl$_3$) δ 1.26 (t, 3H), 1.54 (s, 9H), 2.47 (dd, 1H), 2.57 (dd, 1H), 4.08-4.21 (m, 3H), 4.37 (d, 1H), 5.01 (s, 1H), 6.56-6.69 (m, 2H), 7.79 (s, 1H). MS m/z 340.2 (M+H)$^+$.

Intermediate 9

Ethyl (2E)-4-(5-fluoro-2-nitrophenoxy)but-2-enoate

A mixture of 3-fluoro-6-nitrophenol (200 g, 1.27 mol), anhydrous K$_2$CO$_3$ (202 g, 1.46 mol) and NMP (1.2 L) under nitrogen atmosphere was stirred at 25° C. for 30 min. Ethyl 4-bromocrotonate (80% tech., 252 mL, 1464 mmol) was added during 2-3 min to the obtained red suspension and the resulting mixture was stirred over night at ambient temperature. The yellowish suspension was then poured into ice-water (8.0 L) under stirring. After stirring for 1 h the solids were filtered off, washed with water (5×1.0 L), heptane (4×0.50 L) and then dried over night at 50° C. in vacuo affording the title compound (332 g, 1.20 mmol, 98% w/w, 95% yield).

$^1$H NMR (400 MHz, CDCl$_3$) δ 1.31 (t, 3H), 4.23 (q, 2H), 4.82 (dd, 2H), 6.31 (dt, 1H), 6.71-6.82 (m, 2H), 7.04 (dt, 1H), 8.00 (dd, 1H).

Intermediate 10

Ethyl (7-fluoro-3,4-dihydro-2H-1,4-benzoxazin-3-yl)acetate

Ethyl (2E)-4-(5-fluoro-2-nitrophenoxy)but-2-enoate (Intermediate 9, 310 g, 1.09 mol) dissolved in AcOH (1.4 L) was added dropwise during one h to a slurry of iron powder (325 mesh, 305 g, 5.47 mol) in AcOH (0.90 L) at 60° C. under nitrogen atmosphere. The temperature was kept at 60-75° C. during the addition. Upon complete addition the resulting mixture was stirred at 70° C. for 30 min before it was cooled to rt. The solids were filtered off and washed with AcOH (2.5 L). The filtrate was concentrated to dryness and the residue was dissolved in EtOAc (2.0 L). The solution was washed with citric acid (aq., 10% w/w, 2×1.0 L), Na$_2$CO$_3$ (10% w/w, 500 mL) and water (1.5 L). The solution was then concentrated to dryness and the obtained residue was dissolved in i-PrOAc (500 mL). Concentration to dryness once again yielded a residue which was purified by column chromatography on silica using heptane/EtOAc (4:1) as eluent. The title compound (236 g, 0.986 mol, 98% w/w, 88% yield) was obtained as an oil.

$^1$H NMR (400 MHz, CDCl$_3$) δ 1.29 (t, 3H), 2.52 (d, 2H), 3.80 (qd, 1H), 3.94 (dd, 1H), 4.20 (dt, 3H), 4.33 (s, 1H), 6.47-6.59 (m, 3H).

Intermediate 10a and 10b, Method A

Ethyl [(3S or 3R)-7-fluoro-3,4-dihydro-2H-1,4-benzoxazin-3-yl]acetate

The two enantiomers of ethyl (7-fluoro-3,4-dihydro-2H-1,4-benzoxazin-3-yl)acetate (433 g, 1.76 mol) were separated on a NovaSep SFC fitted with a ChiralPak AD column (250× 110 mm, 20 μm particle size) and EtOH/TEA 100/0.1 as eluent.

Intermediate 10a, Method A

Ethyl [(3S)-7-fluoro-3,4-dihydro-2H-1,4-benzoxazin-3-yl]acetate

The first eluted compound was collected and evaporated to yield ISOMER 1 of the title compound [(201 g, 0.848 mol, 99.6% ee by chiral HPLC (Chiralpak AD 250×110 mm 20 μm, eluting with EtOH/TEA 100/0.1 at rt, detection at 270 nm) and >99.5% ee by F NMR with chiral shift reagent ((R)-TBPPTA), 48.3% yield, $[α]_D^{20}$=−40.4° (c 1.0, ACN)].

$^1$H NMR (400 MHz, CDCl$_3$) δ 1.29 (t, 3H), 2.52 (d, 2H), 3.81 (qd, 1H), 3.95 (dd, 1H), 4.13-4.25 (m, 3H), 4.33 (s, 1H), 6.46-6.59 (m, 3H).

Intermediate 10b, Method A

Ethyl [(3R)-7-fluoro-3,4-dihydro-2H-1,4-benzoxazin-3-yl]acetate

The second eluted compound was collected and evaporated to yield ISOMER 2 of the title compound [(192 g, 0.802 mol, 96.6% ee by chiral HPLC (Chiralpak AD 250×110 mm 20 µm, eluting with EtOH/TEA 100/0.1 at rt, detection at 270 nm) and, 96.3% ee by F NMR with chiral shift reagent ((R)-TBPPTA), 45.7% yield, $[\alpha]_D^{20}$=+44.5° (c 1.0, ACN)].

$^1$H NMR (400 MHz, CDCl$_3$) δ 1.29 (t, 3H), 2.52 (d, 2H), 3.81 (qd, 1H), 3.95 (dd, 1H), 4.14-4.25 (m, 3H), 4.33 (s, 1H), 6.46-6.59 (m, 3H).

Intermediate 10a, Method B

Ethyl [(3S)-7-fluoro-3,4-dihydro-2H-1,4-benzoxazin-3-yl]acetate (S,S) [Ph-BPE Rh COD]BF$_4$ (0.10 mol %, 1.7 g) was charged to the hydrogenator followed by Zn(OTf)$_2$ (4.0 mol %, 30.6 g) and ethanol (70 mL). The hydrogenator was then purged with nitrogen (3 times). Ethyl (2Z)-(7-fluoro-2H-1,4-benzoxazin-3(4H)-ylidene)acetate (Intermediate 11, 500 g) was dissolved in ethanol (3930 mL) at 45° C. The resulting solution was degassed (3× vacuum followed by nitrogen) and charged to the hydrogenator (N$_2$ transfer) using degassed ethanol (1000 mL) as a line rinse. The hydrogenator was purged with 5 bar nitrogen (3 times) then 10 bar hydrogen (3 times). The reaction was then heated at 50° C./10 bar hydrogen for 18 h (stirrer 1000 rpm) after which HPLC indicated the reaction was complete. After cooling to room temperature, the solvent was removed in vacuo and the residue combined with the crude product from three previous 500 g scale reactions. The combined residue was dissolved in EtOAc (400 mL). Heptane (1600 mL) was added and the solution was loaded onto a pad of silica (2 Kg) and eluted with 10%-30% EtOAc. The product fractions were stripped to give the desired product as a brown oil (2052 g, quant.). $^1$H NMR confirmed the identity of the product and chiral HPLC indicated an ee of 99.03%.

$^1$H NMR (270 MHz, CDCl$_3$) δ 1.26 (t, 3H), 2.49 (d, 2H), 3.78 (qd, 1H), 3.91 (dd, 1H), 4.11-4.22 (m, 3H), 4.32 (br s, 1H), 6.43-6.56 (m, 3H).

Catalyst Screening for the Conversion of ethyl (2Z)-(7-fluoro-2H-1,4-benzoxazin-3(4H)-ylidene)acetate (Intermediate 11) into ethyl [(3S)-7-fluoro-3,4-dihydro-2H-1,4-benzoxazin-3-yl]acetate (Intermediate 10a)

(a) Rhodium Catalysts:
Generalised Procedure in 48 Well Plate:

A solution of the ligand (0.00044 mmol) in DCM (100 µL) was charged to a 2 mL well, followed by the metal source (0.0004 mmol) in DCM (100 µL). The mixture was stirred for 10 min then evaporated. A solution of ethyl (2Z)-(7-fluoro-2H-1,4-benzoxazin-3(4H)-ylidene)acetate (Intermediate 11, 0.02 mmol) and zinc triflate (0.0008 mmol) in ethanol (667 µL) was then added to the well and the resulting mixture was hydrogenated at 155 psi pressure and 50° C. for 16 h then analysed by hplc for conversion to ethyl [(3S)-7-fluoro-3,4-dihydro-2H-1,4-benzoxazin-3-yl]acetate (Intermediate 10a) and enantiomeric purity of the product.

| Metal source | ligand | Conversion (%) | e.e. (%)* |
|---|---|---|---|
| [Rh(cod)2]BF4 | (R)-BINAP | 95.49 | 94.97 |
| [Rh(cod)2]BF4 | (R)-Tolyl-BINAP | 100 | 96.43 |
| [Rh(cod)2]BF4 | S-BINAPINE | 100 | −96.35 |
| [Rh(cod)2]BF4 | S,S,R,T-Tangphos | 100 | 97.90 |
| [Rh(cod)2]BF4 | (R,R)-BenzP* | 100 | 97.56 |
| [Rh(cod)2]OTf | (R)-Tolyl-BINAP | 100 | 95.03 |
| [Rh(cod)2]OTf | S,S,R,T-Tangphos | 100 | 98.36 |
| [Rh(cod)2]OTf | S-BINAPINE | 100 | −96.17 |
| [Rh(cod)2]OTf | R,R,S,S-Duanphos | 100 | 96.62 |
| [Rh(cod)2]OTf | R,R-QuinoxP* | 100 | 95.56 |
| [Rh(cod)2]OTf | (R,R)-BenzP* | 100 | 97.87 |

*a minus value for e.e. indicates that the (R)-enantiomer of the product was the major component
(R,R)-BenzP* = (R,R)-(+)-1,2-Bis(t-butylmethylphosphino)benzene CAS 919778-41-9
R,R-QuinoxP* = (R,R)-2,3-Bis(tert-butylmethylphosphino)quinoxaline CAS 866081-62-1
S-BINAPINE = (3S,3'S,4S,4'S,11bS,11'bS)-(+)-4,4'-Di-t-butyl-4,4',5,5'-tetrahydro-3,3'-bi-3H-dinaphtho[2,1-c: 1',2'-e]phosphepin CAS 528854-26-4

(b) Ruthenium Catalysts
Generalised Procedure in 48 Well Plate Using Separate Metal Source and Ligand:

A solution of the ligand (0.00044 mmol) in DMF (100 µL) was charged to a 2 mL well, followed by the metal source (0.0002 mmol) in DMF (100 µL). The mixture was stirred for 30 min at 100° C. then evaporated. A solution of ethyl (2Z)-(7-fluoro-2H-1,4-benzoxazin-3(4H)-ylidene)acetate (Intermediate 11, 0.02 mmol) and 85% w/w aqueous phosphoric acid (0.02 mmol) in ethanol (667 µL) was then added to the well and the resulting mixture was hydrogenated at 95-99 psi pressure and 80-85° C. for 16 h then analysed by hplc for conversion to ethyl [(3S)-7-fluoro-3,4-dihydro-2H-1,4-benzoxazin-3-yl]acetate (Intermediate 10a) and enantiomeric purity of the product.

| Metal source | ligand | Conversion (%) | e.e. (%)* |
|---|---|---|---|
| (benzene)RuCl2 dimer | R-Xyl-BINAP | 95.31 | 94.82 |
| (benzene)RuCl2 dimer | (R)-(+)-DM-SEGPHOS | 100 | 94.55 |
| (benzene)RuCl2 dimer | R-Xyl-P-Phos | 100 | −94.93 |
| (p-cymene)RuCl2 dimer | R-Xyl-BINAP | 94.52 | 94.67 |

Generalised Procedure in 48 Well Plate Using Pre-Formed Catalyst and Varying Amount of Additive:

The pre-formed catalyst (0.00044 mmol) in DMF (200 µL) was charged to a 2 mL well.

The mixture was stirred to dissolve then evaporated. A solution of ethyl (2Z)-(7-fluoro-2H-1,4-benzoxazin-3(4H)-ylidene)acetate (Intermediate 11, 0.02 mmol) and 85% w/w aqueous phosphoric acid (varying amounts) in ethanol (667 µL) was then added to the well and the resulting mixture was hydrogenated at 95-99 psi pressure and 80-85° C. for 16 h then analysed by h.p.l.c. for conversion to ethyl [(3S)-7-fluoro-3,4-dihydro-2H-1,4-benzoxazin-3-yl]acetate (Intermediate 10a) and enantiomeric purity of the product.

| Pre-formed catalyst | H3PO4 (e.q.) | Conversion (%) | e.e. (%)* |
|---|---|---|---|
| [RuCl(p-cymene)((R)-binap)]Cl | 2 | 93.92 | 95.23 |
| [RuCl(p-cymene)((R)-binap)]Cl | 5 | 98.03 | 96.01 |
| [RuCl(p-cymene)((R)-xylbinap}]Cl | 1 | 95.16 | 95.08 |
| [RuCl(p-cymene)((R)-xylbinap}]Cl | 2 | 96.85 | 96.35 |

(c) Iridium Catalysts:

Generalised Procedure in 48 Well Plate:

A solution of the ligand (0.00044 mmol) in DCM (100 μL) was charged to a 2 mL well, followed by the metal source (0.0004 mmol for [Ir(COD)2]BF4; 0.0002 mmol for [Ir(COD)Cl]2) in DCM (100 μL). The mixture was stirred for 10 min then evaporated. A solution of ethyl (2Z)-(7-fluoro-2H-1,4-benzoxazin-3(4H)-ylidene)acetate (Intermediate 11, 0.02 mmol) and iodine (0.01 mmol) in toluene (667 μL) was then added to the well and the resulting mixture was hydrogenated at 10 bar pressure and 30° C. for 16 h then analysed by h.p.l.c. for conversion to ethyl [(3S)-7-fluoro-3,4-dihydro-2H-1,4-benzoxazin-3-yl]acetate (Intermediate 10a) and enantiomeric purity of the product.

| Metal source | ligand | Conversion (%) | e.e. (%)* |
|---|---|---|---|
| [Ir(COD)Cl]2 | (R)-Cl—MeO-BIPHEP | 100 | −95.40 |
| [Ir(COD)Cl]2 | R-C3-Tunephos | 100 | 96.08 |
| [Ir(COD)2]BF4 | (R)-Cl—MeO-BIPHEP | 100 | −94.55 |
| [Ir(COD)2]BF4 | R-C3-Tunephos | 100 | 95.74 |

Intermediate 10c

Ethyl [(3S)-7-fluoro-3,4-dihydro-2H-1,4-benzoxazin-3-yl]acetate, 2-naphthalenesulfonate salt Ethyl (2Z)-(7-fluoro-2H-1,4-benzoxazin-3(4H)-ylidene)acetate (Intermediate 11, 20.0 g, 84 mmol) was charged to a 250 mL glass autoclave. The autoclave was pressurized 5 times to 3.5 bar with nitrogen and then 160 mL absolute ethanol (deoxygenated by 10 minutes nitrogen bubbling) was added via syringe against a flow of nitrogen. Tj was set to 45° C. and the stirrer rate to 800 rpm and the reactor was pressurized to 3.5 bar with nitrogen 3 times.

A solution of Rh(S)-Ph-BPE(cod)BF4 (64 mg, 0.0796 mmol, 0.0009 eq) and Zn(OTf)$_2$ (1.25 g, 3.4 mmol, 0.040 eq) in 20 mL of degassed ethanol was charged via syringe against a flow of nitrogen. The autoclave was pressurized 3 times to 3.5 bar with nitrogen and then twice to 3 bar with hydrogen before pressurizing to 9.5 bar with hydrogen. Tj was set to 50° C. The gas uptake ceased after 5 h and a sample taken after 14 h indicated 100% conversion and 99.5% ee. The reaction solution was transferred to a flask and weighed (141.5 g).

20.56 g of the reaction mixture was withdrawn (corresponding to 2.92 g, 12.2 mmol product) and 2-naphthalenesulfonic acid (monohydrate) (2.85 g, 12.6 mmol) was added. A compact precipitate was formed and the mixture was heated to 80° C. to give a clear dark brown solution. Cooling to 20° C., filtering and rinsing with 5 mL ethanol, gave, after drying in vacuum at 40° C., Ethyl 2-[(3S)-7-fluoro-3,4-dihydro-2H-1,4-benzoxazin-3-yl]acetate, 2-naphthalenesulfonate as a white solid (4.21 g, 77% yield—assay corrected).

$^1$H NMR (spectrum recorded in DMSO-$d_6$ on a Bruker Avance spectrometer operating at 500 MHz) δ(ppm): 8.70 (bs, 2H), 8.16 (bs, 1H), 8.00-7.95 (m, 1H), 7.93-7.88 (m, 1H), 7.87 (d, 1H, J=8.6 Hz), 7.72 (dd, 1H, J=8.6 Hz J=1.7 Hz), 7.55-7.50 (m, 2H), 6.69 (dd, 1H, J=8.7 Hz J=5.9 Hz), 6.64-6.55 (m, 2H), 4.18 (dd, 1H, J=10.8 Hz J=2.9 Hz), 4.1 (q, 2H, J=7.1 Hz), 3.90 (dd, 1H, J=10.8 Hz J=6.4 Hz), 3.71 (ddd, 1H, J=6.7 Hz J=6.7 Hz J=2.8 Hz), 2.56 (dd, 1H, J=16.2 Hz J=6.4 Hz), 2.49 (dd, 1H, J=16.2 Hz J=6.9 Hz), 1.19 (t, 3H, J=7.1 Hz).

Intermediate 11, Method A

Ethyl (2Z)-(7-fluoro-2H-1,4-benzoxazin-3(4H)-ylidene)acetate

Ethyl 4-chloroacetoacetate (1 eq., 521.6 mL) was added to a solution of 2-amino-5-fluoro-phenol (488.2 g) in THF (4883 mL). The reaction was heated to 50° C. and DIPEA (1 eq., 664.6 mL) was added dropwise over 1 h at 50-60° C. The resulting reaction mixture was heated at 50° C. for 6 h. $^1$H NMR analysis confirmed the reaction was complete. The reaction was cooled to rt and partitioned with MTBE (4883 mL)/water (4883 mL). The phases were separated and the aq. extracted with MTBE (2×1220 mL). The combined organics were washed with 20 wt % brine (3×1220 mL), dried over MgSO$_4$, filtered and stripped to yield the crude product as a dark brown solid. The crude material was combined with the crude product from two further reactions (both 488.3 g scale) and purified via a silica pad; the material was taken up in DCM (600 mL) and MTBE (2810 mL). Silica (3 kg) was added followed by EtOAc (141 mL) and heptane (2669 mL). The resulting slurry was poured onto a pad of silica (9 kg) and eluted with 5% EtOAc in heptane (11×10 L fractions). The product fractions were stripped to give an orange solid (2291 g). The product was combined with crude product from another reaction (120 g input) and re-purified via a silica pad, dissolved in DCM (2.2 L) and loaded onto silica (12 kg). Eluted with 5% EtOAc in heptane (17×10 L). Product fractions were stripped to give a yellow solid (2290 g). This solid was taken up in heptane (6870 mL) and heated to dissolve (60° C.). The solution was cooled to 40° C. and seeded with pure product from an intermediate scale reaction then cooled to −5° C. and stirred for 1 h. The resulting solid was filtered, washed with cold heptane (2×1 L) and solvents were removed in vacuo. Further drying in a vacuum oven at 40° C. yielded the desired title compound as a cream-yellow solid (2140 g, calculated 72% yield from the combined input of 2-amino-5-fluoro-phenol).

$^1$H NMR (Jeol EX270 Eclipse, 270 MHz, CDCl$_3$) δ ppm 1.27 (t, 3H), 4.15 (q, 2H), 4.54 (s, 2H), 4.64 (s, 1H), 6.58-6.67 (m, 2H), 6.70-6.78 (m, 1H), 10.10 (br. s, 1H).

Intermediate 11, Method B

Ethyl (2Z)-(7-fluoro-2H-1,4-benzoxazin-3(4H)-ylidene)acetate

5-Fluoro-2-nitrophenol (250 g, 1.591 mol) was charged to a 5 L stainless steel autoclave. 7.5 g of 10% Pd/C (Escat 1931) was charged followed by 1.50 L methanol. The temperature was set to 20° C. and the reactor was pressurized 4 times to 2 bar with nitrogen and then 2 bar hydrogen pressure was applied and the stirrer rate set to 600 rpm. The reaction was left for 15 hours (the gas uptake had ceased after 200 minutes) whereafter the hydrogen pressure was released and the autoclave was purged with nitrogen. The reaction mixture was filtered through a K200 filter and the collected catalyst on the filter rinsed with methanol (250 mL).

The reaction mixture was transferred to a reactor and ethyl-4-chloroacetoacetate (385 g, 2.368 mol, 1.5 eq) was added followed by addition of methanol (250 mL) for rinsing the line and Tj was set to 40° C. The mixture was stirred for 30 minutes at which point Ti was 35° C. DIPEA (205.6 g, 1.594 mol, 1.002 equivalents) was charged over 45 min. The reaction was stirred for an additional 10 minutes at which point $^{19}$F NMR analysis showed 90% product. Tj was set to 30° C. and after 10 min Ti was 32° C. Ethyl (2Z)-(7-fluoro-2H-1,4- benzoxazin-3(4H)-ylidene)acetate seed (20 mg, prepared according to Example 11, Method A) was added and the mixture stirred for an additional 45 min. Water (500 mL) was charged over 1 h and then Tbath was set to 20° C. After an additional 1.5 hours the mixture was filtered. The cake was washed with 75% aqueous methanol (750 mL) and dried under vacuum at 40° C. to give the title product (261 g; 68% assay corrected yield).

Intermediate 12

(2Z)-2-(7-Fluoro-2H-1,4-benzoxazin-3(4H)-ylidene)-N-methylacetamide

A mixture of ethyl (2Z)-(7-fluoro-2H-1,4-benzoxazin-3 (4H)-ylidene)acetate (Intermediate 11, 2.0 g; 8.4 mmol), MeOH (6.0 mL) and methylamine (7.3 mL of a 40 wt % aq. Solution, 84.3 mmol) was heated on a metal hotplate to 35° C. (block temperature) and stirred for 16 h. A dark brown cloudy solution was obtained. LCMS analysis indicated consumption of starting material and formation of product. The mixture was partitioned between DCM (80 mL) and water (80 mL). The organic phase was separated, then concentrated in vacuo and the residue purified by column chromatography on a 40 g silicycle silica cartridge eluting with 0-10% EtOAc: DCM, to obtain the title compound (1.10 g, 58.9%) of an orange crystalline solid that darkened on standing.
$^1$H NMR (Bruker Avance III 500, 500 MHz, DMSO-$d_6$) δ ppm 2.62 (d, 3H) 4.58 (s, 2H) 4.67 (s, 1H) 6.71-6.75 (m, 1H) 6.77-6.80 (dd, 1H) 7.04-7.06 (dd, 1H), 7.61-7.62 (m, 1H). MS m/z 223 (M+H)$^+$.

Intermediate 13, Method A

2-[(3S)-7-Fluoro-3,4-dihydro-2H-1,4-benzoxazin-3-yl]-N-methyl-acetamide

Ethyl [(3S)-7-fluoro-3,4-dihydro-2H-1,4-benzoxazin-3-yl]acetate (Intermediate 10a, 50.0 g, 204.2 mmol) was dissolved in MeOH (150 mL) in a 500 mL jacketed vessel at 20° C. Methylamine (127 mL of a 33% w/w solution in EtOH, 96 g, 1.02 mol) was added in one portion and the mixture stirred at 20° C. over night. The solution was sampled and found not to have reached completion by HPLC analysis. The reaction was left stirring for a further 2 h then additional methylamine in EtOH (25.0 mL of a 33% w/w solution in EtOH; 18.9 g; 200.8 mmol) was added and the solution stirred over night at 20° C. The solution was evaporated in vacuo to an orange oil, then MeOH (300 mL) added and the mixture re-evaporated giving a beige solid, that was ground up using a mortar and pestle, then dried in a vacuum oven at 40° C. for 3 h to yield the title compound (46.3 g, 99.2% yield NMR assay 98.1% w/w, 99.7% e.p. by chiral HPLC %).
$^1$H NMR (Bruker Avance III 400, 400 MHz, DMSO-$d_6$) δ ppm 2.26 (d, 2H) 2.59 (d, 3H) 3.55-3.71 (m, 1H) 3.81 (dd, 1H) 4.12 (dq, 1H) 5.59 (s, 1H), 6.41-6.57 (m, 2H), 6.57-6.68 (m, 1H), 7.87 (d, 1H).
HRMS (Bruker micrOTOF-Q) calculated for [$C_{11}H_{13}FN_2O_2$+Na]$^+$: 247.085875. found: 247.084779.

Intermediate 13, Method B

2-[(3S)-7-Fluoro-3,4-dihydro-2H-1,4-benzoxazin-3-yl]-N-methyl-acetamide

To a 2 mL reaction vial was added 100 μL of a solution of 1,2-bis[(2S,5S)-2,5-diphenylphospholano]ethane(1,5-cyclooctadiene)rhodium(I) tetrafluoroborate (0.004 M in DCM, 0.0004 mmol) and the solvent was removed by applying vacuum. To this was added 670 μL of a stock solution of (2Z or 2E)-2-(7-fluoro-2H-1,4-benzoxazin-3(4H)-ylidene)-N-methylacetamide (Intermediate 12), 0.03 M, 0.02 mmol) containing 4 mol % Zn(OTf)$_2$ in MeOH. The vessel was pressurised with hydrogen, and the reaction was run at 331 psi hydrogen at 50° C. for 16 h to give complete conversion to the desired (S)-enantiomer in >99% ee.
HRMS m/z calculated for [$C_{11}H_{13}FN_2O_2$+H]$^+$: 225.1034. found: 225.1045.

Intermediate 14

Ethyl {7-fluoro-4-[3-oxo-3,4-dihydro-2H-1,4-benzoxazin-6-yl)carbonyl]-3,4-dihydro-2H-1,4-benzoxazin-3-yl}acetate Ethyl (7-fluoro-3,4-dihydro-2H-1,4-benzoxazin-3-yl)acetate (Intermediate 10, 1.91 g, 8.0 mmol), 3-oxo-3,4-dihydro-2H-1,4-benzoxazine-6-carboxylic acid (1.70 g, 8.80 mmol) and TEA (3.33 mL, 24.0 mmol) were dissolved in EtOAc (10 mL). T3P (50 wt. % in EtOAc, 9.52 mL, 16.0 mmol) was added and the mixture was heated at reflux over night. The reaction mixture was diluted with EtOAc (150 mL) and washed with sat. aq. NaHCO$_3$ (2×100 mL), 0.5 M HCl (100 mL) and brine (100 mL). The organic layer was dried by passage through a phase separator and concentrated giving the title compound (2.68 g, yield 81%) as an off-white solid that was used without further purification.
$^1$H NMR (500 MHz, CDCl$_3$) δ 1.26 (t, 3H), 2.61 (qd, 2H), 4.15-4.22 (m, 2H), 4.30 (dd, 1H), 4.51 (d, 1H), 4.66 (s, 2H), 5.02-5.25 (m, 1H), 6.38-6.48 (m, 1H), 6.65 (dd, 1H), 6.73 (br s, 1H), 6.90 (d, 1H), 7-7.06 (m, 1H), 7.06-7.11 (m, 1H), 8.30 (s, 1H).
MS m/z 415.2 (M+H)$^+$.

Intermediate 14a

Ethyl {(3S)-7-fluoro-4-[3-oxo-3,4-dihydro-2H-1,4-benzoxazin-6-yl)carbonyl]-3,4-dihydro-2H-1,4-benzoxazin-3-yl}acetate A mixture of 3-oxo-3,4-dihydro-2H-1,4-benzoxazine-6-carboxylic acid (151 g, 0.779 mol), N-ethyl-N-isopropylpropan-2-amine (370 mL, 2.12 mol) and ethyl [(3S)-7-fluoro-3, 4-dihydro-2H-1,4-benzoxazin-3-yl]acetate (Intermediate 10a, 169 g, 0.708 mol) in butyl acetate (800 mL) was stirred at ambient for 10 min. T3P (50 wt. % in EtOAc, 844 mL, 1.42 mol) was added during 10 min. Upon complete addition the resulting mixture was stirred for 15 min at ambient temperature before the temperature was increased to 105° C. during 85 min (1° C./min). After stirring at 105° C. for 40 h the reaction mixture was cooled to 5° C. and water (800 mL) was carefully added. After stirring for 1 h at ambient temperature the pH was adjusted to approx. 10 with NaOH (aq., 2.5 M, approx. 1.5 L). When the pH no longer changed the phases were separated. Water (1.2 L) was added to the organic phase and HCl (aq., 2 M, approx. 0.6 L) was added under stirring until the pH of the aq. phase was approx. 4. The aq. phase was discarded while the organic phase was washed with water (2×2 L), filtered through Celite (Seitz filter, K200) and concentrated to dryness. The obtained residue was dissolved in EtOAc (400 mL) and the solution was concentrated to dryness to yield crude title compound (278 g, 0.671 mol, 88% w/w, 83% yield) as a brownish foam.

¹H NMR (500 MHz, DMSO-d₆) δ 1.17 (t, 3H), 2.53 (dd, 2H), 4.06 (qdd, 2H), 4.36 (d, 2H), 4.65 (s, 2H), 4.86 (t, 1H), 6.62 (td, 1H), 6.84 (dd, 1H), 6.94 (d, 2H), 7.03 (dd, 1H), 7.07 (d, 1H), 10.82 (s, 1H).

MS m/z 415.5 (M+H)⁺.

Intermediate 15

{7-Fluoro-4-[3-oxo-3,4-dihydro-2H-1,4-benzoxazin-6-yl)carbonyl]-3,4-dihydro-2H-1,4-benzoxazin-3-yl}acetic acid LiOH (0.208 g, 8.69 mmol) dissolved in water (7.50 mL) was added to a solution of ethyl {7-fluoro-4-[(3-oxo-3,4-dihydro-2H-1,4-benzoxazin-6-yl)carbonyl]-3,4-dihydro-2H-1,4-benzoxazin-3-yl}acetate (Intermediate 14, 1.2 g, 2.90 mmol) in THF (15 mL). The mixture was stirred at rt for 1.5 h. EtOAc (40 mL) was added followed by hydrogen chloride (1 M, 11.6 mL, 11.6 mmol) and water (20 mL). The phases were separated and the organic layer was washed with brine (30 mL). The organic layer was dried over Na₂SO₄, filtered and evaporated under reduced pressure. The title compound (1.19 g, 106%) was obtained as a solid and was used without further purification.

¹H NMR (600 MHz, DMSO-d₆) δ 2.44 (dd, 1H), 2.51-2.53 (m, 1H), 4.26-4.4 (m, 2H), 4.64 (s, 2H), 4.76 (s, 1H), 6.64 (td, 1H), 6.83 (dd, 1H), 6.95 (d, 1H), 6.98-7.16 (m, 3H), 10.84 (s, 1H). The acid CO₂H proton was not detected.

HRMS (ESI+) m/z calculated for [C₁₉H₁₅FN₂O₆+H⁺]: 387.0992. found 387.0995.

Intermediate 16 tert-Butyl 7-chloro-3-oxo-2,3-dihydro-4H-1,4-benzoxazine-4-carboxylate

DMAP (0.158 g, 1.30 mmol) was added to a mixture of 7-chloro-2H-1,4-benzoxazin-3(4H)-one (2.38 g, 13.0 mmol) and di-tert-butyl dicarbonate (3.58 mL, 15.6 mmol) in THF (70 mL). The mixture was stirred at rt for 2.5 h. EtOAc (100 mL) was added. The mixture was washed with HCl (0.25 M, 50 mL), sat. aq. NaHCO₃ (50 mL) and brine, dried through a phase separator and evaporated. The title compound (3.89 g, 106%) was obtained as a crude oil and used without further purification.

¹H NMR (500 MHz, CDCl₃) δ 1.83 (s, 9H), 4.78 (s, 2H), 7.24 (dd, 1H), 7.27 (d, 1H), 7.39 (d, 1H).

Intermediate 17 tert-Butyl 7-chloro-3-hydroxy-2,3-dihydro-4H-1,4-benzoxazine-4-carboxylate

A 1 M solution of lithium triethylhydroborate (13.75 mL, 13.75 mmol) in THF was added dropwise to a solution of tert-butyl 7-chloro-3-oxo-2,3-dihydro-4H-1,4-benzoxazine-4-carboxylate (Intermediate 16, 3.25 g, 11.5 mmol) in anhydrous THF (60 mL) at −78° C. under N₂ (g). After stirring at −78° C. for 45 min, the mixture was treated with Na₂CO₃ (sat. aq., 25 mL); then H₂O₂ (35% in aq, 25 mL) was slowly added at −15° C. The mixture was stirred at rt over night, then filtered. The filtrate was concentrated in vacuo and the residue was extracted with EtOAc (2×100 mL). The organic phase was washed with brine (100 mL), dried by passage through a phase separator, and concentrated under reduced pressure giving the title compound (3.29 g, 101%) as an off-white solid that was used without further purification.

¹H NMR (500 MHz, CDCl₃) δ 1.57 (s, 9H), 3.31 (br s, 1H), 4.06 (dd, 1H), 4.27 (dd, 1H), 5.91 (t, 1H), 6.91 (dd, 1H), 6.95 (d, 1H), 7.88 (d, 1H).

Intermediate 18 tert-Butyl 7-chloro-3-(2-ethoxy-2-oxoethyl)-2,3-dihydro-4H-1,4-benzoxazine-4-carboxylate A 1 M solution of LiHMDS (23.0 mL, 23.0 mmol) in THF was a added dropwise to a solution of ethyl 2-(diethoxyphosphoryl)acetate (4.57 mL, 23.0 mmol) in THF (30 mL) at 0° C. under nitrogen and the resulting mixture was stirred for 10 min where after tert-butyl 7-chloro-3-hydroxy-2,3-dihydro-4H-1,4-benzoxazine-4-carboxylate (Intermediate 17, 3.29 g, 11.5 mmol) dissolved in THF (30 mL) was added dropwise at 0° C. The reaction mixture was stirred under nitrogen at rt for 1 h where after water (100 mL) was added and the mixture was extracted with EtOAc (3×75 mL). The combined organic layers were washed with brine (100 mL), dried by passage through a phase separator and concentrated giving crude the title compound (4.36 g, 106%) as a brown oil.

¹H NMR (500 MHz, CDCl₃) δ 1.24 (t, 3H), 1.52 (s, 9H), 2.46 (dd, 1H), 2.57 (dd, 1H), 4.03-4.2 (m, 3H), 4.34 (dd, 1H), 4.98 (t, 1H), 6.78-6.93 (m, 2H), 7.80 (br s, 1H).

MS m/z 356 (M+H)⁺.

Intermediate 19

Ethyl (2E or 2Z)-(7-chloro-2H-1,4-benzoxazin-3 (4H)-ylidene)acetate

Ethyl 4-chloro-3-oxobutanoate (60.1 g, 0.36 mol) was added to a well-stirred solution of 5-chloro-2-aminophenol (43.4 g, 0.30 mol) in THF (434 mL) at 20° C. The resulting mixture was stirred for 30 min, then TEA (36.8 g, 0.36 mol) was added into dropwise at 50° C. The resulting solution was stirred at this temperature for 16 h. The organic solvent was removed in vacuo. The crude product was purified by silica gel column chromatography with EtOAc in PE from 0% to 1.6%. The product was further purified by re-crystallization in cyclohexane. This resulted in the title compound (53.8 g, 70%) as a light yellow solid.

¹H NMR (400 MHz, DMSO-d₆) δ 1.20 (3H, t), 4.11 (2H, q), 4.68 (2H, s), 4.78 (1H, s), 6.97 (1H, dd), 7.00 (1H, d), 7.31 (1H, d), 10.18 (1H, s).

MS m/z 254 (M+H)⁺.

Intermediate 20

Ethyl (7-chloro-3,4-dihydro-2H-1,4-benzoxazin-3-yl)acetate

A solution of tert-butyl 7-chloro-3-(2-ethoxy-2-oxoethyl)-2,3-dihydro-4H-1,4-benzoxazine-4-carboxylate (Intermediate 18, 1.98 g, 5.56 mmol) in DCM (10 mL)/TFA (5 mL, 67.3 mmol) was stirred at rt for 2.5 h. The mixture was concentrated, dissolved in DCM (50 mL), and washed with sat. aq. NaHCO₃ (2×50 mL), then dried by passage through a phase separator and concentrated giving 1.52 g of an oil. The compound was purified by preparative HPLC (XBridge C18 column (10 μm 250×50 ID mm), using a gradient of 15-55% ACN in H₂O/ACN/NH₃ 95/5/0.2 buffer over 20 min with a flow of 100 mL/min, UV detection at 240 nm). Removal of the solvents gave the title compound (0.67 g, 47%) as an oil.

¹H NMR (500 MHz, CDCl₃) δ 1.29 (t, 3H), 2.53 (d, 2H), 3.83 (qd, 1H), 3.94 (dd, 1H), 4.15-4.23 (m, 3H), 6.52 (d, 1H), 6.74 (dd, 1H), 6.79 (d, 1H). The spectra also shows two broad singlets at δ 1.61 and 4.40 assigned as H$_2$O and NH respectively.

MS m/z 256 (M+H)$^+$.

Intermediate 20a and 20b, Method A

Ethyl [(3R and 3S)-7-chloro-3,4-dihydro-2H-1,4-benzoxazin-3-yl]acetate

The enantiomers of ethyl (7-chloro-3,4-dihydro-2H-1,4-benzoxazin-3-yl)acetate (Intermediate 20, 13.7 g, 53.7 mmol) were separated by chiral separation, using a ChiralPak AD column (20 μm, 250×50 mm) with a mobile phase of EtOH/TEA 100/0.1 at 20° C., with a flow of 120 mL/min and detection at 270 nm.

Intermediate 20a, Method A

Ethyl [(3S)-7-chloro-3,4-dihydro-2H-1,4-benzoxazin-3-yl]acetate

The first eluted compound was collected and evaporated to yield the title compound (6.64 g, 48.4%, 99.2% ee).

$^1$H NMR (500 MHz, CDCl$_3$) δ 1.29 (t, 3H), 2.53 (d, 2H), 3.78-3.87 (m, 1H), 3.94 (dd, 1H), 4.16-4.24 (m, 3H), 4.46 (s, 1H), 6.52 (d, 1H), 6.74 (dd, 1H), 6.79 (d, 1H).

Optical rotation [α]$_D^{20}$=−53.5° (ACN, c=1).

Intermediate 20b, Method A

Ethyl [(3R)-7-chloro-3,4-dihydro-2H-1,4-benzoxazin-3-yl]acetate

The second eluted compound was collected and evaporated to yield the title compound (6.47 g, 47.1%, 98.9% ee).

$^1$H NMR (500 MHz, CDCl$_3$) δ 1.29 (t, 3H), 2.53 (d, 2H), 3.78-3.88 (m, 1H), 3.94 (dd, 1H), 4.15-4.25 (m, 3H), 4.46 (s, 1H), 6.52 (d, 1H), 6.74 (dd, 1H), 6.79 (d, 1H). Optical rotation [α]$_D^{20}$=+55.5° (ACN, c=1).

The absolute configuration was determined using VCD by first dissolving 15 mg of the solid material in 140-150 μl CDCl$_3$ for each sample. The solutions were then transferred to 0.100 mm BaF2 cells and the VCD spectra were acquired for six h each in a BioTools ChiraliR instrument equipped with dual source and dual photoelastic modulator. The resolution was 4 cm$^{-1}$. A Monte Carlo molecular mechanics search for low energy geometries was conducted for slightly truncated structures (methyl ester was used instead of ethyl ester) of the two enantiomers, R and S. MacroModel within the Maestro graphical interface (Schrödinger Inc.) was used to generate starting coordinates for conformers. All conformers within 5 kcal/mole of the lowest energy conformer were used as starting points for density functional theory (DFT) minimizations within Gaussian09. Optimized structures, harmonic vibrational frequencies/intensities, VCD rotational strengths, and free energies at STP (including zero-point energies) were determined for each conformer. In these calculations, the functional B3LYP and the basis set 6-31G* were used. Simulations of infrared and VCD spectra for each conformation were generated using an in-house built program to fit Lorentzian line shapes (12 cm$^{-1}$ line width) to the computed spectra thereby allowing direct comparisons between simulated and experimental spectra.

The experimental VCD spectra of Intermediate 20a and Intermediate 20b obtained in CDCl$_3$ were compared with the simulated spectra of the two enantiomers. The comparison demonstrates that Intermediate 20a is the S enantiomer and Intermediate 20b has R configuration. Most major bands confirm this interpretation.

Intermediate 20a, Method B

Ethyl [(3S)-7-chloro-3,4-dihydro-2H-1,4-benzoxazin-3-yl]acetate

Zinc trifluoromethanesulfonate (2.87 g, 7.91 mmol) was added to a well-stirred solution of (2E or Z)-(7-chloro-2H-1,4-benzoxazin-3(4H)-ylidene)acetate (Intermediate 19, 20 g, 79.1 mmol) in EtOH (150 mL, HPLC grade) at 20° C. The resulting mixture was evacuated and purged with N$_2$ for several times, then (+)-1,2-bis(2s, 5s)-2,5-diphenylphospholanol ethane(1,5-cyclooctadiene) rhodium(I)tetrafluoroborate (0.51 g, 0.63 mmol) was added at 20° C. The resulting solution was evacuated and purged with N$_2$ for several times again. Then the reaction was stirred at 60° C. for 16 h under H$_2$ (15 bar pressure). The mixture was concentrated. The crude product was purified by silica gel column chromatography with EtOAc in PE from 0 to 20%. The pure product fraction was concentrated. This resulted in the title compound (18.9 g, 93.6%) as an orange oil.

$^1$H NMR (300 MHz, CDCl$_3$) δ 1.28 (3H, t), 2.52 (2H, d), 3.78-3.85 (1H, m), 3.93 (1H, dd), 4.15-4.22 (3H, m), 4.44 (1H, brs), 6.50 (1H, d), 6.73 (1H, dd), 6.78 (1H, d).

MS m/z 256 (M+H)$^+$.

[α]$_D^{20}$=−56.45° (c=0.1 g/100 mL, CH$_3$CN, T=17° C.).

Intermediate 21

Ethyl {7-chloro-4-[(3-oxo-3,4-dihydro-2H-1,4-benzoxazin-6-yl)carbonyl]-3,4-dihydro-2H-1,4-benzoxazin-3-yl}acetate Ethyl (7-chloro-3,4-dihydro-2H-1,4-benzoxazin-3-yl)acetate (Intermediate 20, 0.67 g, 2.62 mmol), 3-oxo-3,4-dihydro-2H-1,4-benzoxazine-6-carboxylic acid (0.607 g, 3.14 mmol), and TEA (1.090 mL, 7.86 mmol) were dissolved in EtOAc (15 mL). Then T3P (50 wt. % in EtOAc, 3.12 mL, 5.24 mmol) was added and the mixture was heated in a microwave reactor for 2 h at 160° C. EtOAc (100 mL) was added and the mixture was washed with sat. aq. NaHCO$_3$ (100 mL), 1 M HCl (100 mL) and brine (100 mL). The mixture was dried by passage through a phase separator. Concentration under reduced pressure gave 1.14 g of an oil that was purified by flash chromatography on silica gel using a gradient from 12% to 100% of EtOAc in heptane as eluent. Concentration to dryness gave the title compound (0.530 g, 46.9%).

$^1$H NMR (500 MHz, CDCl$_3$) δ 1.26 (t, 3H), 2.61 (qd, 2H), 4.13-4.2 (m, 2H), 4.30 (dd, 1H), 4.48-4.55 (m, 1H), 4.66 (s, 2H), 4.95-5.24 (m, 1H), 6.62-6.71 (m, 2H), 6.89 (d, 1H), 6.92-6.95 (m, 1H), 7.03 (dd, 1H), 7.11 (d, 1H), 8.58 (s, 1H).

MS m/z 431 (M+H)$^+$.

Intermediate 21a

Ethyl {(3S)-7-chloro-4-[3-oxo-3,4-dihydro-2H-1,4-benzoxazin-6-yl)carbonyl]-3,4-dihydro-2H-1,4-benzoxazin-3-yl}acetate DIPEA (12.38 mL, 71.08 mmol) and T3P (50% in butyl acetate, 30.2 g, 47.4 mmol) was added to a suspension of ethyl [(3S)-7-chloro-3,4-dihydro-2H-1,4-benzoxazin-3-yl]acetate (Intermediate 20a, 6.06 g, 23.7 mmol) and 3-oxo-3,4-dihydro-2H-1,4-benzoxazine-6-carboxylic acid (5.418 g, 28.05 mmol) in butyl acetate (60 mL). The reaction mixture was heated in a alumina block at 117° C. for 16 h. The reaction mixture was allowed to cool to rt The mixture was diluted with EtOAc (150 mL) and washed with sat. aq. $Na_2CO_3$ (100+30 mL), citric acid (1 M, 50 mL), HCl (1 M, 50 mL) and brine (100 mL). The organic phase was dried over anhydrous $Na_2SO_4$, filtered and concentrated to afford crude product as a red, foamy oil. The residue was purified by automated flash chromatography on a Biotage® KP-SIL 340 g column. A gradient from 30% to 75% of EtOAc in heptane over 7 CV was used as mobile phase. The product was collected using detection at wavelength 254/280 nm. The title compound (7.62 g, 74.6%) was obtained as a foamy solid.

$^1$H NMR (500 MHz, DMSO-$d_6$) δ 1.15-1.18 (m, 3H), 2.51-2.55 (m, 2H), 4.03-4.1 (m, 2H), 4.34-4.41 (m, 2H), 4.65 (s, 2H), 4.86 (t, 1H), 6.80 (dd, 1H), 6.87 (d, 1H), 6.94 (d, 1H), 7.01-7.07 (m, 2H), 7.08 (d, 1H), 10.82 (s, 1H).

MS m/z 431.1 (M+H)$^+$.

Intermediate 21a, Method B

Ethyl {(3S)-7-chloro-4-[(3-oxo-3,4-dihydro-2H-1,4-benzoxazin-6-yl)carbonyl]-3,4-dihydro-2H-1,4-benzoxazin-3-yl}acetate T3P (50% solution in EtOAc, 146 g, 230 mmol) was added into a solution of ethyl [(3S)-7-chloro-3,4-dihydro-2H-1,4-benzoxazin-3-yl]acetate (Intermediate 20a, 29.4 g, 115 mmol) in n-BuOAc (100 mL), 3-oxo-3,4-dihydro-2H-1,4-benzoxazine-6-carboxylic acid (22.7 g, 118 mmol) and DIPEA (44.5 g, 345 mmol) at 20° C. The resulting mixture was stirred at 140° C. for 24 h. The reaction mixture was cooled and diluted with of EtOAc (500 mL). The resulting mixture was washed with 200 mL of saturated sodium bicarbonate, 200 mL of 1 M citric acid and 200 mL of 1 M HCl. The organic phase was dried over anhydrous $Na_2SO_4$, filtered and evaporated to dryness. The residue was applied onto a silica gel column and eluted with EtOAc/PE (1/10 to 1/1). The pure fraction was concentrated in vacuo to afford the title compound (41 g, 83%) as a yellow solid.

$^1$H NMR (300 MHz, DMSO-$d_6$) δ 1.17 (3H, t), 2.50-2.58 (2H, m), 3.99-4.12 (2H, m), 4.38 (2H, s), 4.65 (2H, s), 4.87 (1H, t), 6.78-6.99 (3H, m), 7.00-7.09 (3H, m), 10.81 (1H, s).

MS m/z 431 (M+H)$^+$.

Intermediate 21b

Ethyl {(3R)-7-chloro-4-[(3-oxo-3,4-dihydro-2H-1,4-benzoxazin-6-carbonyl]-3,4-dihydro-2H-1,4-benzoxazin-3-yl}acetate A mixture of 3-oxo-3,4-dihydro-2H-benzo[b][1,4]oxazine-6-carboxylic acid (1.68 g, 8.6 mmol), DIPEA (4.1 mL, 23.5 mmol) and ethyl [(3R)-7-chloro-3,4-dihydro-2H-1,4-benzoxazin-3-yl]acetate (Intermediate 20b, 2.0 g, 7.8 mmol) in butyl acetate (9 mL) was stirred at ambient for 15 min. T3P (50% w/w in BuOAc, 9.3 mL, 15.6 mmol) was added during 2 min. Upon complete addition the resulting mixture was stirred for 10 min at ambient temperature before the temperature was increased to 120° C. during 50 min (2° C./min). After stirring at 120° C. for 40 h the reaction mixture was cooled to 20° C. and water (20 mL) was carefully added followed by the addition of EtOAc (20 mL). After stirring for 30 min at ambient temperature the pH was adjusted to ca 10 with 6% $Na_2CO_3$ (aq., approx. 20 mL). When the pH no longer changed the phases were separated. The organic phase was washed with citric acid (10% aq., 2×20 mL), NaHCO$_3$ (8% aq., 20 mL), and brine (20 mL). The organic phase was dried over MgSO$_4$, filtered through a plug of silica and the solution was concentrated to dryness to yield crude title compound (3.25 g, 0.622 mmol, 95% w/w, 80% yield) as a brownish foam.

$^1$H NMR (400 MHz, CDCl$_3$) δ 1.27 (t, 3H), 2.54-2.71 (m, 2H), 4.17 (qd, 2H), 4.31 (dd, 1H), 4.53 (dd, 1H), 4.66 (s, 2H), 5.12 (t, 1H), 6.66 (dd, 2H), 6.90 (d, 1H), 6.95 (d, 1H), 7.04 (dd, 1H), 7.12 (d, 1H), 8.59 (s, 1H).

MS m/z 431.3 (M+H)$^+$.

Intermediate 22

{7-Chloro-4-[3-oxo-3,4-dihydro-2H-1,4-benzoxazin-6-carbonyl]-3,4-dihydro-2H-1,4-benzoxazin-3-yl}acetic acid A mixture of ethyl {7-chloro-4-[(3-oxo-3,4-dihydro-2H-1,4-benzoxazin-6-yl)carbonyl]-3,4-dihydro-2H-1,4-benzoxazin-3-yl}acetate (Intermediate 21, 42 mg, 0.10 mmol) and LiOH (1 M, 0.146 mL, 0.15 mmol) in THF (2 mL) was stirred at rt for 2 h. Additional LiOH (1 M, 0.070 mL, 0.07 mmol) was added and the mixture was stirred for 2 h. HCl (1 M, 5 mL) was added and the aq. phase was extracted with DCM (3×5 mL). The combined organic layers were dried by passage through a phase separator and concentrated in vacuo providing the title compound (38.0 mg, 97%) as a white solid.

MS m/z 403.1 (M+H)$^+$.

Intermediate 22a

{(3S)-7-Chloro-4-[(3-oxo-3,4-dihydro-2H-1,4-benzoxazin-6-yl)carbonyl]-3,4-dihydro-2H-1,4-benzoxazin-3-yl}acetic acid LiOH (1.40 g, 58.3 mmol) was dissolved in water (50 mL) and added to (S)-ethyl {7-chloro-4-[(3-oxo-3,4-dihydro-2H-1,4-benzoxazin-6-yl)carbonyl]-3,4-dihydro-2H-1,4-benzoxazin-3-yl}acetate (Intermediate 21a, 5.71 g, 11.7 mmol) in THF (50 mL). The reaction mixture was stirred at rt for 75 min EtOAc (150 mL) was added. Washed with HCl (1 M, 100+50 mL) and brine (50 mL). The organic phase was dried over $Na_2SO_4$ and after filtration the solvents were evaporated in vacuo to yield the crude the title compound (82 mg, 107%) which was used further in the synthesis of Example 5a.

$^1$H NMR was obtained on pure material recovered from the synthesis of Example 5a: $^1$H NMR (500 MHz, DMSO-$d_6$) δ 2.4-2.48 (m, 1H), 2.51-2.56 (m, 1H), 4.29-4.4 (m, 2H), 4.65 (s, 2H), 4.71-4.87 (m, 1H), 6.81 (dd, 1H), 6.93-7.03 (m, 2H), 7.03-7.1 (m, 3H), 10.84 (s, 1H), 12.53 (s, 1H).

MS m/z 403.1 (M+H)$^+$.

Intermediate 23 tert-Butyl 7-bromo-3-oxo-2,3-dihydro-4H-1,4-benzoxazine-4-carboxylate

Di-tert-butyl dicarbonate (919 mg, 4.21 mmol) and DMAP (42.9 mg, 0.35 mmol) were added to a solution of 7-bromo-2H-1,4-benzoxazin-3(4H)-one (800 mg, 3.51 mmol) in THF (20 mL). Stirred at rt for 2.5 h. EtOAc (100 mL) was added and the mixture washed with HCl (30 mL, 0.25 M), sat. aq. $Na_2CO_3$ (30 mL) and brine (30 mL), dried through a phase separator and solvents were evaporated to give crude title compound which was used directly in the synthesis of Intermediate 24 (1.16 g, 100%).

Intermediate 24 tert-Butyl 7-bromo-3-(2-ethoxy-2-oxoethyl)-2,3-dihydro-4H-1,4-benzoxazine-4-carboxylate Step 1. Lithium triethylhydroborate (1M in THF, 4.23 mL, 4.23 mmol) was added dropwise to a solution of tert-butyl 7-bromo-3-oxo-2,3-dihydro-4H-1,4-benzoxazine-4-carboxylate (Intermediate 23, 1.16 g, 3.52 mmol) in THF (20 mL) at −78° C. The mixture was stirred at −78° C. for 1 h whereupon $Na_2CO_3$ (sat. aq. 4 mL) was added and the mixture was warmed to about −20° C. $H_2O_2$ (30%, 4 mL) was added dropwise while maintaining low temp. The mixture was stirred at about −10° C. for 20 min. The mixture was filtered through celite and the plug was washed with THF. EtOAc (50 mL) was added and the mixture was washed with brine (20 mL), dried through a phase separator and evaporated under reduced pressure. The crude hemiaminal was obtained as a yellow oil and used without purification.

Step 2. In another flask LiHMDS (7.75 mL, 7.75 mmol) was slowly added to a solution of ethyl 2-(diethoxyphosphoryl)acetate (1.55 mL, 7.75 mmol) in THF (8 mL) keeping the temperature less than 5° C. The mixture was stirred at rt for 30 min and then cooled to 0° C. The crude hemiaminal from Step 1 above was dissolved in THF (10 mL) and added dropwise at 0° C. The ice bath was removed and the reaction was stirred at rt for 2 h. EtOAc (70 mL) was added and the mixture was washed with sat. aq. $Na_2CO_3$ (2×30 mL), HCl (0.25 M, 20 mL) and brine, dried through a phase separator and evaporated under reduced pressure. The residue was purified by automated flash chromatography on a Biotage® KP-SIL 50 g column. A gradient from 5% to 25% of EtOAc in heptane over 6CV was used as mobile phase. The product was collected using detection at the wavelength 250/285 nm. The title compound (0.556 g, 39.4%) was obtained as a oil after removal of solvents.

$^1$H NMR (500 MHz, $CDCl_3$) δ 1.26 (t, 3H), 1.54 (s, 9H), 2.48 (dd, 1H), 2.58 (dd, 1H), 4.08-4.20 (m, 3H), 4.35 (dd, 1H), 4.99 (s, 1H), 7.02 (dd, 1H), 7.05 (d, 1H), 7.75 (s, 1H).

Intermediate 25

Ethyl (2E or 2Z)-(7-bromo-2H-1,4-benzoxazin-3(4H)-ylidene)acetate

Ethyl 4-chloro-3-oxobutanoate (45 mL, 333 mmol) was added to a solution of 2-amino-5-bromophenol (55.7 g, 296 mmol) in THF (400 mL) at rt. The mixture was heated to 50° C., and TEA (57 mL, 326 mmol) was added into slowly over 30 min. The resulting mixture was stirred at this temperature for 16 h. The mixture was diluted with water (500 mL) and extracted with EtOAc (500 mL×3). The combined organic phase was washed with brine (500 mL×2), dried over anhydrous $Na_2SO_4$, filtered and concentrated by evaporation. The residue was purified by a silica chromatography using a solvent gradient from 1.25% to 2% of EtOAc in PE. The pure fraction was evaporated to dryness to afford the title compound (47 g, 56%) as a light yellow solid.

$^1$H NMR (300 MHz, $CDCl_3$) δ 1.29 (3H, t), 4.18 (2H, q), 4.56 (2H, s), 4.70 (1H, s), 6.70 (1H, d), 7.02-7.06 (2H, m), 10.14 (1H, brs).

MS m/z 298 (M+H)$^+$.

Intermediate 26

Ethyl (2E)-4-(5-bromo-2-nitrophenoxy)but-2-enoate

5-Bromo-2-nitrophenol (10 g, 45.9 mmol) and $K_2CO_3$ (8.24 g, 59.6 mmol) were suspended in NMP (81 mL) (a bright red suspension) and ethyl 4-bromocrotonate (10.26 mL, 59.63 mmol) was added dropwise at room temperature. The reaction was stirred at room temperature over night (20 h). The mixture was poured into ice/water (500 mL) and stirred for 30 min. The precipitate was collected by filtration and washed with water (2×200 mL), air dried for 10 min and then washed with heptane (200 mL). Heptane (200 mL) was added to the solid and stirred for 1 h. The solid was filtered off, washed with heptane (2×50 mL) and dried in vacuo to afford a beige solid. The title compound (15.0 g, 99%) was obtained and was used without further purification.

$^1$H NMR (500 MHz, $CDCl_3$) δ 1.32 (t, 3H), 4.24 (q, 2H), 4.84 (dd, 2H), 6.31 (dt, 1H), 7.04 (dt, 1H), 7.18-7.26 (m, 2H), 7.80 (d, 1H).

MS m/z 298 (M−H)$^-$.

Intermediate 27, Method A

Ethyl (7-bromo-3,4-dihydro-2H-1,4-benzoxazin-3-yl)acetate tert-Butyl 7-bromo-3-(2-ethoxy-2-oxoethyl)-2,3-dihydro-4H-1,4-benzoxazine-4-carboxylate (Intermediate 24, 556 mg, 1.39 mmol) was dissolved in hydrogen chloride in dioxane (5.0 mL, 162.8 mmol) and the mixture stirred for 2 h at rt. The solvent was evaporated and the residue dissolved in EtOAc (50 mL), washed with sat. aq. $Na_2CO_3$ (30 mL) and brine (20 mL), dried over $Na_2SO_4$ and evaporated after filtration to give the title compound (399 mg, 96%) as an oil.

MS m/z 300 (M+H)$^+$.

Intermediate 27, Method B

Ethyl (7-bromo-3,4-dihydro-2H-1,4-benzoxazin-3-yl)acetate

A solution of ethyl (2E)-4-(5-fluoro-2-nitrophenoxy)but-2-enoate (Intermediate 26, 15.0 g, 45.4 mmol) in acetic acid (125 mL) was added dropwise to a slurry of iron dust (10.13 g, 181.5 mmol) and acetic acid (50 mL, 873.6 mmol) at 60° C. (internal temp, 70° C. dry bath) under nitrogen atmosphere and the internal temperature kept below 70° C. during addition. The residual reactant was washed down with acetic acid (25 mL). The reaction mixture was heated at 60° C. for 1.5 h. The temperature was increased to 70° C. (internal, 80° C. dry bath) and stirred for an additional 1.5 h. The reaction mixture was allowed to cool to rt over night. The mixture was diluted with EtOAc (150 mL), filtered through celite, washed with EtOAc (2×100 mL) and concentrated in vacuo. The crude was dissolved in EtOAc (200 mL) and washed with a 1 M aq. citric acid solution (2×100 mL). The organic layer was washed with sat. aq. $Na_2CO_3$ (2×50 mL). The organic layer was further washed with aq. citric acid (50 mL, 0.5M), sat. aq. $Na_2CO_3$ (50 mL) and brine (50 mL). The organic layer was filtered through a phase separator and treated with silica (10 g) for 10 min. The mixture was filtered and the silica was washed with EtOAc (2×50 mL). The organic layer was evaporated to give a dark brown oil. (11 g). The residue was purified by automated flash chromatography on a Biotage® KP-SIL 340 g column. A gradient from 5% to 40% of EtOAc in heptane over 5 CV was used as mobile phase. The product was collected using the wavelength 254/280 nm. The title compound (10.4 g, 76%) was obtained as a light yellow oil.

$^1$H NMR (500 MHz, $CDCl_3$) δ 1.29 (t, 3H), 2.53 (d, 2H), 3.78-3.87 (m, 1H), 3.94 (dd, 1H), 4.16-4.23 (m, 3H), 4.47 (s, 1H), 6.47 (d, 1H), 6.88 (dd, 1H), 6.93 (d, 1H).

MS m/z 300 (M+H)$^+$.

Intermediate 27a and 27b

Ethyl [(3R and 3S)-7-bromo-3,4-dihydro-2H-1,4-benzoxazin-3-yl]acetate

The enantiomers of ethyl 2-(7-bromo-3,4-dihydro-2H-benzo[b][1,4]oxazin-3-yl)acetate (Intermediate 27, 13.73 g, 45.75 mmol) were separated by chiral separation, using a ChiralPak AD column (20 μm, 250×50 mm) with a mobile phase of EtOH/TEA 100/0.1 at 20° C., with a flow of 120 mL/min and detection at 280 nm.

Intermediate 27a, Method A

Ethyl [(3S)-7-bromo-3,4-dihydro-2H-1,4-benzoxazin-3-yl]acetate

The first eluted compound was collected and evaporated to yield the title compound (4.2 g, 30.6%, 99.9% ee).
$^1$H NMR (500 MHz, CDCl$_3$) δ 1.29 (t, 3H), 2.53 (d, 2H), 3.78-3.86 (m, 1H), 3.94 (dd, 1H), 4.14-4.24 (m, 3H), 4.47 (s, 1H), 6.47 (d, 1H), 6.87 (dd, 1H), 6.93 (d, 1H).
Optical rotation $[\alpha]_D^{20}$=−56.5° (ACN, c=1).

Intermediate 27b, Method A

Ethyl [(3R)-7-bromo-3,4-dihydro-2H-1,4-benzoxazin-3-yl]acetate

The second eluted compound was collected and evaporated to yield the title compound (6.6 g, 33.5%, 99.4% ee).
$^1$H NMR (500 MHz, CDCl$_3$) δ 1.29 (t, 3H), 2.53 (d, 2H), 3.78-3.86 (m, 1H), 3.94 (dd, 1H), 4.14-4.24 (m, 3H), 4.47 (s, 1H), 6.47 (d, 1H), 6.87 (dd, 1H), 6.93 (d, 1H).
Optical rotation $[\alpha]_D^{20}$=+56.6° (ACN, c=1).

The absolute configurations of Intermediate 27a and 27b were determined by recording and comparing VCD for the two enantiomers with those calulated for the corresponding methyl esters (to reduce the number of comptational conformations). Intermediate 27a (16.9 mg) was dissolved in 170 μL CDCl$_3$. Intermediate 27b (14.9 mg) was dissolved in 150 μL CDCl$_3$. The solutions were transferred to 0.100 mm BaF2 cells and the VCD spectra were acquired for seven hours each in a BioTools ChiralIR instrument equipped with dual source and dual photoelastic modulator. The resolution was 4 cm$^{-1}$.

A Monte Carlo molecular mechanics search for low energy geometries was conducted for slightly truncated structures (methyl ester was used instead of ethyl ester) of the two enantiomers, R and S. The structures used for the simulations are shown in FIG. 3. MacroModel within the Maestro graphical interface (Schrödinger Inc.) was used to generate starting coordinates for conformers. All conformers within 5 kcal/mole of the lowest energy conformer were used as starting points for density functional theory (DFT) minimizations within Gaussian09. Optimized structures, harmonic vibrational frequencies/intensities, VCD rotational strengths, and free energies at STP (including zero-point energies) were determined for each conformer. In these calculations, the functional B3LYP and the basis set 6-31 G* were used. Simulations of infrared and VCD spectra for each conformation were generated using an in-house built program to fit Lorentzian line shapes (12 cm-1 line width) to the computed spectra thereby allowing direct comparisons between simulated and experimental spectra. The experimental spectra of the two samples were compared with the simulated spectra of the two methyl ester enantiomers. The agreement between the experimental and simulated spectra was good and Intermediate 27a can unambiguously be assigned as the S enantiomer and Intermediate 27b as the R isomer.

Intermediate 27a, Method A

Ethyl [(3S)-7-bromo-3,4-dihydro-2H-1,4-benzoxazin-3-yl]acetate

The enantiomers of Example 27 (1.6 g, 5.3 mmol) were separated by chiral separation, using a Chiralpak AD-H (5 μm, 250×20 mm) with a mobile phase of 40% MeOH in CO$_2$, at 85 bar at 35° C., with a flow of 47 mL/min (40 g/mL) and detection at 254 nm. The second eluted compound was collected and evaporated to yield ISOMER 2 of the title compound (277 mg, 17.3%, 99.3% ee).
$^1$H NMR (300 MHz, CD$_3$OD) δ 1.27 (3H, t), 2.47-2.61 (2H, m), 3.73-3.80 (1H, m), 3.93 (1H, dd), 4.14-4.21 (3H, m), 6.53 (1H, d), 6.79-6.83 (2H, m).
MS m/z 300 (M+H)$^+$.

Intermediate 27a, Method B

Ethyl [(3S)-7-bromo-3,4-dihydro-2H-1,4-benzoxazin-3-yl]acetate

Zn(OTf)$_2$ (2.4 g, 6.63 mmol) was added to ethyl (2E or 2Z)-(7-bromo-2H-1,4-benzoxazin-3(4H)-ylidene)acetate (Intermediate 25, 47.5 g, 160 mmol) in EtOH (HPLC grade, 500 mL) at rt under N$_2$-atmosphere. The mixture was evacuated and backfilled with nitrogen for several times before (S,S)[Ph-BPE Rh COD]BF$_4$ (900 mg, 0.112 mmol) was added. The resulting mixture was evacuated and backfilled with hydrogen several times. The mixture was stirred at 60° C. for 16 h under hydrogen (15 bar). After cooling to ambient temperature the pressure was released. The organic solvent was removed by evaporation. The crude product was purified by flash chromatography (C18 material) with and eluent gradient from 10% to 60% MeCN in water (containing 0.1% NH$_4$HCO$_3$). The pure fraction were pooled and evaporated to dryness to afford the title compound (44 g, 92% yield, ee 100% (SFC analysis using Chiralpak IC-3 (0.46×10 cm, 3 μm); eluent, MeOH (0.15 DEA)/CO$_2$ 40/60)) as a solid.
$^1$H NMR (300 MHz, CD$_3$OD) δ 1.27 (3H, t), 2.47-2.61 (2H, m), 3.73-3.80 (1H, m), 3.93 (1H, dd), 4.14-4.21 (3H, m), 6.53 (1H, d), 6.79-6.83 (2H, m).
MS m/z 300 (M+H)$^+$.

Intermediate 28

Ethyl {7-bromo-4-[(3-oxo-3,4-dihydro-2H-1,4-benzoxazin-6-yl)carbonyl]-3,4-dihydro-2H-1,4-benzoxazin-3-yl}acetate TEA (0.737 mL, 5.32 mmol) and T3P (50 wt. % in EtOAc, 2.372 mL, 3.99 mmol) were added to a solution of ethyl (7-bromo-3,4-dihydro-2H-1,4-benzoxazin-3-yl)acetate (Intermediate 27, 399 mg, 1.33 mmol) and 3-oxo-3,4-dihydro-2H-1,4-benzoxazine-6-carboxylic acid (308 mg, 1.60 mmol) in EtOAc (7 mL). The reaction mixture was heated in a microwave reactor at 150° C. for 2 h. Additional T3P (50 wt. % in EtOAc, 1.2 mL, 2.02 mmol) and TEA (0.3 mL, 2.16 mmol) was added and the mixture was heated in a microwave reactor at 150° C. for another 2 h. EtOAc (50 mL) was added and the mixture washed with sat. aq. Na$_2$CO$_3$ (2×30 mL), HCl (30 mL, 0.5M) and brine, dried through a phase separator and evaporated. The compound was purified by preparative HPLC (Kromasil C8 column (10 μm 250×50 ID mm) using a gradient of 35-75% ACN in H₂O/ACN/FA 95/5/0.2 buffer over 20 min with a flow of 100 mL/min, UV detection at 254/280 nm). The title compound (366 mg, 58%) was obtained after removal of solvents in vacuo.

MS m/z 475 (M+H)⁺.

Intermediate 28a, Method A

Ethyl 2-[(3S)-7-bromo-4-(3-oxo-4H-1,4-benzoxazine-6-carbonyl)-2,3-dihydro-1,4-benzoxazin-3-yl]acetate In a 250 mL 3-necked flask, ethyl [(3S)-7-bromo-3,4-dihydro-2H-1,4-benzoxazin-3-yl]acetate (Intermediate 27a, 4.2 g, 14.0 mmol) and 3-oxo-3,4-dihydro-2H-benzo[b][1,4]oxazine-6-carboxylic acid (2.73 g, 14.1 mmol) were suspended in butyl acetate (40 mL). DIPEA (7.31 mL, 42.0 mmol) was added followed by T3P (50% in BuOAc) (17.8 g, 28.0 mmol). The reaction was heated in an alumina block for 7 h at 117° C. (internal reaction temp. the heating block was set to 135° C.). The reaction was allowed to cool to r.t over night. The crude reaction was diluted with EtOAc (150 mL) and washed with sat. aq. NaHCO₃ (100+30 mL), 1 M citric acid aq. (50 mL), 1 M HCl (50 mL) and brine (100 mL), dried over anhydrous Na₂SO₄, filtered and concentrated to afford crude product as a red and foamy oil. The residue was purified by automated flash chromatography on a Biotage® KP-SIL 340 g column. A gradient from 30% to 75% of EtOAc in heptane over 5 CV was used as mobile phase. The product was collected using the wavelengths 254/280 nm. The title compound (4.23 g, 63.6%) was obtained as a foamy solid.

¹H NMR (500 MHz, CDCl₃) δ 1.27 (t, 3H), 2.54-2.7 (m, 2H), 4.14-4.22 (m, 2H), 4.31 (dd, 1H), 4.53 (dd, 1H), 4.66 (s, 2H), 5.12 (s, 1H), 6.62 (d, 1H), 6.80 (dd, 1H), 6.90 (d, 1H), 7.04 (dd, 1H), 7.08-7.14 (m, 2H), 8.51 (s, 1H).

MS m/z 475 (M+H)⁺.

Intermediate 28a, Method B

Ethyl 2-[(3S)-7-bromo-4-(3-oxo-4H-1,4-benzoxazine-6-carbonyl)-2,3-dihydro-1,4-benzoxazin-3-yl]acetate DIPEA (46.4 g, 360 mmol) was added to ethyl [(3S)-7-bromo-3,4-dihydro-2H-1,4-benzoxazin-3-yl]acetate (Intermediate 27a, 36 g, 120 mmol), 3-oxo-3,4-dihydro-2H-benzo[b][1,4]oxazine-6-carboxylic acid (28 g, 144 mmol) and 2,4,6-tripropyl-1,3,5,2,4,6-trioxatriphosphinane 2,4,6-trioxide (50% solution in EtOAc) (152.6 g, 240 mmol) in butyl acetate (100 mL) at rt. The resulting suspension was stirred at 140° C. for 2 hours. The reaction mixture was diluted with EtOAc (700 mL) and washed with saturated NaHCO₃ (500 mL), 1 M HCl (500 mL) and brine (500 mL). The organic layer was dried over anhydrous Na₂SO₄, filtered and evaporated to afford crude product. The residue was purified by a silica chromatography, eluent gradient from 5% to 20% of EtOAc in PE. The pure fraction was evaporated to dryness to afford title compound (33 g, 58%) as an off-white solid.

¹H NMR (300 MHz, CDCl₃) δ 1.26 (3H, t), 2.56-2.64 (2H, m), 4.16 (2H, q), 4.30 (1H, dd), 4.52 (1H, d), 4.66 (2H, s), 5.11 (1H, t), 6.61 (1H, d), 6.79 (1H, dd), 6.89 (1H, d), 7.03 (1H, dd), 7.11 (2H, dd), 8.90 (1H, brs).

MS m/z 475 (M+H)⁺.

Intermediate 29

{7-Bromo-4-[3-oxo-3,4-dihydro-2H-1,4-benzoxazin-6-carbonyl]-3,4-dihydro-2H-1,4-benzoxazin-3-yl}acetic acid LiOH (55.3 mg, 2.31 mmol) dissolved in water (3 mL) was added to a solution of ethyl {7-bromo-4-[(3-oxo-3,4-dihydro-2H-1,4-benzoxazin-6-yl)carbonyl]-3,4-dihydro-2H-1,4-benzoxazin-3-yl}acetate (Intermediate 28, 366 mg, 0.77 mmol) in THF (6.0 mL). The mixture was stirred at rt for 1.5 h. EtOAc (40 mL) was added followed by 1 M HCl (3.1 mL, 3.1 mmol) and water (20 mL). The phases were separated and the organic layer was washed with brine (30 mL), dried over Na₂SO₄ and evaporated to give crude title compound (372 mg, 108%) as a solid.

MS m/z 447 (M+H)⁺.

Intermediate 29a

{(3S)-7-Bromo-4-[(3-oxo-3,4-dihydro-2H-1,4-benzoxazin-6-yl)carbonyl]-3,4-dihydro-2H-1,4-benzoxazin-3-yl}acetic acid Ethyl 2-[(3S)-7-bromo-4-(3-oxo-4H-1,4-benzoxazine-6-carbonyl)-2,3-dihydro-1,4-benzoxazin-3-yl]acetate (Intermediate 28a, 173 mg, 0.37 mmol) was dissolved in THF (1.5 mL). Lithium hydroxide (52.5 mg, 2.19 mmol) dissolved in water (1.50 mL) was added. The reaction was stirred at rt for 2 h before addition of EtOAc (50 mL). The organic layer was washed with HCl (1M, 30 mL) and brine (30 mL). Dried through a phase separator and evaporated under reduced pressure. The title compound (160 mg, 98%) was obtained crude and used without further purification.

MS m/z 447.0 (M+H)⁺.

EXAMPLES

Example 1

2-{4-[3-Oxo-3,4-dihydro-2H-1,4-benzoxazin-6-yl)carbonyl]-3,4-dihydro-2H-1,4-benzoxazin-3-yl}acetamide

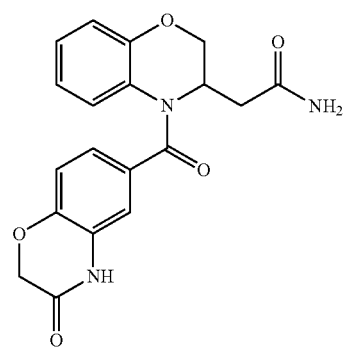 [SMILES: NC(=O)CC1COc2ccccc2N1C(=O)c1ccc2c(c1)NC(=O)CO2]

Ethyl chloroformate (0.038 mL, 0.39 mmol) was added at rt to a solution of {4-[(3-oxo-3,4-dihydro-2H-1,4-benzoxazin-6-yl)carbonyl]-3,4-dihydro-2H-1,4-benzoxazin-3-yl}acetic acid (Intermediate 5, 132 mg, 0.36 mmol) and TEA (0.150 mL, 1.08 mmol) in dry THF (8 mL). After a few seconds, a cloudy precipitate was formed. After 30 min, ammonium hydroxide solution (1 mL, 26% NH$_3$) was added and stirring was continued for 1 h. The mixture was concentrated under reduced pressure and the residue taken up in DCM (15 mL) and washed with sat. aq. NaHCO$_3$ (10 mL) using a phase separator. When the phases were separated the product precipitated from the organic phase. The organic phase was concentrated giving the title compound (112 mg, 85%) as a white solid. A small part of the product (30 mg) was purified further by preparative HPLC (Sunfire C18 column (5 μm 150×19 ID mm) using a gradient of 5 to 95% ACN in 0.1 M FA at pH 3) to give the title compound (16 mg, 53.3% based on the 30 mg withdrawn sample). $^1$H NMR (600 MHz, DMSO-d$_6$) δ 2.34-2.47 (m, 2H), 4.2-4.36 (m, 2H), 4.66 (s, 2H), 4.71-4.84 (m, 1H), 6.72-6.78 (m, 1H), 6.92-7.14 (m, 7H), 7.42 (s, 1H), 10.83 (s, 1H). HRMS Calcd for [C$_{19}$H$_{17}$N$_3$O$_5$+H$^+$]: 368.1246. found: 368.12438 (M+H)$^+$.

Example 2, Method A

N-Methyl-2-{4-[3-oxo-3,4-dihydro-2H-1,4-benzoxazin-6-yl)carbonyl]-3,4-dihydro-2H-1,4-benzoxazin-3-yl}acetamide

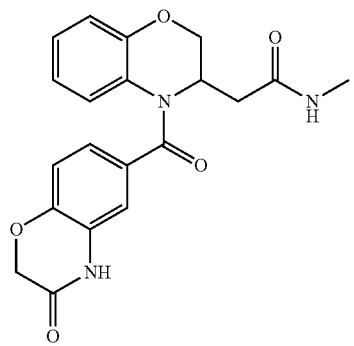 [SMILES: CNC(=O)CC1COc2ccccc2N1C(=O)c1ccc2c(c1)NC(=O)CO2]

A solution of {4-[(3-oxo-3,4-dihydro-2H-1,4-benzoxazin-6-yl)carbonyl]-3,4-dihydro-2H-1,4-benzoxazin-3-yl}acetic acid (Intermediate 5, 50 mg, 0.14 mmol), methanamine (0.339 mL, 0.68 mmol, 2 M solution in THF), and TEA (0.056 mL, 0.41 mmol) in DMF (1 mL) was treated with a T3P (50 wt. % in EtOAc, 0.161 mL, 0.27 mmol) at rt. The reaction mixture was stirred at rt over night and concentrated. The crude material was purified by preparative HPLC (Xbridge C18 column (5 μm 150×19 ID mm), a gradient of 5-95% ACN in H$_2$O/ACN/NH$_3$ 95/5/0.2 buffer) to give the title compound (40.0 mg, 77%).

$^1$H NMR (600 MHz, DMSO-d$_6$) δ 2.36-2.39 (m, 2H), 2.55 (d, 3H), 4.12-4.31 (m, 2H), 4.64 (s, 2H), 4.68-4.87 (m, 1H), 6.73 (t, 1H), 6.89-6.95 (m, 2H), 6.97-7.02 (m, 2H), 7.02-7.06 (m, 1H), 7.07-7.1 (m, 1H), 7.79-7.94 (m, 1H), 10.81 (s, 1H). HRMS Calcd for [C$_{20}$H$_{19}$N$_3$O$_5$+H$^+$]: 382.1403. found: 382.1413.

Example 2, Method B

N-Methyl-2-{4-[(3-oxo-3,4-dihydro-2H-1,4-benzoxazin-6-carbonyl]-3,4-dihydro-2H-1,4-benzoxazin-3-yl}acetamide

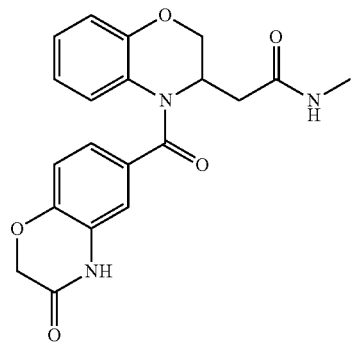

Methylamine (375 mL) was added slowly into a solution of methyl-2-[4-[(3-oxo-3,4-dihydro-2H-1,4-benzoxazin-6-yl)carbonyl]-3,4-dihydro-2H-1,4-benzoxazin-3-yl]acetate (Intermediate 3, 12.5 g, 32.7 mmol) in MeOH (750 mL) at rt. The resulting mixture was stirred at rt for 16 h. The organic solvent was removed by evaporation under reduced pressure. The crude product was purified by re-crystallization from MeOH to afford the title compound (12.0 g, 96%) as a white solid. This material was combined with three batches prepared as above to yield 5.0 g, 10.3 g and 12.0 g of the title compound from 5.28 g, 10.68 g and 12.5 g of Intermediate 3. The combined batch was suspended in 40 mL of MeOH and stirred for 30 min. The suspension was filtered and the solid was dried under vacuum to yield 35.7 g of the title compound.

$^1$H NMR (300 MHz, DMSO-d$_6$) δ 2.39 (2H, d), 2.56 (3H, d), 4.25 (2H, s), 4.65 (2H, s), 4.77 (1H, t), 6.75 (1H, ddd), 6.91-7.10 (6H, m), 7.89 (1H, q), 10.78 (1H, s).

MS m/z 382 (M+H)$^+$.

Example 2, Method C

N-Methyl-2-{4-[(3-oxo-3,4-dihydro-2H-1,4-benzoxazin-6-yl)carbonyl]-3,4-dihydro-2H-1,4-benzoxazin-3-yl}acetamide

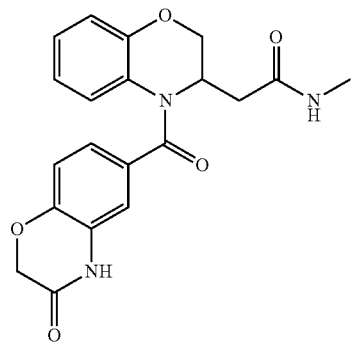 [SMILES: CNC(=O)CC1COc2ccccc2N1C(=O)c1ccc2c(c1)NC(=O)CO2]

Methylamine (370 mL) was added slowly into a solution of ethyl {4-[(3-oxo-3,4-dihydro-2H-1,4-benzoxazin-6-yl)carbonyl]-3,4-dihydro-2H-1,4-benzoxazin-3-yl}acetate (Intermediate 4, 10.7 g, 26.9 mmol) in MeOH (640 mL) at rt. The resulting mixture was stirred at rt for 16 h. The organic solvent was removed by evaporation under reduced pressure. The crude product was purified by re-crystallization from MeOH to afford the title compound (10.3 g, 100%) as a white power.

$^1$H NMR (300 MHz, DMSO-d$_6$) δ 2.39 (2H, d), 2.56 (3H, d), 4.25 (2H, s), 4.66 (2H, s), 4.77 (1H, t), 6.75 (1H, ddd), 6.91-7.10 (6H, m), 7.89 (1H, q), 10.83 (1H, s).

MS m/z 382 (M+H)$^+$.

Example 2a and 2b, Method D

N-Methyl-2-{3S and 3R)-4-[(3-oxo-3,4-dihydro-2H-1,4-benzoxazin-6-yl)carbonyl]-3,4-dihydro-2H-1,4-benzoxazin-3-yl}acetamide The enantiomers of Example 2 (23 mg, 0.06 mmol) were separated by chiral separation, using a ReproSil column (8 μm, 250×30 mm) with a mobile phase of 30% EtOH in CO$_2$, at 150 bar at 40° C., with a flow of 80 mL/min and detection at 250 nm.

Example 2a, Method D

N-Methyl-2-{3S or 3R)-4-[(3-oxo-3,4-dihydro-2H-1,4-benzoxazin-6-yl)carbonyl]-3,4-dihydro-2H-1,4-benzoxazin-3-yl}acetamide

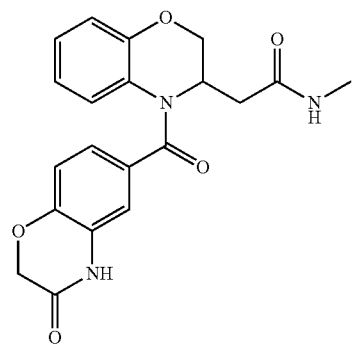 [SMILES: CNC(=O)CC1COc2ccccc2N1C(=O)c1ccc2c(c1)NC(=O)CO2]

ISOMER 1

The first eluted compound was collected and evaporated to yield ISOMER 1 of the title compound (11 mg, 43.5%, 99.4% ee).

$^1$H NMR (500 MHz, CD$_3$OD) δ 2.35-2.59 (m, 2H), 2.70 (s, 3H), 4.31 (dd, 1H), 4.39 (d, 1H), 4.62 (s, 2H), 5.03 (t, 1H), 6.68 (t, 1H), 6.82 (d, 1H), 6.87-6.96 (m, 2H), 6.97-7.03 (m, 1H), 7.03-7.08 (m, 1H), 7.11 (dd, 1H).

HRMS Calcd for [C$_{20}$H$_{19}$N$_3$O$_5$+H$^+$]: 382.1403. found: 382.1406.

Example 2b, Method D

N-Methyl-2-{3S or 3R)-4-[(3-oxo-3,4-dihydro-2H-1,4-benzoxazin-6-yl)carbonyl]-3,4-dihydro-2H-1,4-benzoxazin-3-yl}acetamide

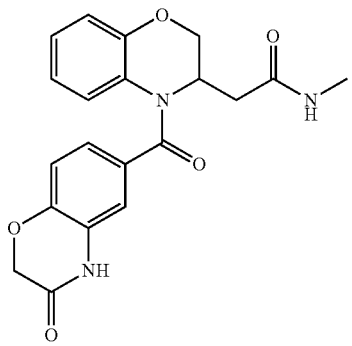

ISOMER 2

The second eluted compound was collected and evaporated to yield ISOMER 2 of the title compound (10 mg, 47.8%, 99.7% ee).

$^1$H NMR (500 MHz, CD$_3$OD) δ 2.42-2.59 (m, 2H), 2.70 (s, 3H), 4.31 (dd, 1H), 4.39 (dd, 1H), 4.62 (s, 2H), 5.03 (t, 1H), 6.63-6.71 (m, 1H), 6.82 (d, 1H), 6.88-6.97 (m, 2H), 6.97-7.03 (m, 1H), 7.06 (d, 1H), 7.11 (dd, 1H).

HRMS Calcd for [C$_{20}$H$_{19}$N$_3$O$_5$+H$^+$]: 382.1403. found: 382.1387.

Example 3

2-{7-Fluoro-4-[(3-oxo-3,4-dihydro-2H-1,4-benzoxazin-6-1 carbonyl]-3,4-dihydro-2H-1,4-benzoxazin-3-yl}acetamide

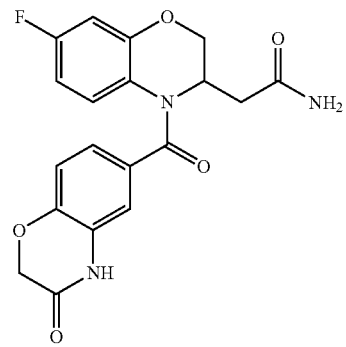

{7-Fluoro-4-[(3-oxo-3,4-dihydro-2H-1,4-benzoxazin-6-yl)carbonyl]-3,4-dihydro-2H-1,4-benzoxazin-3-yl}acetic acid (Intermediate 15, 293 mg, 0.76 mmol) was suspended in DCM (10 mL). TEA (0.631 mL, 4.55 mmol) and PyBOP (520 mg, 1.00 mmol) was added. Ammonia hydrochloride (0.162 mL, 4.55 mmol) was added and the reaction was stirred over night. The suspension was diluted with DCM, water and 3.8 M HCl(aq). The organic layer separated and the aq. layer extracted once with DCM. The combined organics were washed once with sat. aq. NaHCO$_3$ and brine, filtered through a phase separator and concentrated. The remaining oil was purified by preparative HPLC (Kromasil C8 column (10 μm 250×50 ID mm), using a gradient of 10-50% ACN in H$_2$O/ACN/FA 95/5/0.2 buffer over 20 min with a flow of 100 mL/min, UV detection at 227/254 nm). Fractions containing the product were combined, concentrated in vacuo and finally freeze dried to give the title compound (165 mg, 56.5%) as a white solid.

$^1$H NMR (500 MHz, DMSO-d$_6$) δ 2.37-2.41 (m, 2H), 4.24-4.31 (m, 2H), 4.65 (s, 2H), 4.72-4.78 (m, 1H), 6.65 (td, 1H), 6.84 (dd, 1H), 6.93-6.99 (m, 2H), 7.05-7.14 (m, 3H), 7.40 (s, 1H), 10.83 (s, 1H).

MS M/Z 386.5 (M+H)$^+$.

Example 3a and 3b

2-{(3S and 3R)-7-Fluoro-4-[3-oxo-3,4-dihydro-2H-1,4-benzoxazin-6-yl)carbonyl]-3,4-dihydro-2H-1,4-benzoxazin-3-yl}acetamide The enantiomers of Example 3 (165 mg, 0.43 mmol) were separated by chiral separation, using a ChiralPak OJ column (5 μm, 250×30 mm) with a mobile phase of 30% EtOH in CO$_2$, 175 bar at 40° C., with a flow of 80 mL/min and detection at 290 nm.

Example 3a

2-{(3S or 3R)-7-Fluoro-4-[(3-oxo-3,4-dihydro-2H-1,4-benzoxazin-6-yl)carbonyl]-3,4-dihydro-2H-1,4-benzoxazin-3-yl}acetamide

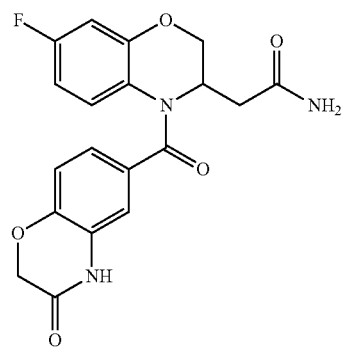

ISOMER 1

The first eluted compound was collected and evaporated to yield ISOMER 1 of the title compound (74 mg, 44.8%, 99.9% ee).

Optical rotation [α]$_D^{20}$=−103.4° (ACN, c=1).

$^1$H NMR (500 MHz, CDCl$_3$) δ 2.57 (d, 2H), 4.23-4.32 (m, 1H), 4.45 (d, 1H), 4.58 (s, 2H), 5.08 (s, 1H), 6.38-6.54 (m, 2H), 6.61-6.89 (m, 4H), 6.96 (dd, 1H), 7.19 (d, 1H), 9.73 (s, 1H).

HRMS Calcd for [C$_{19}$H$_{16}$FN$_3$O$_5$+H$^+$]: 386.1152. found: 386.1158 (M+H)$^+$.

Example 3b

2-{(3S or 3R)-7-Fluoro-4-[(3-oxo-3,4-dihydro-2H-1,4-benzoxazin-6-yl)carbonyl]-3,4-dihydro-2H-1,4-benzoxazin-3-yl}acetamide

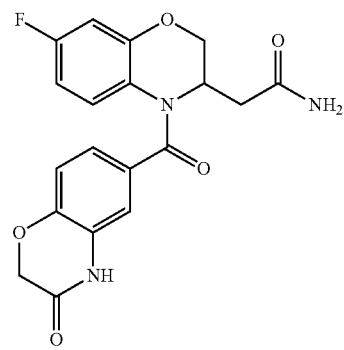 [SMILES: NC(=O)CC1COc2cc(F)ccc2N1C(=O)c1ccc2c(c1)NC(=O)CO2]

ISOMER 2

The second eluted compound was collected and evaporated to yield ISOMER 2 of the title compound (71 mg, 43.0%, 99.7% ee).

Optical rotation [α]$_D^{20}$=+108.3° (ACN, c=1).

$^1$H NMR (500 MHz, CDCl$_3$) δ 2.57 (d, 2H), 4.25-4.32 (m, 1H), 4.45 (d, 1H), 4.59 (s, 2H), 5.04-5.13 (m, 1H), 6.37-6.49 (m, 2H), 6.61-6.88 (m, 4H), 6.97 (d, 1H), 7.19 (s, 1H), 9.68 (s, 1H).

HRMS Calcd for [C$_{19}$H$_{16}$FN$_3$O$_5$+H$^+$]: 386.1152. found: 386.1157.

Example 4

2-{7-Fluoro-4-[(3-oxo-3,4-dihydro-2H-1,4-benzoxazin-6-yl)carbonyl]-3,4-dihydro-2H-1,4-benzoxazin-3-yl}-N-methylacetamide

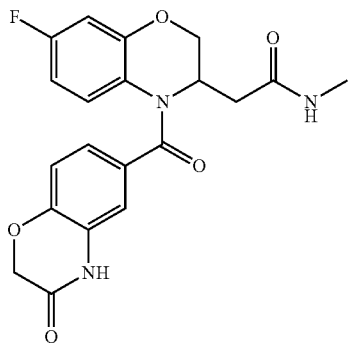 [SMILES: CNC(=O)CC1COc2cc(F)ccc2N1C(=O)c1ccc2c(c1)NC(=O)CO2]

Methanamine (2 M solution in THF, 259 μL, 0.52 mmol) was added to a stirred suspension of {7-fluoro-4-[(3-oxo-3,4-dihydro-2H-1,4-benzoxazin-6-yl)carbonyl]-3,4-dihydro-2H-1,4-benzoxazin-3-yl}acetic acid (Intermediate 15, 40 mg, 0.10 mmol) and TEA (43 μL, 0.31 mmol) in EtOAc (2 mL) at rt. A thick white precipitate was formed. Addition of T3P (50 wt. % in EtOAc, 123 μL, 0.21 mmol) to the mixture resulted in a clear, pale yellow reaction solution. The mixture was stirred at rt over night. EtOAc (10 mL) was added and the mixture was washed with sat. aq. NaHCO$_3$ (5 mL), HCl (1 M, 5 mL) and brine (5 mL), dried over MgSO$_4$ and concentrated in vacuo. The residue was purified by flash chromatography (using 5% MeOH in DCM as eluent), dissolved in ACN/water (approx. 5 mL, 1:4) and freeze-dried to give the title compound (19 mg, 46%) as a white solid.

$^1$H NMR (500 MHz, DMSO-d$_6$) δ 2.38 (d, 2H), 2.56 (d, 3H), 4.26 (s, 2H), 4.65 (s, 2H), 4.76 (br t, 1H), 6.65 (td, 1H), 6.83 (dd, 1H), 6.96 (d, 1H), 7.03-7.16 (m, 3H), 7.87 (q, 1H), 10.82 (s, 1H).

HRMS Calcd for [C$_{20}$H$_{18}$FN$_3$O$_5$+H$^+$]: 400.1309. found: 400.1331.

Examples 4a and 4b, Method A

2-{(3S and 3R)-7-Fluoro-4-[3-oxo-3,4-dihydro-2H-1,4-benzoxazin-6-carbonyl]-3,4-dihydro-2H-1,4-benzoxazin-3-yl}-N-methylacetamide The enantiomers of Example 4 (103 mg, 0.26 mmol) were separated by chiral separation, using a ReproSil column (5 μm, 250×30 mm) with a mobile phase of 30% EtOH/DEA 100/0.5 in CO$_2$ at 175 bar and 40° C., with a flow of 80 g/min and detection at 260 nm.

Example 4a, Method A

2-{(3S)-7-Fluoro-4-[(3-oxo-3,4-dihydro-2H-1,4-benzoxazin-6-yl)carbonyl]-3,4-dihydro-2H-1,4-benzoxazin-3-yl}-N-methylacetamide

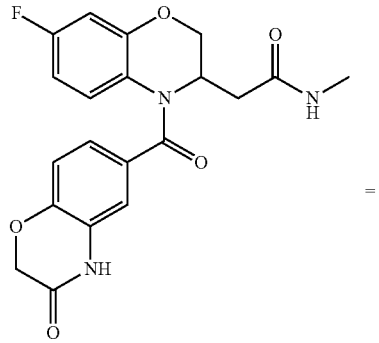

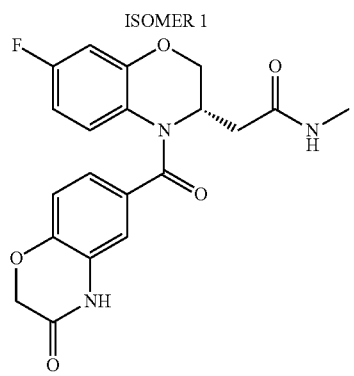

ISOMER 1

The first eluted compound was collected and evaporated to yield ISOMER 1 of the title compound (33 mg, 32%, 99.9% ee).

$^1$H NMR (500 MHz, DMSO-d$_6$) δ 2.38 (d, 2H), 2.56 (d, 3H), 4.26 (s, 2H), 4.65 (s, 2H), 4.71-4.79 (m, 1H), 6.62-6.68 (m, 1H), 6.84 (dd, 1H), 6.96 (d, 1H), 7.03-7.09 (m, 2H), 7.11 (br m, 1H), 7.87 (q, 1H), 10.81 (s, 1H).

HRMS Calcd for [C$_{20}$H$_{18}$FN$_3$O$_5$+H$^+$]: 400.1309. found: 400.1312.

Example 4b, Method A

2-{(3R)-7-Fluoro-4-[(3-oxo-3,4-dihydro-2H-1,4-benzoxazin-6-yl)carbonyl]-3,4-dihydro-2H-1,4-benzoxazin-3-yl}-N-methylacetamide

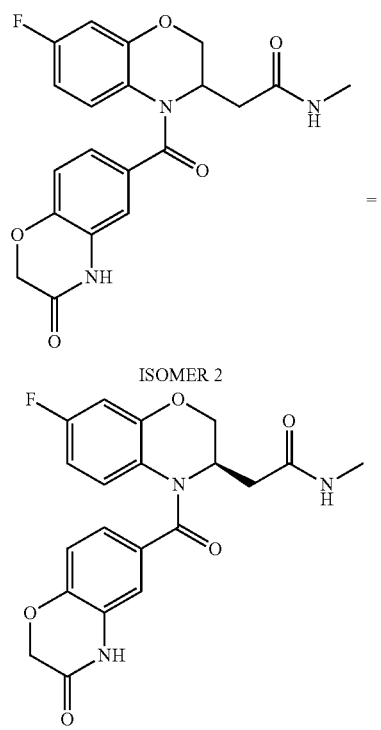

ISOMER 2

The second eluted compound was collected and evaporated to yield ISOMER 2 of the title compound (26 mg, 25%, 99.9% ee).

$^1$H NMR (500 MHz, DMSO-d$_6$) δ 2.38 (d, 2H), 2.56 (d, 3H), 4.26 (s, 2H), 4.65 (s, 2H), 4.71-4.8 (m, 1H), 6.65 (td, 1H), 6.84 (dd, 1H), 6.96 (d, 1H), 7.07 (d, 2H), 7.11 (s, 1H), 7.87 (q, 1H), 10.82 (br s, 1H).

HRMS Calcd for [C$_{20}$H$_{18}$FN$_3$O$_5$+H$^+$]: 400.1309. found: 400.1297.

Example 4a, Method B

2-{(3S)-7-Fluoro-4-[(3-oxo-3,4-dihydro-2H-1,4-benzoxazin-6-yl)carbonyl]-3,4-dihydro-2H-1,4-benzoxazin-3-yl}-N-methylacetamide

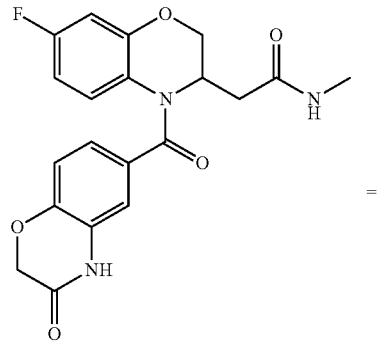

ISOMER 1

-continued

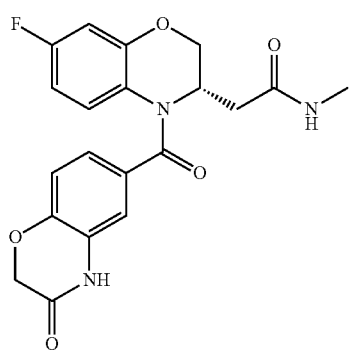

Ethyl {(3S)-7-fluoro-4-[(3-oxo-3,4-dihydro-2H-1,4-benzoxazin-6-yl)carbonyl]-3,4-dihydro-2H-1,4-benzoxazin-3-yl}acetate (Intermediate 14a, 1648 g) was taken up in methanol (10 L). Methylamine in ethanol (33 wt %, 20 eq., 7490 mL) was added at <30° C. The resulting solution was stirred at rt for 18 h. LCMS analysis indicated the reaction was not complete. The reaction was stirred for a further 4 h at rt after which HPLC indicated that <1% Intermediate 14a and its corresponding methyl ester remained (combined). The solvent was removed in vacuo to give the crude product as a tan solid (1719.2 g). This was combined with 376 g crude product from another batch and the combined crude product (2095 g) was taken up in IPA (20950 mL) and heated to reflux. A solution was not obtained. The suspension was sampled and the sample cooled and filtered for XRPD analysis. This indicated the product was of the desired form (type 2). HPLC analysis of the filtered material indicated a purity of 99.2% confirming purification had been successful. The suspension was cooled to room temperature over night. The solid was filtered, washed with IPA (3×2 L) and pulled dry. Further drying in a vacuum oven at 60° C. yielded the title product as an off-white solid (1632.5 g). $^1$H NMR indicated a purity of >95% (0.18% residual IPA). This material was combined with the product from another smaller scale recrystallisation (input 250 g crude) to give a total of 1820.7 g of the title compound.

$^1$H NMR (500 MHz, DMSO-$d_6$) δ 2.31-2.42 (m, 2H), 2.55 (d, 3H), 4.25 (d, 2H), 4.64 (s, 2H), 4.68-4.8 (m, 1H), 6.64 (td, 1H), 6.82 (dd, 1H), 6.95 (d, 1H), 7.04-7.07 (m, 2H), 7.09 (br s, 1H), 7.77-7.97 (m, 1H), 10.80 (s, 1H).

HRMS Calcd for [$C_{20}H_{18}FN_3O_5$+H$^+$]: 400.1309. found: 400.1294.

The solid residue was found to be crystalline by XRPD and a typical diffractogram is displayed in FIG. 1. Characteristic peak positions are listed below.

XRPD pattern 2-Theta (°) 5.6 (s), 7.4 (vs), 9.3 (vs), 13.5 (vs), 14.8 (vs), 15.8 (vs), 16.9 (s), 18.6 (vs), 22.3 (vs), 22.6 (vs).

Example 4a, Method C

2-{(3S)-7-Fluoro-4-[(3-oxo-3,4-dihydro-2H-1,4-benzoxazin-6-yl)carbonyl]-3,4-dihydro-2H-1,4-benzoxazin-3-yl}-N-methylacetamide

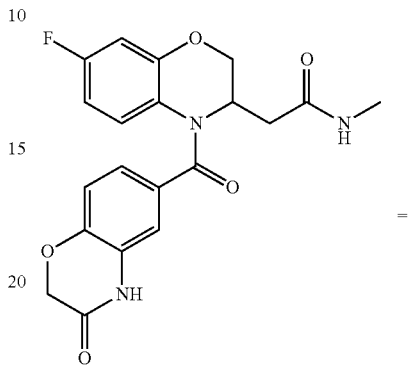

ISOMER 1

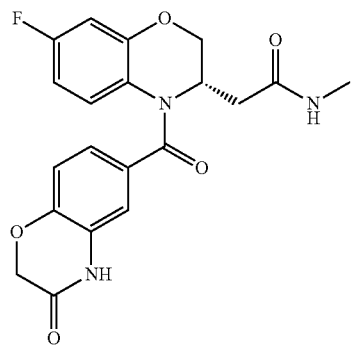

3-Oxo-3,4-dihydro-2H-1,4-benzoxazine-6-carboxylic acid (9.58 g, 48.0 mmol) was suspended with stirring in n-butyl acetate (48 mL). T3P in ethyl acetate (52.5 mL, 87.5 mmol, 50.0% w/w) was added followed by DIPEA (3.82 mL, 21.9 mmol). The resulting suspension was heated at 80° C. over night. 2-[(3S)-7-fluoro-3,4-dihydro-2H-1,4-benzoxazin-3-yl]-N-methylacetamide (Intermediate 13, 10.0 g, 43.7 mmol) was added portion wise over approximately 90 min and then held at 80° C. over night. Water (100 mL) was added and the mixture stirred at 40° C. The organic phase was collected and washed with aqueous sodium hydrogen carbonate (100 mL, 5.25% w/w) at 40° C. The organic phase was cooled to 10° C. and stirred over night. Isopropanol (100 mL) was added and the solid collected by filtration and dried under vacuum at 40° C. The title compound was obtained as an off-white solid (9.29 g, 22.3 mmol, 95.7% w/w, ee 98.4%, 50.9% yield).

$^1$H NMR (500 MHz, DMSO-$d_6$) δ ppm 2.40 (d, 2H) 2.57 (d, 3H) 4.27 (s, 2H) 4.66 (s, 2H) 4.71-4.83 (m, 1H) 6.66 (dt, 1H) 6.84 (dd, 1H) 6.96 (d, 1H) 7.04-7.19 (m, 3H) 7.90 (d, 1H) 10.86 (s, 1H).

LCMS (Agilent LC/MSD SL) calculated for [$C_{20}H_{18}FN_3O_5$+H$^+$]: 400.130. found: 400.200.

Example 4a, Method D

2-{(3S)-7-Fluoro-4-[(3-oxo-3,4-dihydro-2H-1,4-benzoxazin-6-yl)carbonyl]-3,4-dihydro-2H-1,4-benzoxazin-3-yl}-N-methylacetamide

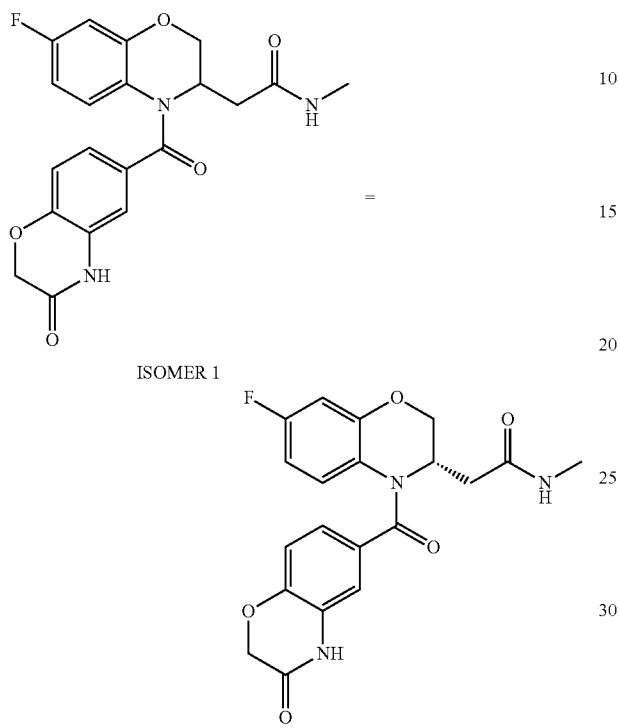

ISOMER 1

3-Oxo-3,4-dihydro-2H-1,4-benzoxazine-6-carboxylic acid (2.219 kg, 11.44 mol; 99.6 mass %) was charged to a 100 L glass-lined vessel followed by toluene (9 L). Ethyl [(3S)-7-fluoro-3,4-dihydro-2H-1,4-benzoxazin-3-yl]acetate (Intermediate 10a, 2.970 kg, 10.39 mol, 83.7 mass %) was charged and the mixture was stirred at 20° C. A solution of T3P in 2-MeTHF (11.6 L, 20.8 mol, 55.7 mass %) was then charged to the vessel within 5 minutes. Toluene (3.1 L), Pyridine (2.5 L) and toluene (3 L) were charged and the resulting mixture heated at 80° C. for 20 h then cooled to 20° C. and held for 3 days. The mixture was heated to 50° C. and washed with water (15 L). The organic phase was retained and the separated aqueous phase extracted with toluene (14.8 L). The combined organic phase was washed with aqueous sodium bicarbonate solution (14.8 L, 11.3 mol, 6.00 mass %) then water (15 L) at 39-50° C. The organic phase was cooled to 21° C., filtered to remove particulates, and a small amount of collected solid was washed with toluene (3 L). The filtrate was then concentrated to 4 relative volumes by distillation under reduced pressure to yield a solution of ethyl {(3S)-7-fluoro-4-[(3-oxo-3,4-dihydro-2H-1,4-benzoxazin-6-yl)carbonyl]-3,4-dihydro-2H-1,4-benzoxazin-3-yl}acetate in toluene. The organic phase was filtered once more and a solution of methylamine (33% w/w) in ethanol (13 L, 104 mol, 33.3 mass %) was added and the mixture stirred at 20° C. for 3 days. The mixture was evaporated to dryness under reduced pressure, then treated with 2-propanol (5 L) and re-evaporated. The 2-propanol treatment was repeated once more; 10 Lt was used to rinse the 100 Lt vessel and this was added to the collected product in the rotary evaporator vessel and the mixture evaporated to dryness. The collected solid was further dried in a vacuum oven under reduced pressure (10 mBar). The dried solid (3.985 Kg) was charged to a clean dry vessel, followed by 2-propanol (24.5 L), the mixture was stirred and heated to 80° C., held at 80° C. for 2 h then cooled to 10° C. and held at 10-11° C. for 4 days then filtered. The product cake was washed with 2-propanol (5 L) then dried in a vacuum oven at 45° C. to afford the title product (3.636 Kg; 99.4% w/w assay, 87.1% yield).

Example 5a

2-{(3S)-7-Chloro-4-[(3-oxo-3,4-dihydro-2H-1,4-benzoxazin-6-yl)carbonyl]-3,4-dihydro-2H-1,4-benzoxazin-3-yl}acetamide

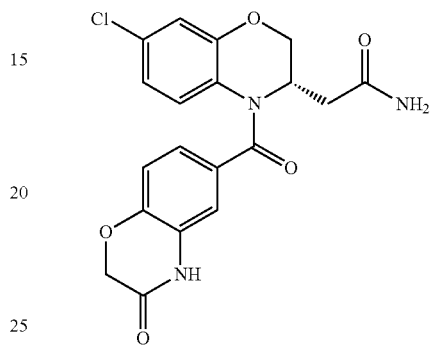

PyBOP (127 mg, 0.24 mmol) and TEA (0.141 mL, 1.02 mmol) was added to a solution of {(3S)-7-chloro-4-[(3-oxo-3,4-dihydro-2H-1,4-benzoxazin-6-yl)carbonyl]-3,4-dihydro-2H-1,4-benzoxazin-3-yl}acetic acid (Intermediate 22a, 82 mg, 0.20 mmol) in DCM (2 mL). Thereafter, $NH_4Cl$ (43.6 mg, 0.81 mmol) was added and the mixture was stirred at rt for 1.5 h. EtOAc (30 mL) was added and the mixture was washed with sat. aq. $Na_2CO_3$ (30 mL), HCl (0.5M, 20 mL) and brine (20 mL). The product was purified by preparative HPLC (Phenomenex Luna Hilic column (5 μm 250×30 ID mm) using a gradient of 10 to 45% MeOH/DEA 100/0.5 in $CO_2$, 120 bar, over 6 min at 40 OC) to give the title compound (42.0 mg, 51.3%).

$^1$H NMR (600 MHz, DMSO-$d_6$) δ 2.35-2.41 (m, 2H), 4.29 (d, 2H), 4.65 (s, 2H), 4.76 (s, 1H), 6.83 (dd, 1H), 6.93-7.01 (m, 2H), 7.01-7.12 (m, 4H), 7.39 (s, 1H), 10.83 (s, 1H).

HRMS Calcd for $[C_{19}H_{16}ClN_3O_5+H^+]$: 402.0857. found: 402.0840.

Example 5b

2-{(3R)-7-Chloro-4-[(3-oxo-3,4-dihydro-2H-1,4-benzoxazin-6-yl)carbonyl]-3,4-dihydro-2H-1,4-benzoxazin-3-yl}acetamide

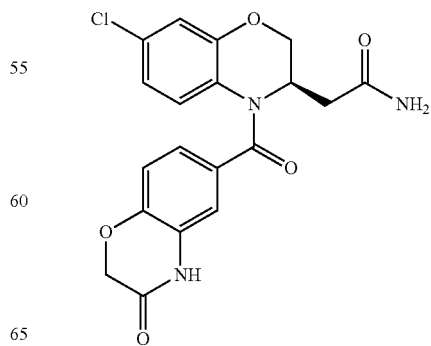

Ethyl {(3R)-7-chloro-4-[(3-oxo-3,4-dihydro-2H-1,4-benzoxazin-6-yl)carbonyl]-3,4-dihydro-2H-1,4-benzoxazin-3-yl}acetate (Intermediate 21b, 2.00 g, 4.64 mmol) dissolved in ammonia (7 M in MeOH) (49.7 mL, 348.2 mmol) sealed and stirred at rt for 45 h. The solvent was evaporated and the residue (616 mg crude brown oil) was dissolved in DMSO and MeOH. The compound was purified by preparative HPLC on a Kromasil C8 column (10 μm 250×50 ID mm) using a gradient of 10-50% ACN in H₂O/ACN/FA 95/5/0.2 buffer over 20 min with a flow of 100 mL/min. The compounds were detected by UV at 253/280 nm. Pure fractions were pooled and the most of the ACN was evaporated. The residue was partitioned between EtOAc and water. The combined organic phases were concentrated in vacuo. Addition of DMSO/ACN and water a precipitate was observed. The solvents were removed in vacuo and water was added to the residue and stirred at rt over night and filtered off to give pure title compound according to LCMS. 511 mg of off white solids were isolated, yield 27.4%.

¹H NMR (400 MHz, DMSO-$d_6$) δ 2.35-2.42 (m, 2H), 4.29 (s, 2H), 4.65 (s, 2H), 4.77 (d, 1H), 6.82 (dd, 1H), 6.96 (t, 2H), 7.02-7.12 (m, 4H), 7.39 (s, 1H), 10.83 (s, 1H).

HRMS (ESI+) m/z calculated for [$C_{19}H_{16}ClN_3O_5$+H⁺]: 402.0857. found 402.0864.

Example 6, Method A

2-{7-Chloro-4-[(3-oxo-3,4-dihydro-2H-1,4-benzoxazin-6-yl)carbonyl]-3,4-dihydro-2H-1,4-benzoxazin-3-yl}-N-methylacetamide

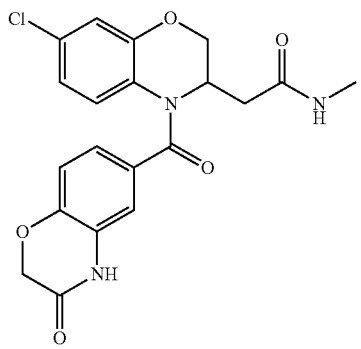

A slurry of ethyl {7-chloro-4-[(3-oxo-3,4-dihydro-2H-1,4-benzoxazin-6-yl)carbonyl]-3,4-dihydro-2H-1,4-benzoxazin-3-yl}acetate (Intermediate 21, 0.39 g, 0.91 mmol) in a mixture of MeOH (5 mL) and a 33% solution of methanamine (15 mL, 0.91 mmol) in EtOH was stirred at rt over night giving clean conversion to the amide. The reaction mixture was concentrated under reduced pressure giving the title compound (0.370 g, 98%) as a white solid.

¹H NMR (500 MHz, DMSO-$d_6$) δ 2.28-2.41 (m, 2H), 2.56 (d, 3H), 4.21-4.3 (m, 2H), 4.64 (s, 2H), 4.76 (t, 1H), 6.82 (dd, 1H), 6.95 (d, 1H), 7-7.1 (m, 4H), 7.66-7.93 (m, 1H), 10.82 (s, 1H).

MS m/z 416 (M+H)⁺.

Example 6, Method B

2-{7-Chloro-4-[(3-oxo-3,4-dihydro-2H-1,4-benzoxazin-6-yl)carbonyl]-3,4-dihydro-2H-1,4-benzoxazin-3-yl}-N-methylacetamide

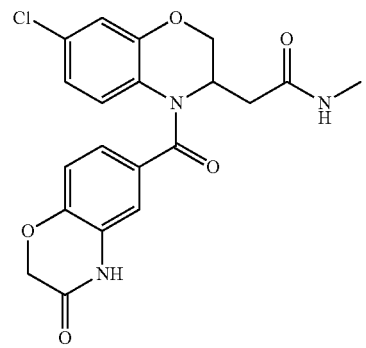

A mixture of 2-(7-chloro-4-(3-oxo-3,4-dihydro-2H-benzo[b][1,4]oxazine-6-carbonyl)-3,4-dihydro-2H-benzo[b][1,4]oxazin-3-yl)acetic acid (Intermediate 22, 38 mg, 0.09 mmol), methanamine (0.236 mL, 0.47 mmol) (2 M solution in THF), and TEA (0.039 mL, 0.28 mmol) in EtOAc (2 mL) was treated with T3P (50 wt. % in EtOAc, 0.112 mL, 0.19 mmol) at rt. The reaction mixture was stirred at rt over night and concentrated. The crude product was purified by preparative HPLC (Kromasil C8 column (10 μm 250×20 ID mm), using a gradient of 20-60% ACN in H₂O/ACN/FA 95/5/0.2 buffer, over 20 min with a flow of 19 mL/min, UV detection at 240 nm). Freeze-drying gave the title compound (24 mg, 61%) as a white powder.

¹H NMR (500 MHz, DMSO-$d_6$) δ 2.34-2.4 (m, 2H), 2.54 (d, 3H), 4.21-4.32 (m, 2H), 4.64 (s, 2H), 4.76 (t, 1H), 6.82 (dd, 1H), 6.95 (d, 1H), 7.01-7.1 (m, 4H), 7.78-7.97 (m, 1H), 10.82 (s, 1H).

HRMS Calcd for [$C_{20}H_{18}ClN_3O_5$+H⁺]: 416.1013. found: 416.1007.

Example 6a and 6b, Method A

2-{(3S and 3R)-7-Chloro-4-[(3-oxo-3,4-dihydro-2H-1,4-benzoxazin-6-yl)carbonyl]-3,4-dihydro-2H-1,4-benzoxazin-3-yl}-N-methylacetamide The enantiomers of Example 6 (0.45 g, 1.08 mmol) were separated by chiral separation, using a ChiralPak AD column (5 m, 250×30 mm) with a mobile phase of 30% iPrOH in CO₂, 120 bar at 40° C., with a flow of 120 mL/min and detection at 254 nm.

Example 6a, Method A

2-{(3S)-7-Chloro-4-[(3-oxo-3,4-dihydro-2H-1,4-benzoxazin-6-yl)carbonyl]-3,4-dihydro-2H-1,4-benzoxazin-3-yl}-N-methylacetamide

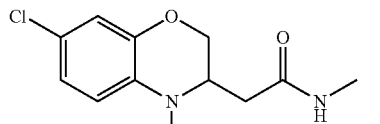

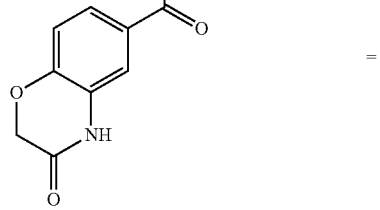

ISOMER 1

The first eluted compound was collected and evaporated to yield ISOMER 1 of the title compound (215 mg, 48%, 99.9% ee).

$^1$H NMR (500 MHz, CD$_3$OD) δ 2.42-2.52 (m, 2H), 2.70 (s, 3H), 4.31 (dd, 1H), 4.39 (dd, 1H), 4.62 (s, 2H), 5.01 (t, 1H), 6.65-6.76 dd, 1H), 6.81-6.92 (m, 1H), 6.92-6.98 (m, 2H), 7.06 (d, 1H), 7.11 (dd, 1H).

HRMS Calcd for [C$_{20}$H$_{18}$ClN$_3$O$_5$+H$^+$]: 416.1013. found: 416.1026.

Example 6b, Method A

2-{(3R)-7-Chloro-4-[(3-oxo-3,4-dihydro-2H-1,4-benzoxazin-6-yl)carbonyl]-3,4-dihydro-2H-1,4-benzoxazin-3-yl}-N-methylacetamide

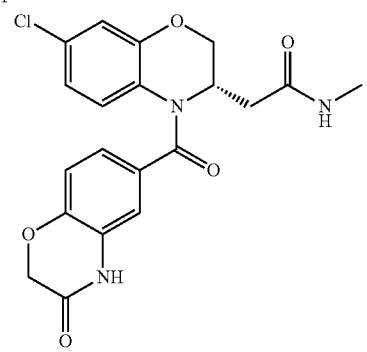

ISOMER 2

The second eluted compound was collected and evaporated to yield ISOMER 2 of the title compound (198 mg, 44%, 97.3% ee).

$^1$H NMR (500 MHz, CD$_3$OD) δ 2.30-2.57 (m, 2H), 2.71 (s, 3H), 4.32 (dd, 1H), 4.40 (dd, 1H), 4.64 (s, 2H), 5.02 (t, 1H), 6.72 (dd, 1H), 6.83-6.93 (m, 1H), 6.95-7.00 (m, 2H), 7.07 (d, 1H), 7.13 (dd, 1H).

HRMS Calcd for [C$_{20}$H$_{18}$ClN$_3$O$_5$+H$^+$]: 416.1013. found: 416.1024.

Example 6a, Method B

2-{(3S)-7-Chloro-4-[(3-oxo-3,4-dihydro-2H-1,4-benzoxazin-6-yl)carbonyl]-3,4-dihydro-2H-1,4-benzoxazin-3-yl}-N-methylacetamide

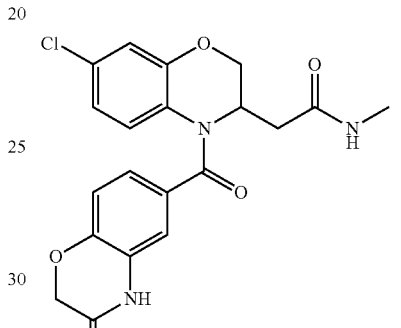

ISOMER 1

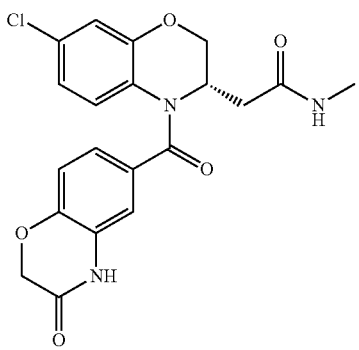

MEA (30% solution in EtOH, 175 g, 1.86 mol) was added into a solution of ethyl {(3S)-7-chloro-4-[(3-oxo-3,4-dihydro-2H-1,4-benzoxazin-6-yl)carbonyl]-3,4-dihydro-2H-1,4-benzoxazin-3-yl}acetate (Intermediate 21a, 40 g, 92.8 mmol) in MeOH (100 mL). The resulting solution was stirred at rt for 24 h. The resulting mixture was concentrated by evaporation. The crude product was purified by re-crystallization from ACN (300 mL) to afford the title compound (32.7 g, 85% yield, ee 100%) as a white solid.

$^1$H NMR (300 MHz, DMSO-d$_6$) δ 2.38 (2H, d), 2.56 (3H, d), 4.23-4.31 (2H, m), 4.65 (2H, s), 4.77 (1H, t), 6.82 (1H, dd), 6.95 (1H, d), 7.03-7.09 (4H, m), 7.86 (1H, q), 10.71 (1H, s).

HRMS m/z calculated for [C$_{20}$H$_{18}$ClN$_3$O$_5$+H$^+$]: 416.1013. found 416.0991.

Example 7

2-{(3S)-7-Bromo-4-[(3-oxo-3,4-dihydro-2H-1,4-benzoxazin-6-yl)carbonyl]-3,4-dihydro-2H-1,4-benzoxazin-3-yl}acetamide

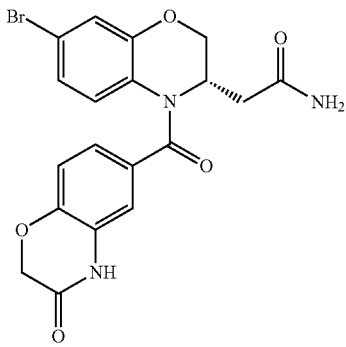 [SMILES: NC(=O)C[C@H]1COc2cc(Cl)ccc2N1C(=O)c1ccc2c(c1)NC(=O)CO2]

{(3S)-7-Bromo-4-[(3-oxo-3,4-dihydro-2H-1,4-benzoxazin-6-yl)carbonyl]-3,4-dihydro-2H-1,4-benzoxazin-3-yl}acetic acid (Intermediate 29a, 160 mg, 0.36 mmol) was dissolved in DCM (3 mL). PyBOP (223 mg, 0.43 mmol) and TEA (0.248 mL, 1.79 mmol) was added followed by NH$_4$Cl (77 mg, 1.43 mmol). The mixture was stirred at rt over weekend. EtOAc (40 mL) was added. Washed with sat. aq. Na$_2$CO$_3$ (2×30 mL), HCl (0.5M, 20 mL) and brine (20 mL). Dried through a phase separator and evaporated under reduced pressure. The residue was purified using a SFC2-MS system and eluting with MeOH on a Waters Viridis 2-EP column 5μ30×250 mm. Pooling of homogenous fraction and removal of solvents in vacuo gave the title compound (46.1 mg, 28.9%).

$^1$H NMR (600 MHz, DMSO-d$_6$) δ 2.31-2.45 (m, 2H), 4.29 (d, 2H), 4.65 (s, 2H), 4.76 (s, 1H), 6.9-7.04 (m, 4H), 7.08 (d, 2H), 7.17 (d, 1H), 7.40 (s, 1H), 10.83 (s, 1H).

HRMS (ESI+) m/z calculated for [C$_{19}$H$_{16}$N$_3$O$_5$+H$^+$]: 446.0352. found 446.0346.

Example 8

2-{7-Bromo-4-[(3-oxo-3,4-dihydro-2H-1,4-benzoxazin-6-yl)carbonyl]-3,4-dihydro-2H-1,4-benzoxazin-3-yl}-N-methylacetamide

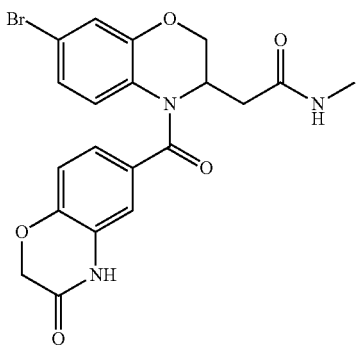 [SMILES: CNC(=O)CC1COc2cc(Cl)ccc2N1C(=O)c1ccc2c(c1)NC(=O)CO2]

TEA (0.461 mL, 3.33 mmol) and T3P (50 wt. % in EtOAc, 0.989 mL, 1.66 mmol) were added to a solution of {7-bromo-4-[(3-oxo-3,4-dihydro-2H-1,4-benzoxazin-6-yl)carbonyl]-3,4-dihydro-2H-1,4-benzoxazin-3-yl}acetic acid (Intermediate 29, 372 mg, 0.83 mmol) in EtOAc (5 mL). The mixture was stirred for 5 min. Methanamine in THF (1.248 mL, 2.50 mmol) was added and the mixture was stirred at rt for 2 h. EtOAc (50 mL) was added and the mixture washed with Na$_2$CO$_3$ (40 mL), HCl (1 M, 30 mL) and brine (30 mL), dried through a phase separator and evaporated. The compound was purified by preparative HPLC (Kromasil C8 column (10 μm 250×50 ID mm) using a gradient of 15-55% ACN in H$_2$O/ACN/FA 95/5/0.2 buffer over 20 min with a flow of 100 mL/min, UV detection at 254/280 nm) to give the title compound (215 mg, 56%) as a white solid.

$^1$H NMR (500 MHz, DMSO-d$_6$) δ 2.35-2.42 (m, 2H), 2.56 (d, 3H), 4.21-4.32 (m, 2H), 4.65 (s, 2H), 4.78 (t, 1H), 6.89-7.04 (m, 3H), 7.04-7.14 (m, 2H), 7.16 (d, 1H), 7.87 (d, 1H), 10.83 (s, 1H).

HRMS Calcd for [C$_{20}$H$_{18}$BrN$_3$O$_5$+H$^+$]: 460.0508. found: 460.0506.

Example 8a and 8b, Method A

2-{(3S and 3R)-7-Bromo-4-[(3-oxo-3,4-dihydro-2H-1,4-benzoxazin-6-yl)carbonyl]-3,4-dihydro-2H-1,4-benzoxazin-3-yl}-N-methylacetamide The enantiomers of Example 8 (132 mg, 0.29 mmol) were separated by chiral separation, using a ChiralPak OJ column (5 μm, 250×30 mm) with a mobile phase of 15% MeOH in CO$_2$, 150 bar at 40° C., with a flow of 80 mL/min and detection at 254 nm. The products where lyophilized from t-BuOH.

Example 8a, Method A

2-{(3R)-7-Bromo-4-[(3-oxo-3,4-dihydro-2H-1,4-benzoxazin-6-yl)carbonyl]-3,4-dihydro-2H-1,4-benzoxazin-3-yl}-N-methylacetamide

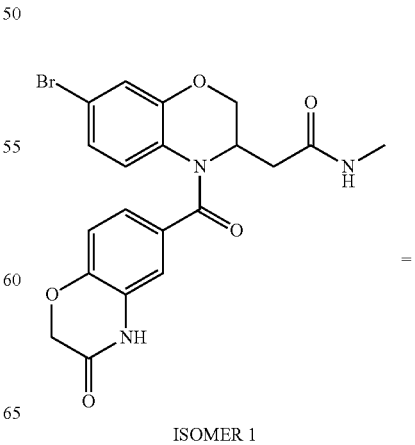

ISOMER 1

-continued

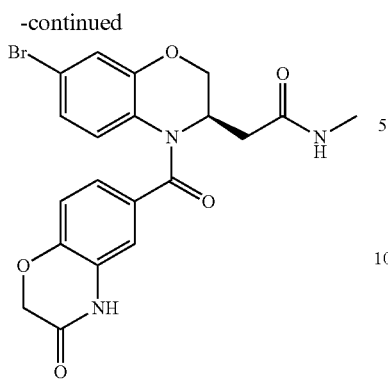

The first eluted compound was collected and evaporated to yield ISOMER 1 of the title compound (53.7 mg, 40.7%, 97.2% ee).

Optical rotation $[\alpha]_D^{20} = -87.6°$ (ACN, c=1).

HRMS Calcd for $[C_{20}H_{18}BrN_3O_5+H^+]$: 460.0508. found: 460.0522.

Example 8b, Method A

2-{(3S)-7-Bromo-4-[(3-oxo-3,4-dihydro-2H-1,4-benzoxazin-6-yl)carbonyl]-3,4-dihydro-2H-1,4-benzoxazin-3-yl}-N-methylacetamide

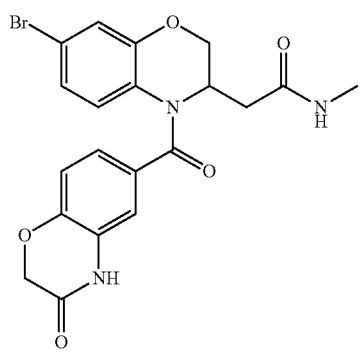 [SMILES: CNC(=O)CC1COc2cc(Cl)ccc2N1C(=O)c1ccc2c(c1)NC(=O)CO2]

ISOMER 2

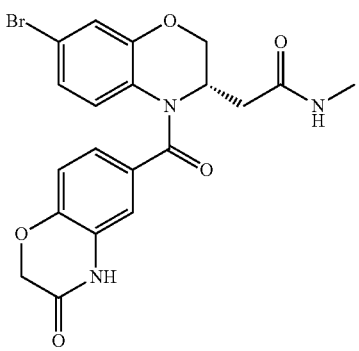 [SMILES: CNC(=O)CC1COc2cc(Br)ccc2N1C(=O)c1ccc2c(c1)NC(=O)CO2]

The second eluted compound was collected and evaporated to yield ISOMER 2 of the title compound (53.1 mg, 40.2%, 98.9% ee).

Optical rotation $[\alpha]_D^{20} = +92.5°$ (ACN, c=1).

HRMS Calcd for $[C_{20}H_{18}BrN_3O_5+H^+]$: 460.0508. found: 460.0535.

Example 8b, Method B

2-{(3S)-7-Bromo-4-[(3-oxo-3,4-dihydro-2H-1,4-benzoxazin-6-yl)carbonyl]-3,4-dihydro-2H-1,4-benzoxazin-3-yl}-N-methylacetamide

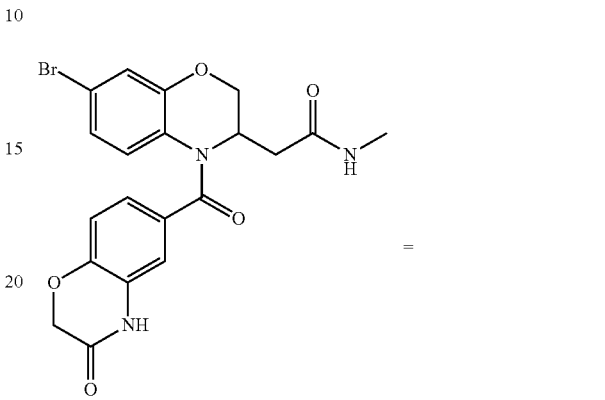

ISOMER 2

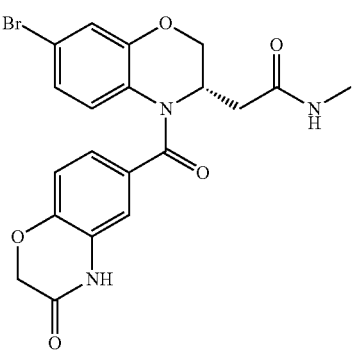

MEA (33% solution in EtOH) (53.6 g, 570 mmol) was added to ethyl 2-[(3S)-7-bromo-4-(3-oxo-4H-1,4-benzoxazine-6-carbonyl)-2,3-dihydro-1,4-benzoxazin-3-yl]acetate (Intermediate 28a, 18.8 g, 39.6 mmol) in MeOH (94 mL) at rt. The resulting solution was stirred at 25° C. for 15 h. The solvent was removed in vacuo. The crude product was purified by recrystallization from MeCN/MeOH (20:1) to afford the title compound (12.5 g, 69% yield, ee 100%) as a white solid. This batch combined with three batches prepared as above which yielded 4.2 g, 17 g and 11.5 g of title compound from 5.0 g, 16.6 g and 17.0 g starting material respectively. The pooled title compounds were recrystallized from ACN/MeOH to afford 35.09 g title compound.

$^1$H NMR (300 MHz, DMSO-$d_6$) δ 2.38 (2H, d), 2.56 (3H, d), 4.27 (2H, s), 4.66 (2H, s), 4.77 (1H, t), 6.92-7.02 (3H, m), 7.06-7.09 (2H, m), 7.16 (1H, d), 7.87 (1H, q), 10.83 (1H, s).

HRMS (ESI+) m/z calculated for $[C_{20}H_{18}BrN_3O_5+H^+]$: 460.0508. found 460.0500.

Pharmacological Activity

The following test procedures may be employed

Mineralocorticoid Binding, Test A

In order to identify binding to the human MR LBD a scintillation proximity assay (SPA) was adapted to the 384-well format. The MR-LBD (amino acids T729-K985) was expressed as N-terminal fusion with maltose binding protein in Hi5 insect cells by co-infection with recombinant MBP-MR LBD and P23 baculoviruses and crude protein lysate was used in the assay. Tritiated aldosterone is used as the ligand to generate the scintillation signal when brought into proximity of the scintillation (SPA) bead by binding to the MR LBD and test compound affinity (in $IC_{50}$ values) is defined as the concentration to decrease tritiated aldosterone binding to the MR LBD by 50%.

Briefly, in Test A1 the assay was run in 384 well format in 10 mM Tris-HCl, pH 7.5, 0.5 mM EDTA 20 mM $NaMoO_4$, 0.1 mM DTT and 10% glycerol at rt. Compounds were tested in a 7 (Test A1) or 10 (Test A2) concentration response curve ranging from 10 nM to 10 μM (Test A1) or 1 nM to 37 μM (Test A2). Compounds were spotted at the bottom of a well of a 384-well PE Opti-Plate to yield final DMSO concentrations in the assay of 2%. Pre-made MBP-MR/P23 lysate: $^3$H-aldosterone mix (final assay concentration 7 μg/mL MBP-MR LBD/P23 lysate; 5 nM aldosterone) was added onto the top of the spotted compound and preincubated for 1 h at RT. After 1 h an equal volume anti-rabbit SPA beads (Test A1) or Imaging beads (Test A2) coupled with rabbit anti-MBP were added to the assay mixture and incubated for 3 hrs (Test A1) or >8 h (Test A2) at rt. The inhibition of the scintillation signal by displacement of the bound $^3$H-aldosterone by test compounds is measured by scintillation counting using a Microbeta Trilux (Wallac) (Test A1) or a by CCD camera detection using a LEADseeker (PerkinElmer) (Test A2).

Mineralocorticoid Cellular Reporter Gene Assay, Test B

To test for potency and efficacy of compounds, 25000 cells from a freshly thawed batch of cryopreserved UAS-MR-bla HEK293 cells (Invitrogen, K1696), were added to each well in a 384 well plate using a Multidrop. Cells were grown in 30 μl DMEM without phenol red (Invitrogen 21063-029) containing 2% charcoal stripped fetal bovine serum (Invitrogen 12676-029), Penicillin/Streptomycin, Non-essential amino acids and sodium pyruvate according to the Invitrogens protocoll included with the cells. Upon seeding, the plates were incubated at 37° C., 5% CO2, for 4 h to allow cells to adhere. From a plate containing compound dilution series in DMSO, typically spanning 10 concentrations (10 μM to 0.5 nM final concentration), 0.6 μL compound per well was added using a Beckman FX pipetter. The plates were incubated for 30 min prior to addition of aldosterone to a final concentration of 0.25 nM (Test B1) or 1 nM (Test B2). Following 16-20 h incubation, beta-lactamase activity was assessed by addition of 8 μL of a CCF4 containing substrate buffer prepared according to Invitrogens protocol included with the cells. Plates were left for 2 h in the dark before fluorescence was measured in a Pherastar FS with bottom reading and filters set to excitation at 409 nm and emission collection at 460 and 530 nm. After background subtraction, the 460/530 ratio was calculated for each assay point and averaged from three parallel assay plates. 0% inhibition was defined by wells that only contain aldosterone, 100% inhibition was defined by wells containing 120 nM spironolactone.

The concentration and percent activation of the Test compound is fitted using a Sigmoidal Dose-Response Model where the $EC_{50}$ is determined as the concentration of the Test compound at the midpoint of the dose-response curve. Equation: fit=(A+((B−A)/(1+((C/x)^D)))) where, A=curve bottom, B=curve top, C=$EC_{50}$, D=slope (Hill coefficient) and x=concentration of Test compound.

Results

Compounds of the Examples were tested in Test A1 and A2 and B1 and B2 as described above. The following table shows results for the Examples:

| Example | Test A1 $IC_{50}$ (nM) | Test A2 $IC_{50}$ (nM) | Test B1 $IC_{50}$ (nM) | Test B2 $IC_{50}$ (nM) |
|---|---|---|---|---|
| 1 | 1400 | 2900 | 2100 | 620 |
| 2 | | 1800 | | 300 |
| 2a | 230 | | 680 | 140 |
| 2b | | | | 5300 |
| 3 | 480 | | 920 | 240 |
| 3a | 28% at 37.5 μM | | | |
| 3b | 270 | | 840 | 140 |
| 4 | 180 | 740 | 760 | 270 |
| 4a | 130 | 240 | 420 | 84 |
| 4b | 28% at 37.5 μM | | 35% at 100 μM | |
| 5a | 16 | | 56 | |
| 5b | 4900 | | 10370 | |
| 6 | 82 | 58 | 180 | 31 |
| 6a | 13 | | 74 | 8.4 |
| 6b | 1900 | | 4100 | 1100 |
| 7 | 9.5 | | 45 | |
| 8 | 40 | | 110 | 15 |
| 8a | 1600 | | 1800 | 640 |
| 8b | 10 | | 48 | 21 |

The invention claimed is:
1. A compound of formula (I)

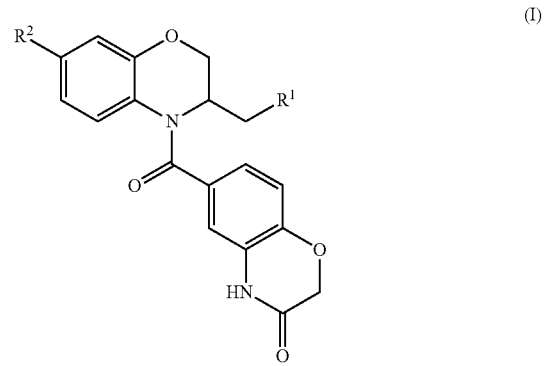

wherein
$R^1$ is selected from $CONH_2$ or $CONHCH_3$; and
$R^2$ is selected from H, F, Cl or Br;
or a pharmaceutically acceptable salt thereof.
2. A compound according to claim 1, or a pharmaceutically acceptable salt thereof, wherein
$R^1$ is $CONHCH_3$; and
$R^2$ is selected from H, F, Cl or Br.
3. A compound according to claim 1, or a pharmaceutically acceptable salt thereof, wherein
$R^1$ is $CONHCH_3$; and
$R^2$ is F.
4. A compound according to claim 1 which is selected from
2-{4-[(3-oxo-3,4-dihydro-2H-1,4-benzoxazin-6-yl)carbonyl]-3,4-dihydro-2H-1,4-benzoxazin-3-yl}acetamide;
N-methyl-2-{4-[(3-oxo-3,4-dihydro-2H-1,4-benzoxazin-6-yl)carbonyl]-3,4-dihydro-2H-1,4-benzoxazin-3-yl}acetamide;
N-methyl-2-{(3S)-4-[(3-oxo-3,4-dihydro-2H-1,4-benzoxazin-6-yl)carbonyl]-3,4-dihydro-2H-1,4-benzoxazin-3-yl}acetamide;
N-methyl-2-{(3R)-4-[(3-oxo-3,4-dihydro-2H-1,4-benzoxazin-6-yl)carbonyl]-3,4-dihydro-2H-1,4-benzoxazin-3-yl}acetamide;
2-{7-fluoro-4-[(3-oxo-3,4-dihydro-2H-1,4-benzoxazin-6-yl)carbonyl]-3,4-dihydro-2H-1,4-benzoxazin-3-yl}acetamide;

2-{(3S)-7-fluoro-4-[(3-oxo-3,4-dihydro-2H-1,4-benzoxazin-6-yl)carbonyl]-3,4-dihydro-2H-1,4-benzoxazin-3-yl}acetamide;
2-{(3R)-7-fluoro-4-[(3-oxo-3,4-dihydro-2H-1,4-benzoxazin-6-yl)carbonyl]-3,4-dihydro-2H-1,4-benzoxazin-3-yl}acetamide;
2-{7-fluoro-4-[(3-oxo-3,4-dihydro-2H-1,4-benzoxazin-6-yl)carbonyl]-3,4-dihydro-2H-1,4-benzoxazin-3-yl}-N-methylacetamide;
2-{(3S)-7-fluoro-4-[(3-oxo-3,4-dihydro-2H-1,4-benzoxazin-6-yl)carbonyl]-3,4-dihydro-2H-1,4-benzoxazin-3-yl}-N-methylacetamide;
2-{(3R)-7-fluoro-4-[(3-oxo-3,4-dihydro-2H-1,4-benzoxazin-6-yl)carbonyl]-3,4-dihydro-2H-1,4-benzoxazin-3-yl}-N-methylacetamide;
2-{7-chloro-4-[(3-oxo-3,4-dihydro-2H-1,4-benzoxazin-6-yl)carbonyl]-3,4-dihydro-2H-1,4-benzoxazin-3-yl}acetamide;
2-{(3S)-7-chloro-4-[(3-oxo-3,4-dihydro-2H-1,4-benzoxazin-6-yl)carbonyl]-3,4-dihydro-2H-1,4-benzoxazin-3-yl}acetamide;
2-{(3R)-7-chloro-4-[(3-oxo-3,4-dihydro-2H-1,4-benzoxazin-6-yl)carbonyl]-3,4-dihydro-2H-1,4-benzoxazin-3-yl}acetamide;
2-{7-chloro-4-[(3-oxo-3,4-dihydro-2H-1,4-benzoxazin-6-yl)carbonyl]-3,4-dihydro-2H-1,4-benzoxazin-3-yl}-N-methylacetamide;
2-{(3S)-7-chloro-4-[(3-oxo-3,4-dihydro-2H-1,4-benzoxazin-6-yl)carbonyl]-3,4-dihydro-2H-1,4-benzoxazin-3-yl}-N-methylacetamide;
2-{(3R)-7-chloro-4-[(3-oxo-3,4-dihydro-2H-1,4-benzoxazin-6-yl)carbonyl]-3,4-dihydro-2H-1,4-benzoxazin-3-yl}-N-methylacetamide;
2-{7-bromo-4-[(3-oxo-3,4-dihydro-2H-1,4-benzoxazin-6-yl)carbonyl]-3,4-dihydro-2H-1,4-benzoxazin-3-yl}acetamide;
2-{(3S)-7-bromo-4-[(3-oxo-3,4-dihydro-2H-1,4-benzoxazin-6-yl)carbonyl]-3,4-dihydro-2H-1,4-benzoxazin-3-yl}acetamide;
2-{(3R)-7-bromo-4-[(3-oxo-3,4-dihydro-2H-1,4-benzoxazin-6-yl)carbonyl]-3,4-dihydro-2H-1,4-benzoxazin-3-yl}acetamide;
2-{7-bromo-4-[(3-oxo-3,4-dihydro-2H-1,4-benzoxazin-6-yl)carbonyl]-3,4-dihydro-2H-1,4-benzoxazin-3-yl}-N-methylacetamide,
2-{(3S)-7-bromo-4-[(3-oxo-3,4-dihydro-2H-1,4-benzoxazin-6-yl)carbonyl]-3,4-dihydro-2H-1,4-benzoxazin-3-yl}-N-methylacetamide;
2-{(3R)-7-bromo-4-[(3-oxo-3,4-dihydro-2H-1,4-benzoxazin-6-yl)carbonyl]-3,4-dihydro-2H-1,4-benzoxazin-3-yl}-N-methylacetamide;
or a pharmaceutically acceptable salt thereof.

5. A pharmaceutical formulation comprising a compound of formula (I) or a pharmaceutically acceptable salt of a compound of formula (I) according to any one of claims 1 to 4 and a pharmaceutically acceptable carrier, excipient or diluent.

* * * * *